(12) United States Patent
Wronska et al.

(10) Patent No.: US 9,598,739 B1
(45) Date of Patent: Mar. 21, 2017

(54) HUMAN ERYTHROVIRUS

(71) Applicant: GRIFOLS THERAPEUTICS INC., Research Triangle Park, NC (US)

(72) Inventors: Danuta Wronska, Raleigh, NC (US); Brett Buno, Durham, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 394 days.

(21) Appl. No.: 14/288,691

(22) Filed: May 28, 2014

Related U.S. Application Data

(62) Division of application No. 12/724,032, filed on Mar. 15, 2010, now abandoned.

(60) Provisional application No. 61/159,967, filed on Mar. 13, 2009.

(51) Int. Cl.
*C12Q 1/70* (2006.01)

(52) U.S. Cl.
CPC ........ *C12Q 1/701* (2013.01); *C12Q 2600/112* (2013.01)

(58) Field of Classification Search
CPC .................................................. C12Q 1/701
See application file for complete search history.

(56) References Cited

U.S. PATENT DOCUMENTS

| | | | |
|---|---|---|---|
| 5,952,202 | A | 9/1999 | Aoyagi et al. |
| 6,030,787 | A | 2/2000 | Livak et al. |
| 6,936,442 | B2 | 8/2005 | Pichuantes et al. |
| 7,291,452 | B1 | 11/2007 | Nguyen et al. |
| 2003/0124578 | A1 | 7/2003 | Brentano et al. |
| 2005/0221300 | A1 | 10/2005 | Pichuantes et al. |
| 2006/0008469 | A1 | 1/2006 | Brown et al. |
| 2006/0057643 | A1 | 3/2006 | McCarthy et al. |

OTHER PUBLICATIONS

E.D. Heegaard, et al., "Human Parvovirus B19," Clinical Microbiology Reviews, Jul. 2002, vol. 15, No. 3, pp. 485-505.
K.J. Livak, et al., "Oligonucleotides with fluorescent dyes at opposite ends provide a quenched probe system useful for detection of PCR product and nucleic acid hybridization," Applied Biosystems Division, CA 94404.1995, 4:357-362, Cold Spring Harbor Laboratory Press ISSN 1054-9803/95 (1995).
Q.T. Nguyen, et al., "Identification and Characterization of a second novel human erythrovirus variant, A6," Virology, vol. 301, No. 2, Sep. 30, 2002, pp. 374-380 (2002).
Q. Nguyen, et al., "Novel Human Erythrovirus Associated with Transient Aplastic Anemia," Journal of Clinical Microbiology, Aug. 1999, vol. 37, No. 8, pp. 2483-2487 (1999).
A. Servant, et al., "Genetic Diversity within Human Erythroviruses: Identification of Three Genotypes," Journal of Virology, 76, 9124-9134 (2002).
R. Shade, et al., "Nucleotide Sequence and Genome Organization of Human Parvovirus B19 Isolated from the Serum of a Child during Aplastic Crisis," Journal of Virology, 58, 921-936 (1986).
GenBank Accession No. Ay064476 (2004).
GenBank Accession No. M13178.1 (1995).
GenBank Accession No. Z68146.1 (2004).
NCBI Reference Sequence: NC_004295.1 (2006).
Sanabani et al., "Sequence Variability of Human Erythroviruses Present in Bone Marrow of Brazilian Patients with Various Parvovirus B19-Related Hematological Symptoms," J. Clin. Microbiol. 44(2): 604 (Feb. 2006).

*Primary Examiner* — Diana B Johannsen
(74) *Attorney, Agent, or Firm* — Womble Carlyle Sandridge & Rice, LLP

(57) ABSTRACT

Nucleic acid molecules derived from sequences of novel human parvovirus B19 variant genomes are provided. Also provided are assays and kits comprising the nucleic acid molecules.

16 Claims, 39 Drawing Sheets

```
GGGCCACTAGTAAACTCAGTGTCTACAAAGGAGGGAGACAGCTCTAGTACTGGAGCTGGAAAAGCCTTAAC
AGGCCTTAGCACAGGACCTCTCAAAACACTAGAATATCCTTACGCCCTGGGCCAGTGTCTCAGCCATATC
ACCACTGGGACACAGATAAATATGTTACAGGAATAAATGCCATTCTCATGGTCAGACCACATATGGTAAT
GCTGAAGATAAAGAGTATCAGCAAGGAGTGGGTAGATTTCCAAATGAAAAAGAACAGCTAAAACAGTTACA
GGGCTAAACATGCACACCTATTTTCCCAATAAAGGAACCCAGCAATATACAGATCAAATTGAGCGCCCCC
TAATGGTGGGTTCTGTATGGAACAGAAGAGCCCTTCACTATGAAAGTCAGCTGTGGAGTAAAATTCCAAAT
TTAGATGACAGTTTTAAAACTCAGTTTGCAGCCTTAGGAGGATGGGGTTTGCATCAGCCACCTCCTCAAAT
ATTTTAAAATATTACCACAAAGTGGGCCCATTGGAGGTATTAAATCAATGGGAATTACTACCTTAGTTC
AGTATCCGTGGTAATTATGACAGTCACTATGACATTTAAATGGGGGCCCGTAAAGCTACGGGACGGTGG
AATCTTCAACCTGGAGTATATCCCCGTACGCCGTAGGTCATTTACCATATGTACTATATGACCCCACAGC
TACAGATGCAAACAACCCCTACAGACATGGATATGAAAAGCCTGAATAATTGTGGACAGCCAAAAGCCGTG
TGCACCCATTGTAAACACTCCCCACCGTGCCCTCAGCCAGGATGCGTAACTAAACGCCCACCAGTACCACC
CAGACTGTACCTGCCCCCGGGTATACCTATAAGACAGCCTAACACAAAAGATATAGACAATGTAGAA
```

ATCTGATTTGGTGTCTTCTTTTTAAAATTTTGGCGGGCTTTTTCCCGCCTTATGCAAATAAGCTGCCATGT
TTAATATTTTATTTTAATTTAATTTGGACAGACGGCTAACGGTTATTATAGCGGAGTTACGGGCGGTATAT
AAGCAGCTGCGTCTGTGGCACTTCTTTTCTGGTTGCTTTTGACTGGAATCACTTGTGTTCTTTGCCT
GCTAACTAACAGGTATTTATACTAACTTTTAATTTACTACATGGAGCTATTTCGGGCGTCTTGCACATT
TCCTCTAACATTCTGGACTGTGCTAATGATAACTGGTGGTGCTCTATGCTAGACTTAGATACTTCTGATTG
GCAACCACTAACTCATTCTAACAGATTAATGGCAATATATTTAAGCAGTGTTGCTTCTAAGCTTGATTTTA
CTGGGGGGCTGCTAGCAGGTTGCTTATACTTTTTCCAGGTGGAGTGTAACAAATTTGAGGAAGGCTATCAT
ATTCATGTAGTTATTGGTGGTCCAGGACTAAATGCTAGAAACTTAACTGTGTGTGTAGAAGGTTTATTTAA
TAATGTTCTTTACCACCTTGTAACTGAAAGTGTTAAACTTAAATTTTTGCCAGGGATGACTACCAAAGGAA
AATATTTTAGAGATGGAGAGCAGTTTATAGAAAATTACTTAATGAAAAAATTCCTTTAAATGTTGTGTGG
TGTGTAACAAATATTGACGGGTATATAGACACCTGTATTTCCGCCTCTTTCGGCGAGGAGCTTGTCAAGC
TAAAAGACCCCGCATTGCCGGCAAATGCAGACAGTGTTACTAGTGAAACCGGGGAGTCTAGCTGTGCAGGGG
GAGATGTTGTACCATTTGCTGGAAAGGGAACAAAAGCGGGGTTAAAGTTTCAAACCATGGTAAATTGGCTA
TGTGAAAACAGAGTATTTACTGAAGATAAATGGAAGTTAGTAGACATTTTAACCAGTATACCTTATTAAGTAG
TAGTCACAGTGGCAGCTTTCAAATACAAAGTGCCTTAAAGTTAGCTATTTATAAAGCTACTAACTTAGTAC
CCACTAGTACATTCTTGTTACATGCAGACTTTGAGCAGGTTACTTGCATTAAAGAAAATAAAATAGTTAAA
TTATTACTGTGTCAAAACTATGATCCTCTGCTAGTGGGGCAACATGTGTTAAGGTGGATTGACAAAAAATG
TGGTAAAAAAACACCCTATGGTTTTACGGGCCACCAAGTACTGGAAAAACAAATTTAGCTATGGCTATTG
CTAAAACTGTACCCGTGTATGGAATGGTAACTGGAATAATGAAAATTTTCCATTTAATGATGTGGCGGGG
AAAAGTTTGGTGGTCTGGGATGAAGGCATTATTAAGTCCACTATTGTGGAAGCTGCAAAAGCCATTCTAGG
TGGTCAGCCAACCAGGGTAGATCAGAAAATGCGTTGGCAGTGTGGCAGTGCCCGGTGTGCCTGTGGTCATAA
CCAGCAACGGTGACATTACATTTGTTGTAAGTGGTAATACCACTACAACTGTGCATGCTAAGCCTTAAAA
GAACGGATGGTAAAGCTAAATTTTACCATAAGGTGTACCCCGACATGGGTTTACTAACAGAGGCTGATGT
GCAACAGTGGCTAACTTGGTGTAATGCACAAAGCTGGAGCCACTATGAAAACTGGGCAATAAACTACACGT
TTGATTCCCTGGAATAAATGCAGATGCCCTCCACCCAGATCTCCAAACCACCCCCATTGTCCCAGACACC
AGTATCAGCAGCAGTGGTGGTGAAAGCTCTGAAGAACTCAGTGAAAGCAGCTTTTTCAACCTCATCACTCC
AGGCGCTGGAACAGTGAAACCCGCGCTCTAGTACGCCCTGTCCCCGGGATAGTTCAGGAGAATCATTTG
TCGGAAGCCAGTTTCCTCCGAAGTGGTAGCCCGCGTGTGGGAGGAAGCTTTTTACACGCCGCTTGCAGAT
CAGTTTGCTGAACTGTTAGTAGGGGTTGACTATGTATGGAGTGTGTAAGGGGATTGCCTGTTTGCTGTGT
GGAACATATTAATAACAGTGGGGGAGGGTTGGGGCTTTGTCCTCATTGTATTCATGTGGAGCTTGGTATA
ATGGATGGAAATTTACAGAGTTTACTCCAGACTTAGTGCGCTGTAGTTGTCATGTAGGAGCCTCTAACCCA
TTTTCTGTGTTAACTTGTAAAAAATGTGCTTACCTGTCTGGTTTACAAAGCTTTGTAGATTATGAGTAAAA
CCACTGACAAATGCTGGGAAAGTAGTGACAAATTTGCCCAGGACGTTATAAGCAGTTTGTACAATTTTAT
GAAAAAGCTACTGGAACAGATTTAGAGCTTATTCAAATTTTAAAAGATCATTACAACATTTCTTTAGACAA
TCCTTTAGAAAACCCCTCTTCTTTATTTGACTTAGTTGCTCGCATTAAAAGCAATCTTAAAAACTCTCCAG
ACCTATATAGTCATCATTTTCAGAGCCATGGACAGTTATCTGACCACCCCATTCCTTATCACCCAGTAAC
AGTAGTACAGAACCTAGAGGAGAAAATGCAGTATTTATCTAGTGAAGACTTACACAAGCCTGGGCAAGTTAG
CATACAATTACCTGGTACTAACTATGTTGGCCTGGCAATGAGCTACAAGTGGGCTTCCGCAGAATGCTG
TGGACAGTGCTGCAAGGATTCATGACTTTAGGTATAGCCAATTGCTAAGTTGGGAATAAATCCTTATCT
CATTGGACGGTAGCAGATGAGGAATTGTTAAAAAATATAAAAAATGAAACAGGGTTTCAAGCACAAGCGT
AAAAGACTACTTTACTTTAAAGGTGCAGCTGCCCCTGTGGCCCATTTTCAAGGAAGTTTACCGGAAGTGC
CCGGTACAACGGCTCAGAAAAATACCCCAGCATGACTTCAGTTAACTCTGCAGAAGCCAGCTACTGGTGCA
GGCGGGGAGGTAGCAACCCCTACAAAAAGCATGTGGAATGAAGGGGCTACATTCACTGCTAATTCTGTAAC
ATGCACATTCTCTAGGCAATTTTTAATTCCATATGATCCAGAGCATCATTATAAAGTGTTCTCCCAGCAG
CTAGTAGCTGCCCAATGCTAGCGGAAAAGAGGCAAAGTGTGCACTATTAGTCCCATTATGGGGTACTCT
ACTCCGTGGAGATACTTAGATTTAATGCTTTAAACTTGTTTTTCTCACCATTAGAGTTTCAGCACTTAAT
TGAAAATTATGGCAGCATAGCTCCAGATGCTTTAACTGTAACTATTTCAGAAATTGCTGTAAAGATGTTA
CAGACAAAACAGGGGGAGGTGTGCAAGTTACTGCACAGCACACAGGACGTTTGTGTATGTTAGTGGATCAT
GAGTATAAGTACCCATATGTGCTAGGTCAGGGACAAGACACACTAGCTCCAGAACTGCCCATTTGGGTGTA
CTTTCCCCCCAATATGCTTACTTAACAGTAGGTGAAGTAAACACACAAGGAATTTCAGGAGACAGCAAAA
AATTAGCTAGTGAAGAATCAGCTTTTTATGTGTTAGAGCACAGTTCATTTGAACTTTTAGGTACAGGGGA
TCAGCCACAATGTCCTACAAATTCCAGCAGTGCCCCAGAAAACTTAGAAGGTTGCAGCCAACATTTTA
TGAAATGTACAACCCTCTGTACGGTTCCGATTAGGGGTACCTGACACATTAGGAGGGGACCCTAAATTTA

```
GATCATTAACACACGAAGACCATGCAATTCAGCCACAAAACTTTATGCCTGGGCCACTAATAAATTCAGTA
TCTACCAAAGAAGGAGACAATTCTAATACAGGTGCTGGAAAAGCCCTTACGGGGCTTAGTACTGGCACTAG
TCAAAACACCAGAATTTCCCTACGCCCAGGGCCAGTGTCTCAGCCATACCATCACTGGGACACTGATAAAT
ATGTTACAGGAATAAATGCCATTTCACATGGACAAACCACCTATGGAAATGCTGAGGACAAAGAATATCAG
CAAGGGGTAGGAAGATTTCCAAACGAAAAGAACAGCTTAAGCAGTTACAGGGTCTTAACATGCACACATA
CTTTCCTAATAAAGGAACCCAACAATACACAGACCAAATTGAACGCCCCCTTATGGTAGGCTCTGTTTGGA
ACAGAAGAGCACTTCACTATGAAAGTCAGCTGTGGAGTAAAATCCCTAACTTAGATGATAGTTTTAAAACT
CAATTTGCAGCCCTAGGAGGTTGGGGTTTGCATCAACCACCCCCTCAAATATTTTAAAAATACTACCGCA
AAGTGGGCCAATTGGAGGTATTAAATCCATGGGAATTACTACTTTAGTTCAATATGCTGTGGGAATAATGA
CAGTTACTATGACATTTAAATTGGACCTGGAAAGGCTACTGGAAGGTGGAATCCCCAGCCTGGAGTGTAT
CCTCCTCATGCAGCTGGTCATTTACCATATGTACTGTATGACCCCACAGCTACAGATGCAAAGCAACACCA
CAGACACGGATATGAAAAGCCTGAAGAATTGTGGACTGCCAAAAGCCGTGTGCACCCATTGTAAACATTCC
CCACCGTGCCCTCTGCCAGGAACCGTCACCAATCGCCCACCTGTACCGCCCAGATTATATGTGCCCCCTCC
AATACCCCGTAGGCAACCATCTATAAAAGATACAGACGCTGTAGAGTATAAATTACTAACCCGATATGAAC
AACATGTAATAAGAATGCTAAGATTATGTAATATGTACACAAACTTGGAAAAATAAAAACCTTAAATAAAA
AATTAATAGTGTATGGTG
```

```
SEQ ID NO: 1     237  GTGTAGAGGGATTATTTAATAATGTACTTTACCACCTTGTAACTGAAAATGTAAAGCTTA  298
                      ||||||||||||||||||||||||||||||||||||||||||||||||||||||||||||
SEQ ID NO: 130   731  GTGTAGAGGGATTATTTAATAATGTACTTTATCACCTTGTAACTGAAAATGTGAAGCTAA  790

SEQ ID NO: 131   530  GTGTAGAAGGCCTTGTTTATTTAATAATGTGCTTTACCACCTTGGTAAATGAAAAGTGTTAAACTGA  589

SEQ ID NO: 132   623  GCGTAGAAGGTTTATTTAATAATGTTCTTTACCATCTTGTAACTGAAAGTGTTAAACTTA  682

SEQ ID NO: 133   618  GTGTAGAAGGTTTATTTAATAATGTTCTTTACCACCTTGTAACTGAAACTGTTAAACTTA  677

SEQ ID NO: 1     299  AATTTTTACCAGGAATGACTACAAAAGGCAAATATTTAGAGATGGAGAACAATTATAG    358
                      ||||||||||||||||||||||||||||||||||||||||||||||||||||||||||
SEQ ID NO: 130   791  AATTTTTGCCAGGAATGACTACAAAAGGCARATACTTTAGAGATGGAGAGCAGTTTATAG  850

SEQ ID NO: 131   590  AATTTTTGCCAGGAATGACTACAAAAGGAAAGTATTTTAGAGATGGAGAGCAGTTTATAG  649

SEQ ID NO: 132   683  AATTTTTGCCAGGGATGACTACCAAAGGAAAATATTTTAGAGATGGAGAGCAGTTTATAG  742

SEQ ID NO: 133   678  AATTTTTGCCAGGGATGACTACTAAAGGAAAATATTTTAGAGATGGAGAGCAGTTTATAG  737

SEQ ID NO: 1     359  AAAATTATTAATGAAAAAATACCTTAAATGTGTATGTGTGTAACCAATATTGATG       418
                      ||||||||||||||||||||||||||||||||||||||||||||||||||||||||
SEQ ID NO: 130   851  AAAACTATTTAATGAAAAAATACCTTAAATGTTAAATGTTGTATGGTGTTACTAATATTGATG  910

SEQ ID NO: 131   650  AAAATTACCTAATGAAAAAATACCTTCCTTAAATGTTCCTGTGTGGTGTAACAAATATTGACG  709

SEQ ID NO: 132   743  AAAATTACTTAATGAAAAAATTCCTTAAATGTTGTGTGTGTAACAAATATTGACG   802

SEQ ID NO: 133   738  AAAATTACTTAATGAAAAAATTCCTTAAATGTTGTGTGTGTAACAAATATTGACG   797

SEQ ID NO: 1     419  GGTACATAGATACCTGCATTTCTGCTTCTTTTAGACGGGGAGCCTTTCAGGCTAAAAAAC  478
                      ||||||||||||||||||||||||||||||||||||||||||||||||||||||||||||
SEQ ID NO: 130   911  GATATATAGATACCTGTATTTCTGCTACTTTTAGAAGGGAGCTTGCCATGCCAAGAAAC  970

SEQ ID NO: 131   710  GGTATATAGACACCTGTATTTCGCATCTTTTAGACGAGAGCTTGCCATGCTAAAAAAC  769

SEQ ID NO: 132   803  GGTATATAGACACCTGTATTTCCGCCCCTTTTCGGCGAGGAGCTGTCATGCTAAAAGAC  862

SEQ ID NO: 133   798  GGTATATAGACACCTGTATTTCTGCCTCCTTTCGGCGAGGAGCCTGTCATGCTAAAAGAC  857
```

| | | | | |
|---|---|---|---|---|
| SEQ ID NO: 1 | 899 | GCAAAAAAAATACACTGTGTTTTATGGCCCACCAAGTACAGGAAAAACAAATTTAGCAA | 958 |
| SEQ ID NO: 130 | 1391 | GTAAGAAAAATACACTGTGTGGTTTTATGGGCCGCCAAGTACAGGAAAAACAAACTTGGCAA | 1450 |
| SEQ ID NO: 131 | 1190 | GTAAAAAAAAACACCCTGTGGTTTTACGGGCCCCCAAGTACTGGAAAAACAAATTTGGCAA | 1249 |
| SEQ ID NO: 132 | 1283 | GTAAAAAAAAACACCCTGTGTGGTTTTACGGGCCACCAAGTACTGGAAAAACAAATTTGGCAA | 1342 |
| SEQ ID NO: 133 | 1278 | GTAAAAAAAATACACTGTGTTGTGTTTTACGGGCCACCAAGTACTGGAAAAACAAATTTGGCTA | 1337 |
| SEQ ID NO: 128 | 99 | GCAAGAAAAATACACTGTGGTTTTATGGGCCGCCAAGTACAGGAAAAACAAACTTGGCAA | 158 |
| SEQ ID NO: 129 | 89 | GTAAAAAAAACACCCTATGGTTTTACGGGCCACCAAGTACTGGAAAAACAAATTTAGCTA | 148 |
| SEQ ID NO: 1 | 959 | TGGCTATTGCTAAAACTGTTCCAGTGTATGGTTAATTGGAATAATGAAAATTTC | 1018 |
| SEQ ID NO: 130 | 1451 | TGGCCATTGCTAAAAGTGTTCCAGTATGGCATGGTTAACTGGAATAATGAAAACTTTC | 1510 |
| SEQ ID NO: 131 | 1250 | TGGCTATTGCTAAAACTGTCCCAGTGTATGGCATGGTTAATGGAATAATGAAAATTTTC | 1309 |
| SEQ ID NO: 132 | 1343 | TGGCTATTGCTAAAACTGTACCAGTGTATGGAATGGTGAATTGGAATAATGAAAACTTTC | 1402 |
| SEQ ID NO: 133 | 1338 | TGGCTATTGCCAAAACTGTCCAGTGTATGGCATGGTTAATTGGAATAATGAAAACTTTC | 1397 |
| SEQ ID NO: 128 | 159 | TGGCTATTGCTAAAACTGTTAACCTGTTAACTGGAATAATGAAAACTTTC | 218 |
| SEQ ID NO: 129 | 149 | TGGCTATTGCTAAAACTGTACCCGTGTATGGAATGGTAACTGGAATAATGAAAACTTTC | 208 |
| SEQ ID NO: 1 | 1019 | CATTTAATGATGTAGCAGGAAAAAGCTTGGTGGTCTGGGATGAGGTATTATTAAGTCTA | 1078 |
| SEQ ID NO: 130 | 1511 | CATTTAATGATGTAGCAGGAAAAAGCTTGGTGGTCTGGGATGAAGGTATTATTAAGTCTA | 1570 |
| SEQ ID NO: 131 | 1310 | CATTTAATGATGTAGCGCAGGAAAAAGTTTGGTGGTCTGGGATGCATTATTAAGTCCA | 1369 |
| SEQ ID NO: 132 | 1403 | CATTTAATGATGTAGCGCAGGAAAAGTTTGGTGGTCTGGGATGAAGGCATTATTAAGTCCA | 1462 |
| SEQ ID NO: 133 | 1398 | CATTTAATGATGTAGCGCAGGAAAAAGTTTGGTGGTCTGGGATGAAGGCATAATAAATCCA | 1457 |
| SEQ ID NO: 128 | 219 | CATTTAATGATGTAGCAGGAAAAAGTTTGGTGGTCTGGGATGAAGGTATTATTAAGTCCA | 278 |
| SEQ ID NO: 129 | 209 | CATTTAATGATGTGGCGGGGAAAAAGTTTGGTGGTCTGGGATGAAGGCATTATTAAGTCCA | 268 |

| SEQ ID NO: 1   | 1439 | AAACCACCCCAATTGTCACAGACCACCAGTGTCAGCAGCAGTGGTGGTGAAAGCTCTGAAG | 1498 |
| SEQ ID NO: 130 | 1931 | AAACCACCCCAATTGTCACAGACCACCAGTATCAGCAGCAGTGGTGGTGAAAGCTCTGAAG | 1990 |
| SEQ ID NO: 131 | 1730 | AAACCGTCCCCATTGTCGCAGACACCCAGTATCAGCAGCAGTGGTGGTGAAAGCTCTGAAG | 1789 |
| SEQ ID NO: 132 | 1823 | AAACCACCCCCATTGTCCCAGACACCAGTATCAGCAGCAGTGGTGGTGAAAGCTCTGAAG | 1882 |
| SEQ ID NO: 133 | 1818 | AAACCACCCCAATTGTCCCAGACACCAGTATCAGCAGCAGTGGTGGTGAAAGCTCTGAAG | 1877 |
| SEQ ID NO: 128 | 639  | AAACCACCCCAATTGTCACAGACACCAGTATCAGCAGCAGTGGTGGTGAAAGCTCTGAAG | 698  |
| SEQ ID NO: 129 | 629  | AAACCACCCCCATTGTCCCAGACACCAGTATCAGCAGCAGTGGTGGTGAAAGCTCTGAAG | 688  |
| SEQ ID NO: 1   | 1499 | AACTCAGTGAAAGCAGCTTTCTCAACCTCATCACCCCAGGCGCCTGGAACACTGAAACCC | 1558 |
| SEQ ID NO: 130 | 1991 | AACTCAGTGAAAGCAGCTTTTTTTTAACCTCATCACCCCAGGCGCCTGGAACACTGAAACCC | 2050 |
| SEQ ID NO: 131 | 1790 | AACTCAGTGAAAGCAGCTTTTTTCAACCTCATCACTCCCAGGCGCCTGGAACAGTGAAACCC | 1849 |
| SEQ ID NO: 132 | 1883 | AACTCAGTGAAAGCAGCTTTTTTCAACCTCATCACTCCAGGCGCCTGGAACAGTGAAACCC | 1942 |
| SEQ ID NO: 133 | 1878 | AACTCAGTGAAAGCAGCTTTTTTCAACCTCATCACTCCAGGCGCCTGGAACAGTGAAACCC | 1937 |
| SEQ ID NO: 126 | 699  | AACTCAGTGAAAGCAGCTTTTTTTAACCTCATCACCCCAGGCGCCTGGAACAGTGAAACCC | 758  |
| SEQ ID NO: 129 | 689  | AACTCAGTGAAAGCAGCTTTTTTCAACCTCATCACTCCAGGCGCCTGGAACAGTGAAACCC | 748  |
| SEQ ID NO: 1   | 1559 | CGCGCTCTAGTACGCCCAGTCCCCGGGACCAGTTCAGGAGGAGAATCATTTGTCGGAAGCTCAA | 1618 |
| SEQ ID NO: 130 | 2051 | CGCGCTCTAGTACGCCCATCCCGTCCCCGGGACCAGTTCAGGAGGAGAATCATTTGTCGGAAGCCCAG | 2110 |
| SEQ ID NO: 131 | 1850 | CGCGCTCTAGTACGCCCGTCCCCGTCCCCGGGACCAGTTCAGGAGGAGAATCATTTGTCGGAAGCCCAG | 1909 |
| SEQ ID NO: 132 | 1943 | CGCGCTCTAGTACGCCCGTCCCCGTCCCCGGGACCAGTTCAGGAGGAGAATCATTTGTCGGAAGCCCAG | 2002 |
| SEQ ID NO: 133 | 1938 | CGCGCTCTAGTACGCCCGTCCCCGTCCCCGGGACCAGTTCAGGAGGAGAATCATTTGTCGGAAGCCCAG | 1997 |
| SEQ ID NO: 128 | 759  | CGCGCTCTAGTACGCCCCATCCCGTCCCCGGGACCAGTTCAGGAGGAGAATCATCTGTCGGAAGCCCAG | 818  |
| SEQ ID NO: 129 | 749  | CGCGCTCTAGTACGCCCGTCCCCGTCCCCGGGACCAGTTCAGGAGGAGAATCATTTGTCGGAAGCCCAG | 808  |

| | | | | |
|---|---|---|---|---|
| SEQ ID NO: 1 | 2519 | GCTCAAGTAGTAAAAGACTACTTTACTTTTAAAAGGTGCAGCTGCCCTGTGCCCATTTT | 2578 |
| SEQ ID NO: 130 | 3011 | GCACAAGCAGTAAAAGACTACTTTACTTTTAAAAGGTGCAGCTGCCCCTGTGCCCATTTT | 3070 |
| SEQ ID NO: 131 | 2810 | GCACAAGCAGTAAAAGATTACTTTACTTTTAAAAGGTGCAGCTGCCCTGTGCCCATTTT | 2869 |
| SEQ ID NO: 132 | 2903 | GCACAAGCAGTAAAAGATTACTTTACTTTTAAAAGGTGCAGCTGCCCTGTGTGCCCATTTT | 2962 |
| SEQ ID NO: 133 | 2898 | GCACAAGCAGTAAAAGATTACTTTACTTTTAAAAGGTGCAGCTGCCCCTGTGTGCCCATTTT | 2957 |
| SEQ ID NO: 1 | 2579 | CAAGGAAGTTTGCCGGAAGTTCCCGCTTACAACGCCTCAGAAAAATACCCAAGCATGACT | 2638 |
| SEQ ID NO: 130 | 3071 | CAAGGAAGTTTGCCGGAAGTTCCCGCTTACAACGCCTCAGAAAAATACCCAAGCATGACT | 3130 |
| SEQ ID NO: 131 | 2870 | CAAGGAAGTTTGCCGGAAGTTCCCGGAAGTTCCCGCATACAACGCCTCAGAAAAGTACCCAAGCATGACT | 2929 |
| SEQ ID NO: 132 | 2963 | CAAGGAAGTTTACCGGAAGTGCCCGCGTACAACGCCTCAGAAAAATACCCCAGCATGACT | 3022 |
| SEQ ID NO: 133 | 2958 | CAAGGAAGTTTACCGGAAGTGCCCGCGTACAACGCCTCAGAAAAATACCCAGCATGACT | 3017 |
| SEQ ID NO: 1 | 2639 | TCAGTTAATTCTGCAGAAGCCAGCACTGGTGCAGGAGGGCGGCAGTAATCCTACTAAA | 2698 |
| SEQ ID NO: 130 | 3131 | TCAGTTAATTCTGCAGAAGCCAGCACTGGTGCAGGAGGGCAGTAATTCTGTCAAA | 3190 |
| SEQ ID NO: 131 | 2930 | TCAGTTAATTCTGCAGAAGCCAGCACTGGTGCAGGAGGCAGTAATCCTGTCAAA | 2989 |
| SEQ ID NO: 132 | 3023 | TCAGTTAACTCTGCAGAAGCCAGCACTGGTGCAGGCGGGGTAGCAACCTACAAAA | 3082 |
| SEQ ID NO: 133 | 3018 | TCAGTTAACTCTGCAGAAGCCAGCACTGGTGCAGGCGGGGAGCAACCCTACAAAA | 3077 |
| SEQ ID NO: 1 | 2699 | AGCATGTGGAGTGAGGGGCTACTTTACTGCCAACTCTGTGTAACTTGTACATTTTCCAGA | 2758 |
| SEQ ID NO: 130 | 3191 | AGCATGTGGAGTGAGGGGCCACTTTTTAGTCTAACTGCTAACTCTGTAACTTGTACATTTTCCAGA | 3250 |
| SEQ ID NO: 131 | 2990 | AGCATGTGGAGTGAGGGGCCACTTTTACTGCCAACTCTGTAACTCTGTACATTTTCCAGA | 3049 |
| SEQ ID NO: 132 | 3083 | AGCATGTGGAGTGAAGGGGGCTACATTTACTGCTAATTCTGTAACGTGTACATTCTCTAGG | 3142 |
| SEQ ID NO: 133 | 3078 | AGCATGTGGAGTGAAGGGGCTACATTTACTGCTAATTCTGTAACATGCACATTCTCTAGG | 3137 |

FIG. 4N

```
SEQ ID NO: 1    2759  CAGTTTTTAATTCCCATATGATCCAGAGCACCATTATAAAGTGTTTCTCCCCGCAGCCAGT  2818
                      ||||||||||||||||||||||||||||||||||||||||||||||||||||||||||||
SEQ ID NO: 130  3251  CAGTTTTTAATTCCATATGACCCAGAGCACCATTATAAAGTGTTTCTCCCGCAGCGAGT   3310
                      |||||||||||| ||||||| ||||||||||||||||||||||||||||| ||||| ||
SEQ ID NO: 131  3050  CAGTTTTTAATTCCATATGACCCAGAGCACCATTATAAAGTGTTTCTCCCCGCAGCTAGT  3109
                      |||||||||||| |||||||||||||||||||||||||||||||||||||||||| |||
SEQ ID NO: 132  3143  CAATTTTTAATTCCATATGATCCAGAGCATCATTATAAAGTGTTCTCCAGCAGCAGCTAGT 3202
                      || |||||||||||||||||||||||||| ||||||||||| ||||||| ||||| |||
SEQ ID NO: 133  3138  CAGTTTTTAATTCCATATGATCCAGAGCATCATTATAAAGTATTTTCTCCAGCAGCCAGT  3197
                      |||||||||||||||||||||||||||||| ||||||||| ||| ||||| |||||||

SEQ ID NO: 1    2819  AGCTGCCACAATGCCAGTGGAAAAGAGGCAAAAGTTTGCACCATTAGTCCCATAATGGGA  2878
                      ||||||||||||||||||||||||||||||||||||||||||||||||||||||||||||
SEQ ID NO: 130  3311  AGCTGCCACAATGCCAGTGGAAAAGAGGCAAAAGTTTGCACCATCCCATAATGGGA     3370
                      |||||||||||||||||||||||||||||||||||||||||||  ||||||||||||
SEQ ID NO: 131  3110  AGCTGCCATAATGCCAGTGGAGAGAGGCAAAAGTTTGCACTATTAGTCCCATAATGGGC   3169
                      |||||||| |||||||||||| ||||||||||||||||||| |||||||||||||| 
SEQ ID NO: 132  3203  AGCTGCCACAATGCTAGTAGTGGAGAGAGGCAAAAGTGTGCACTATTAGTCCCATTATGGGG 3262
                      ||||||||||||| ||| ||| |||||||||||||| ||||| ||||||||||| |||| 
SEQ ID NO: 133  3198  AGCTGCCACAATGCTAGTAGTGGAGAGAGGCAAAAGTGTGCACTATTAGTCCTATTATGGGA 3257
                      ||||||||||||| ||| ||| |||||||||||||| ||||| ||||||||  |||||||

SEQ ID NO: 1    2879  TACTCCACACCATGGAGATACTTAGATTTTAATGCTTTAAATTATTTTTTCACCTTTA   2938
                      |||||||||||||||||||||||||||||||||||||||||||||||||||||||||
SEQ ID NO: 130  3371  TACTCAACCCCATGGAGATATTTAGATTTTAAATTATTTTAATTTTTTCACCTTTA     3430
                      |||||  ||||||||||||| ||||||||||| ||||| ||||| |||||||||||
SEQ ID NO: 131  3170  TACTCAACGCCATGGAGATACTTAGACTTAAATGCTTAACTATATTTTTCACCCTTTA    3229
                      ||||| || |||||||||| |||||| |||||||| || ||| ||||||||| ||||
SEQ ID NO: 132  3263  TACTCTACTCCGTGGAGATACTTAGATTTTAATGCTTTAAATTTGTTTTTCTCCACATTA  3322
                      |||| ||| || |||||||||||||||||||||||| ||| | ||||||| |||| |||
SEQ ID NO: 133  3258  TACTCTACTCCGTGGAGATACTTAGATTTTAATGCTTTAAATTTGTTTTTTGAATTTTCACCACTA 3317
                      |||| ||| || |||||||||||||||||||||||| ||| | ||| |  ||| ||||||

SEQ ID NO: 1    2939  GAGTTTCAACATTTAATTGAGAATTATGGAAGTATAGCTCCTGATGCTTAACTGTTGCC  2998
                      ||||||||||||||||||||||||||||||||||||||||||||||||||||||||||
SEQ ID NO: 130  3431  GAGTTTCAGCACTTAATTGAAAATTATGGAAGTATAGCTCCTGATGCTTAACCTGTAACC  3490
                      ||||||||||| ||||||||| ||||||||||||||||| ||||||||||| ||| ||
SEQ ID NO: 131  3230  GAATTTCAACATTTAATTGAAAATTATGGAAGTATAGCCCCTGATGCTTAACTGTTACC   3289
                      || |||||||||||||||||| |||||||||||||||| ||||||||||| ||| ||
SEQ ID NO: 132  3323  GAGTTTCAGCACTTAATTGAAATTATGGTAGTATAGCTCCAGATGCTTAACTGTAACT    3382
                      ||||||||||| ||||||||||  ||||| ||||||| || ||||||||| ||| ||
SEQ ID NO: 133  3318  GAGTTTCAGCACTTAATTGAGAATTATGGCAGTATAGCTCCAGATGCTTAACTGTAACT  3377
                      ||||||||||| ||||||||| |||||||  |||||| || |||||||| ||| ||
```

```
SEQ ID NO: 1    3239  AAATTAGCTAGTGAAGAATCAGCGTTTTATGTCCTGGAACACAGCTCTTTTGAACTTTTA  3298
SEQ ID NO: 130  3731  AAATTAGCAAGTGAAGAATCAGCAGTTTATGTTTTTGGAACACAGTTCTTTTCAGCTTTTA  3790
SEQ ID NO: 131  3530  AAGCTAGCAAGTGAAGAATCAGCAGCATTTTATGTTTGGAACACAGTTCATTTGAACTGTTA  3589
SEQ ID NO: 132  3623  AAATTGGCTAGTGAAGAATCAGCGTTTTTATGTGTTAGAGCACAGTTCATTTGAACTTTTG  3682
SEQ ID NO: 133  3618  AAATTGGCTAGTGAAGAATCAGCGTTTTATGTTTTGGAACACAGCTCCTTTCAACTTTTA  3677

SEQ ID NO: 1    3299  GGTACAGGGGCTCTGCTACTATGTCTTATAAGTTCCCTCCAGTGCCCCCAGAGAATTTA  3358
SEQ ID NO: 130  3791  GGTACAGGAGGAGGTACAGCATCTATGTCCTATAAGTTCCTTCCAGTGCCCCAGAAAATTA  3850
SEQ ID NO: 131  3590  GGTACAGGTGGCTCTGCCACTAGTCCATTTTATGTCCTATAAATTCCACCAGTGCCCCAGAAAACTTG  3649
SEQ ID NO: 132  3683  GGTACAGGGGATCTGCCACTATGTCCTACAAATTTCCAGCTGTGCCCCAGAAAACCTA  3742
SEQ ID NO: 133  3678  GGTACAGGTGGCTCTGCTACAAGTCCTATAAATTTCCAGCCGTGCCCCAGAAAACTTA  3737

SEQ ID NO: 1    3359  GAAGGCTGTAGTCAACACTTTTATGAAATGTACAACCCGTTATATGGATCCCGTTTAGGA  3418
SEQ ID NO: 130  3851  GAGGGCTGCAGTGCCAACACTTTTATGAAATGTACAATCCCTTATACGGATCCCGCTTAGGG  3910
SEQ ID NO: 131  3650  GAGGGTTGTAGCCAACATTTTTATGAAATGTACAAACCCCTGTATGGGTCTCGTTTTAGGG  3709
SEQ ID NO: 132  3743  GAAGGCTGCAGCCAACAATTTTATGAAATGTACAACCCTTGTACGGTTCTCGTTTAGGG  3802
SEQ ID NO: 133  3738  GAGGGCTGCAGTCAGCATTTTTATGAAATGTACAAACCCCGTGTATGGTTCTCGTTTAGGA  3797

SEQ ID NO: 1    3419  GTCCCTGATACATTAGGAGGGGACCCCAAATTTAGATCTTTAACACATGAAGACCACGCA  3478
SEQ ID NO: 130  3911  GTTCCTGACACATTAGGAGGTGACCCCAAAATTTAGATCTTTAACACATGAAGACCATGCA  3970
SEQ ID NO: 131  3710  GTACCTGACACATTAGGGGGGACCCTAAATTTAGATCATTAGATCACGAAGATCATGCA  3769
SEQ ID NO: 132  3803  GTACCTGACACATTAGGAGGGGACCCCTAAATTTAGATCATTGACACACGAAGACCACGCA  3862
SEQ ID NO: 133  3798  GTGCCTGACACATTAGGAGGGGACCCTAAATTTAGATCATTAACACACGAGGACCACGCA  3857
```

FIG. 4Q

```
SEQ ID NO: 1     3479  GTTCAGCCACAAAATTTATGCCAGGGCCACTGGTAACTCAGTTTCCACAAAGGAGGGA  3538
                       ||||||||||||||||||||||||||||||||||||||||||||||||||||||||||
SEQ ID NO: 130   3971  ATTCAGCCCCAAAAACTTCATGCCAGGGCCACTAGTAAACTCAGTGTCTACAAAGGAGGGA  4030

SEQ ID NO: 131   3770  ATTCAGCCACAAAAACTTTATGCCTGGCCACTAGTAAACTCAGTGTCCACTAAGAGGGA  3829
                       ||||||||||||||||||||||||||||||||||||||||||||||||||||||||||
SEQ ID NO: 132   3863  ATTCAGCCACAAAAACTTTATGCCTGGGCCACTAGTAAATTCAGTGTCTACCAAAGAAGGA  3922

SEQ ID NO: 133   3858  ATTCAGCCACAAAAACTTTATGCCTGGGCCACTGCTGATTAACTCAGTGTCTACCAAAGAAGGA  3917

SEQ ID NO: 1     3539  GACAGTTCTAACACAGGAGCGGGAAAAGCCCTAACACAGGCCTTAGCACAGGCACTAGTCAA  3598
                       ||||||||||||||||||||||||||||||||||||||||||||||||||||||||||
SEQ ID NO: 130   4031  GACAGCTCTAATACTGGAGCTGGAAAAGCCTTAACACAGGCCTTAGCACAGGCACTACCTCTCAA  4090

SEQ ID NO: 131   3830  GACACTTCCAATACAGGCGCCGGAAAAGCCCTTACGGGGCTTAGTACTGGCACTAGTCAA  3889

SEQ ID NO: 132   3923  GACAATTCTAATACAGGTGCTGGAAAAGCCCTTACGGGGCTTAGTACTGGCACTAGTCAA  3982

SEQ ID NO: 133   3918  GACACCTCTAATACAGGTGCTGGAAAAGCCCTTACGGGGCTTAGTACTGGCACTAGTCAA  3977

SEQ ID NO: 1     3599  AGTACTAGAATATCATTACGCCCTGGTCTCCAGTGTCTCAACCATATCACCACTGGGACACA  3658
                       ||||||||||||||||||||||||||||||||||||||||||||||||||||||||||
SEQ ID NO: 130   4091  AACACTAGAATATCCTTACGCCCAGTGCCCTGGGCCACAGTGTCTCAGCCTCAGCCACACTGGGACACA  4150

SEQ ID NO: 131   3890  AGCCACCAGAATATCCCTGCCCTGGCCCCAGGACCAGTGTCTCAGCCATTACTGGGACACT  3949

SEQ ID NO: 132   3983  AACACCAGAATTTCCCTACGCCCCGGCGGCCCAGTGTCTCAGCCATATCTCAGCCATCACTGGGACACT  4042

SEQ ID NO: 133   3978  AGCACCAGAATTTCCCTGCCCCCCGCCCCAGTGTCCCAGTGTCTCAGCCATACCATCACTGGGACACT  4037

SEQ ID NO: 1     3659  GATAAATATGTAACAGGATAAAATGCCATTTCTCATGGTCAAACCACTTATGGCAATGCT  3718
                       ||||||||||||||||||||||||||||||||||||||||||||||||||||||||||
SEQ ID NO: 130   4151  GATAAATATGTCACAGGAATAAATGCCATTTCTCATGGTCATGTCAGACAAAACCACTTATGGTAACGCT  4210

SEQ ID NO: 131   3950  GATAAGTATGTCACAGGAATAAATGCTATTTCACACGGACAAAACCACTTATGGAAATGCT  4009

SEQ ID NO: 132   4043  GATAAATATGTTACAGGAATAAATGCCATTTCACATGGACAAACCACTTATGGAAATGCT  4102

SEQ ID NO: 133   4038  GATAAATATGTAACAGGAATAAATGCCATCTCACATGGACAAAACCACTTATGGAAATGCT  4097
```

FIG. 4R

```
SEQ ID NO:   1   3719  GAAGACAAAGAGTATCAACAGGGCGTGGGTAGGTTTCCCAATGAAAAAGAACAACTAAAA  3778
                       ||||| ||||||||||||||||| ||||||||||| ||||||||||||||||||||||||
SEQ ID NO: 130   4211  GAAGACAAAGAGTATCAGCAAGGGCAAGGAGTAGGTAGATTTCCAAATGAAAAAGAACAACAGCTAAAA  4270
                       ||||| ||||||||||||||||| ||||||||||| ||||||||||||||||||||||||
SEQ ID NO: 131   4010  GAAGACAAAGAGTATCAGCAAGGGCAAGGGGTAGGAAGATTCCAAATGAAAAAGAGCAACTTAAA  4069
                       ||||| ||||||||||||||||| |||||||| || ||||||||||||||||| ||||| |||
SEQ ID NO: 132   4103  GAGGACAAAGAGTATCAGCAAGGGCAAGGGGTAGGAAGATTTCCAAATGAAAAAGAACAGCTTAAG  4162
                       || || ||||||||||||||||| |||||||| || |||||||||||||||||||||| |||||
SEQ ID NO: 133   4098  GAAGACAAAGAGTATCAGCAAGGGCAAGGGGTAGGAAGGTTTCCAAATGAAAAAGAACAACTTAAG  4157

SEQ ID NO:   1   3779  CAGTTACAGGGTTTAAATATACACATATTTCCCAATAAAGGTACCCAGCAATATACA  3838
                       |||||||| |||||||| ||  ||||  ||| ||||||||||||||||||||||||
SEQ ID NO: 130   4271  CAGTTACAGGGTTTAAACATGCACCTACTTCCCAATAAAGGAACCCAGCAATATACA  4330
                       |||||||| |||| ||| || |||| || ||||||| || ||| ||||||||||||
SEQ ID NO: 131   4070  CAGTTACAAGGCCTAAACATTCACACATACTTCCAAACAAAGGAACCCAACACACA  4129
                       |||||||| || |||||| | ||| ||||| |||  ||||| |||||| ||||||
SEQ ID NO: 132   4163  CAGTTACAAGGTCTAAACATGCACACATACTTCCCTAATAAAGGAACCCAACAATACACA  4222
                       |||||||| || |||||| | ||| ||||| ||| ||||||| |||||| ||||||||
SEQ ID NO: 133   4158  CAGTTACAAGGCTAAACATGCACACATACTTCCTAATAAAGGTACCCAACAATACACA  4217

SEQ ID NO:   1   3839  GATCAAATTGAGCGGCCCCCCTAATGGTCTGTATGGAACAGAGAGCCCTTCACTAT  3898
                       ||||||| ||||| ||| ||| ||||||| ||| |||||| || ||||| |||||
SEQ ID NO: 130   4331  GATCAAATTGAACGCGCCCCCCTAATGGTCTGTATTGGAACAGAAGAGCCCTTCACTAT  4390
                       |||||||||||| || || ||| ||||||| |||| |||||| ||||| ||||||||
SEQ ID NO: 131   4130  GATCAAATTGAACGCCCCTAATGGTCTGTGGGAACAGAGAGCTCTTCATTAT  4189
                       ||| ||||||| || || ||| |||||| ||| ||||| |||||| ||||
SEQ ID NO: 132   4223  GACCAAATTGAACGCCCTCTTATGGTGGGCTCGTTTGGAACAGAAGAGCTCTTCACTAT  4282
                       || |||||||| || || | ||| |||| ||||| |||||| ||||| |||||||||
SEQ ID NO: 133   4218  GATCAAATTGAAAGACTTTAATGGTGGGCTCGTGTGGAACAGAAGAGCTCTTCACTAT  4277

SEQ ID NO:   1   3899  GAAAAGCCAGCTGTGGAGTAAAATACCAAAATTAGATGACAGCTTTAAAACTCAGTTTGCA  3958
                       |||| |||||||||||||| ||| ||||| ||||||| |||||||||||||||||||||
SEQ ID NO: 130   4391  GAAAGCCAGCTGTGGAGTAAAATTCCAAATTAGATGACAGTTTAAAACTCAGTTTGCA  4450
                       |||| ||||||||||||| ||| |||||| ||||| |||| |||||||||||||||
SEQ ID NO: 131   4190  GAGAGTCAGCTGTGGAGTAAATCCCCAACTAGATGACAGTTTTAAAACCCAATTTGCA  4249
                       || || ||||||||||||||| || ||| |||||||||| ||||||| ||||||||
SEQ ID NO: 132   4283  GAAAGTCAGCTGTGGAGTAAATCCCTAACTTAGATGACAGTTTTAAAACTCAATTTGCA  4342
                       || || |||||||||||||||| ||||| |||||||||| |||||||| ||||||||
SEQ ID NO: 133   4278  GAAAGTCAGTTATGGAGTAAAATCCCTAACTTAGATGATAGTTTTAAAACTCAATTTGCA  4337
```

| | | | |
|---|---|---|---|
| SEQ ID NO: 1 | 4199 | TATGACCCCCACAGCTACAGATGCAAAGCAACACCACAGACATGGATATGAAAAGCCTGAA | 4258 |
| SEQ ID NO: 130 | 4691 | TATGACCCCACAGCTACAGATGCAAAGCAAAACAACACCACAGACATGGATATGAAAAGCCTGAA | 4750 |
| SEQ ID NO: 131 | 4490 | TATGACCCTACAGCTACAGATGCAAAGCAAAACAACACCACAGACATGGATATGAAAAGCCTGAA | 4549 |
| SEQ ID NO: 132 | 4583 | TATGACCCCCACAGCTACAGATGCAAAGCAACACCACAGACACGGATATGAAAAGCCTGAA | 4642 |
| SEQ ID NO: 133 | 4578 | TATGACCCCCACAGCTACAGATGCAAAGCAACACCACAGACACGGATATGAAAAGCCTGAA | 4637 |
| SEQ ID NO: 1 | 4259 | GAATTGTGGAC | 4269 |
| SEQ ID NO: 130 | 4751 | GAATTGTGGACA | 4762 |
| SEQ ID NO: 131 | 4550 | GAATTGTGGAC | 4560 |
| SEQ ID NO: 132 | 4643 | GAATTGTGGACT | 4654 |
| SEQ ID NO: 133 | 4638 | GAATTGTGGACT | 4649 |

```
PVBAUA    (3226)  CTCTGTAACTTGTACATTTCCAGACAGTTTTTAATTCCATATGACCCAGAGCACCATTATAAGGTGTTTCTCCGCAGCGAGTAGCTG
Consensus (3421)  -TCTGTAAC-TG-ACATT-TC-AG-CA-TTTTAAT-CC-TATGA-CCAGAGCA-CATTATAA-GT-TT-TCTCC-GCAGC-AG-AG-TG PVBAUA    (3316)  CCACAATGCCAGTGGAAAGGAGGCAAAGGTTTGCACCATCAGTCCCATAATGGGATATCCAACCCATGGAGATATTTAGATTTAATG
Consensus (3511)  CCA-AATGC-AGTGG-AA-GAGGCAAA-GT-TGCAC-ATTAG-CC-AT-ATGGG-TACTC-AC-CC-TGG-GATA-TTAGA-TTTAATG PVBAUA    (3405)  CTTTAAATTTATTTTTTCACCTTTAGAGTTTCAGCACTTAATTGAAAATTATGAAGTATAGCTCCTGATGCTTTAACTGTAACCATAT
Consensus (3601)  C--TT-AA-TT--TTTT--T-CACC--TAGA-TTTCA-CA-TTAATTGA-AA-TATGG-AG-ATAGC-CC-GATGCTTTAACTGT-AC-AT-T PVBAUA    (3495)  CAGAAAATTGCTGTTAAGGATGTTACAGACAAAACTGGAGGGGGGTACAGGTTACTGACAGCACTACAGGGGCTATGCATGTTAGTAG
Consensus (3691)  CAGAAAATTGCTGT-AA-GA-GT-ACAGA-CAAAAC-GGAGG-GG-GT-CA-GT-ACTGACAG-AC-AC-GG--CG--T-TG-ATGTTAGT-G PVBAUA    (3585)  ACCATGAATACAAGTACCCATATGTGTTAGGGCAAGGTCAGGATACTTTAGGCCCCAGAACTTTCCTATTTGGGTATACTTTCCCTCAAT
Consensus (3781)  A--CATGA-TA-AA-TA--CCATATGTG--T-GG-CA-GG-CA-GA-AC--TAGC--CCAGAACT--CC-ATTTGGGT-TACTTTCC--CC-CA-T PVBAUA    (3675)  ATGCTTACTTAACATAGGAGATGTTAACACAAGGAATTCTGGAGACAGCAGCAAAAAATTAGCAAGTGAAGAATCAGCATTTTATGTTT
Consensus (3871)  ATGCTTA--TT-ACAGT-GG-GA-GT-AACACACA-GG---T-TC-GG-GACAG-AAAAAA-T-GC-AGTGAAGAATCAGC-TTTTATGT--

PVBAUA    (3765)  TGGAACACAGTCTCTTTCAGCTTTTAGGTACAGGAGGTACAGCATCTATGTCTTATAAGTTCCTCCAGTGCCCCAGAAAAATTAGAGG
Consensus (3961)  T-GA-CACAG-TC-TTT-A-CT--T-GG-ACAGG-GG--C-GC-A--ATGTC-TA-AA-TTTCC--C-GT-CC-CCAGAAAA--T-GA-G PVBAUA    (3855)  GCTGCAGTCAACACTTTTATGAAATGTACAATCCCTTATACGGATCCGGCTTAGGGGTTCCTGACACATTAGGAGGTGACCAAAATTA
Consensus (4051)  G-TG-AG-CA-CA-CA-TTTATGA-ATGTACAA--CC--T--TA-GG-TC-CG-TTAGG-GT-CCTGACACA-TAGG-GG-GACCC-AAATT-A PVBAUA    (3945)  GATCTTTAACACATGAAGACCATGCAATTCAGCCAAAACTTCATGCCAGGGCCACTAGTAAACTCAGTCGTCTACAAAGGAGGAGACA
Consensus (4141)  GATC--T--AC-GA-GA-CA-GA-CAATTCAGCC--CA-AA-TT-ATGCC-GG--CCACT--T-AA-TCAGT-TC-AC-AA-GA-GGAGA-A PVBAUA    (4035)  GCTTCTAATTACTGGAGCTGGAAAAGCTTAACAGGCCTTAGCACAGGTACCTCTCAAAACACTAGAATATCCTTACGCCCTGGCCAGTGT
Consensus (4231)  --TC-A-TAC-GG-GC-GG-AAAGC-T-AC-GG-CTTAG-AC-GG-AC----CAAA--AC-AGAAT-TCC-T-CGCCC--GG-CCAGT-T PVBAUA    (4125)  CTTAGCCATACCACCACTGGGACACAGAGATAAATATGTCAGGAATAAATGCCATTTCTCATGGTCAGACCACTATGGTAACGCTGAAG
Consensus (4321)  C--CAGCC-TA-CA-CACTGGGACAC-GATAA-TATGT-ACAGGA-TA-GC-ATTTC-CA-GG-CA-AC-AC-TATGG-AA-GCTGA-G PVBAUA    (4215)  ACAAAGAGTATCAGCAAGGAGTGGGTAGATTTCCAAATGAAAAAGAAACAGCTAAAACATGCACACCTACTTTC
Consensus (4411)  A-AA-GA-TATCAGCAAGG-GT-GG--AG--TT-CC-AATGAAAAAAGA-CA-CT-AA-CAGTT--CA-GG--T-AACAT-CACAC-TA-TT-C
```

| Target Region | Function | Name | SEQ ID NO: | Sequence | Tm |
|---|---|---|---|---|---|
| 1 | Forward primer | B19_2043F | 136 | TGAAACCCGGCTCTA | 59.6 |
| | Reverse primer | B19_2171R | 137 | AACTAACAGTTCACGAAACTG | 56.7 |
| | Detection probe | B19_2069F_FAM | 138 | TCCCCGGGACCAGTTCAGGAGAA | 68.1 |
| 2 | Forward primer | B19_1962F | 139 | TCAGCAGCAGTGGTGGT | 59.6 |
| | Reverse primer | B19_2043R | 140 | TAGAGCGCGGGGTTTCA | 59.6 |
| | Detection probe | B19_1979F-FAM | 141 | TGAAAGCTCTGAAGAACTCAGTGAAAGCAGCTTT | 67.0 |
| | Forward primer | B19_1903F | 142 | AATGCAGATGCCCTCCAC | 59.9 |
| | Detection probe | B19_1962F-FAM | 143 | TCAGCAGCAGTGGTGGTGAAAGCTCTGAA | 68.9 |
| | Reverse primer | B19_2027R | 144 | TGTTCCAGCGCCTG | 58.9 |
| 3 | Forward primer | B19_4700F | 145 | CACAGCTACAGATGCAAA | 55.3 |
| | Reverse primer | B19_4769R | 146 | GGTGCACACGGCTTTT | 56.7 |
| | Detection probe | B19_4733R_FAM | 147 | TGTCCACAATTCTTCAGGCTTTTCATATCC | 64.6 |
| | Detection probe | B19_4733F_FAM | 148 | TGGATATGAAAAGCTGAAGTATTGTGGAC | 64.6 |
| | Forward primer | B19_4672F | 149 | GGTCATTTACCATATGTACT | 54.2 |
| | Detection probe | B19_4703F-FAM | 150 | AGCTACAGATGCAAA5NlCAACACCACAGACA | 66.7 |
| 4 | Forward primer | B19_1500F | 151 | GAAAACTTTCCATTTAATGATGT | 53.8 |
| | Reverse primer | B19_1631R | 152 | ATTTTTGATCTACCCTGGT | 54.2 |
| | Detection probe | B19_1537F-FAM | 153 | TTGGTGTCTGGGATGAAGG | 62.4 |
| 5 | Forward primer | B19_1411F | 154 | GTTTTATGGGCCGCCAAGTA | 60.4 |
| | Reverse primer | B19_1537R | 155 | TTCATCCCAGACCACCAAGG | 62.4 |
| | Detection probe | B19_1450F-FAM | 156 | ATGGCTATTGCTAAAACTGTTCCAGTGTA | 63.2 |
| | Detection probe | B19_1492F-FAM | 157 | TGGAATAATGAAAACTTTCCATTTAATGATGTAG | 61.0 |
| | Detection probe | B19_1448F-FAM | 158 | CAATGGCCATTGCTAAAAGTGTTCCA | 63.0 |

FIG. 10

SEQUENCE LISTING

<160> NUMBER OF SEQ ID NOS: 162

<210> SEQ ID NO 1
<211> LENGTH: 4778
<212> TYPE: DNA
<213> ORGANISM: Erythrovirus B19

<400> SEQUENCE: 1

```
cagctctttc ttttggggtt gcttttacct ggacttttct tgctgtcttt tgcgtgctaa      60
ctaacaggta tttatactac ttgttaactt actaacatgg agttatttag agggggtgatt     120 caagtttctt ctaacattct tgactgtgct aacgataact ggtggtgctc tatgctggat     180
ttagacactt ctgactggga accattaact cattctaaca gactaatggc aatatattta     240
```

```
agcagcgtgg cttctaagct tgactttaca gggggggccct tagctgggtg cttgtactttt    300 tttcaggtgg aatgtaacaa atttgaggaa ggctatcata tccatgtggt tattggggga    360
ccagggctaa accctagaaa cctaacagtg tgtgtagagg gattatttaa taatgtactt    420
taccaccttg taactgaaaa tgtaaagctt aaatttttac caggaatgac tacaaaaggc    480
aaatatttta gagatggaga acaatttata gaaaattatt taatgaaaaa aataccttta    540
aatgttgtat ggtgtgtaac caatattgat gggtacatag atacctgcat ttctgcttct    600
tttagacggg gagcctttca ggctaaaaaa ccccgcatta gtgcaaacac tgatgggggt    660
tctaatgaac caggggaatc tagcgctaca ggggagatg ttgtgccatt tgctgggaag    720
gggactaaag ctggaataaa atttcaaact atggtaaatt ggttgtgtga aaatagggtt    780
tttacagagg ataagtggaa actagttgac tttaaccagt acactttact tagcagtagt    840
cacagtggga gctttcaaat acaaagtgca ttaaaactag ctatttataa ggctaccaat    900
ttagtgccta caagtacatt tttgttacac acagactttg agcaggctaa ctgtattaaa    960
gaaaataaaa tagttaaact gttactgtgt caaaattatg acccсcttgtt ggtgggacag    1020 catgtgttaa agtggattga taaaaaatgt ggcaaaaaaa atacactgtg gttttatggc    1080
ccaccaagta caggaaaaac aaatttagca atggctattg ctaaaactgt tccagtgtat    1140
ggtatggtta attggaataa tgaaaatttt ccatttaatg atgtagcagg aaaaagcttg    1200
gtggtctggg atgagggtat tattaagtct actattgtag aagctgcaaa agccatttta    1260
ggagggcaac caaccagggt agatcaaaaa atgcgtggaa gtgtagcagt gcctggagta    1320
ccagtggtaa taaccagcaa tggtgacatt acttttgttg ttagtgggaa cactacaaca    1380
actgtccatg ctaaagcctt aaaggagcga atggtaaagt taaactttac cataagatgt    1440
agccctgaca tgggcttact tacagaggct gacgtgcagc aatggcttac atggtgtaat    1500
gcacaaagct ggagccacta tgaaaactgg gcaataaact cactttttga tttccctgga    1560
ataaatgcag atgccctcca cccagacctc caaaccaccc caattgtcac agacaccagt    1620
gtcagcagca gtggtggtga aagctctgaa gaactcagtg aaagcagctt tctcaacctc    1680
atcaccccag gcgcctggaa cactgaaacc ccgcgctcta gtacgccagt ccccgggacc    1740
agttcaggag aatcatttgt cggaagctca atttcctccg aagctgtagc tgcatcgtgg    1800
gaagaagcct tctacacacc tttggcagat cagtttcgtg aactgttagt tggggttgac    1860
tatgtatggg atggtataag gggtttacct gtttgttgtg tgcaacatat taataacagt    1920
gggggaggct tgggattttg tccccattgc attaatgtgg gggcttggta taatggatgg    1980
aagtttcgag aatttacccc agatttggtg cggtgtagct gtcatgtagg agcttctaat    2040 ccttttttctg tgttaacctg caaaaaatgt gcttacctat ctggcttgca aagttttgta    2100
gattatgagt aaagaaattg gtaaatggtg ggaaagtgat gataaatttg ctaaggacgt    2160
gtataagcaa tttgtagaat tttatgaaaa agttactgga acagacttag agcttattca    2220
aatattaaaa gatcattaca atatttcttt agataatcct ctagaaaacc catcttcttt    2280
gtttgactta gtggctcgta ttaaaagtaa ccttaaaaac tctccagact tatatagtca    2340
tcattttcaa agtcatggac agttatctga ccacccccat gccttatcat ccagtaacag    2400
tgatgcagaa cctagaggag aaaatgcagt attatctagt gaagacttac acaagcctgg    2460
gcaagttagc atacaactac ccggtactaa ctatgttggg cctggcaatg agctacaagc    2520 tgggccccccg cagagtgctg tggacagtgc tgcaaggatt catgacttta ggtatagcca    2580
```

-continued

```
actggctaag ctgggaataa atccatatac tcattggact gtagcagatg aggagctgtt    2640
aaaaaatata aaaaatgaaa ctgggtttca agctcaagta gtaaaagact actttacttt    2700
aaaaggtgca gctgccctg tggcccattt tcaaggaagt ttgccggaag ttcccgctta    2760
caacgcctca gaaaaatacc caagcatgac ttcagttaat tctgcagaag ccagcactgg    2820
tgcaggaggg ggcggcagta atcctactaa aagcatgtgg agtgaggggg ctacttttac    2880
tgccaactct gtaacttgta cattttccag acagtttta atcccatatg atccagagca    2940
ccattataaa gtgttttctc ccgcagccag tagctgccac aatgccagtg aaaagaggc    3000 aaaagtttgc accattagtc ccataatggg atactccaca ccatggagat acttagattt    3060 taatgctta aatttatttt tttcaccttt agagtttcaa catttaattg agaattatgg    3120
aagtatagct cctgatgctt taactgttgc catatcagaa attgccatta aagatgttac    3180
agacaaaact ggaggagggg tacaggttac tgacagtact acagggcgtt tatgcatgtt    3240
agtagaccat gaatacaagt acccatatgt attaggtcaa ggacaagata ccttagcccc    3300
agagcttcca atttgggtgt actttccacc tcaatatgct tacttaacag taggagatgt    3360
aaacacgcag gaatttctg gggacagtaa aaaattagct agtgaagaat cagcgtttta    3420
tgtcctggaa cacagctctt ttgaactttt aggtacaggg ggctctgcta ctatgtctta    3480
taagttccct ccagtgcccc cagagaattt agaaggctgt agtcaacact tttatgaaat    3540
gtacaacccg ttatatggat cccgtttagg agtccctgat acattaggag gggaccccaa    3600
atttagatct ttaacacatg aagaccacgc agttcagcca caaaatttta tgccagggcc    3660
actggtaaac tcagttttcca caaaggaggg agacagttct aacacaggag cgggaaaagc    3720
cctaacaggc cttagcacag gcactagtca aagtactaga atatcattac gccctggtcc    3780
agtgtctcaa ccatatcacc actgggacac agataaatat gtaacaggga taatgccat    3840 ttctcatggt caaaccactt atggcaatgc tgaagacaaa gagtatcaac agggcgtggg    3900
taggtttccc aatgaaaaag aacaactaaa acagttacag ggtttaaata tacacacata    3960 ttttccaat aaaggtaccc agcaatatac agatcaaatt gagcgcccc taatggtagg    4020 ctctgtatgg aacagaagag cccttcacta tgaaagccag ctgtggagta aaataccaaa    4080
tttagatgac agctttaaaa ctcagtttgc agctttagga ggttggggac tacatcagcc    4140 acccctcaa atattttaa aaatattacc acaaagtggg ccaattgggg gtattaagtc    4200
aatgggaata acaacattag ttcaatatgc tgtgggtatt atgacagtaa ctatgacatt    4260
taaattaggg cctcgcaaag ctacaggacg gtggaatcct caacctggag tgtaccctcc    4320
tcacgcagca ggccatttac catatgtact atatgacccc acagctacag atgcaaagca    4380
acaccacaga catggatatg aaaagcctga agaattgtgg actgccaaaa gccgtgtgca    4440
cccattgtaa acactcccca ccgtgccctc agccaggatg tgtaactaaa cgcccaccag    4500
tgccacctag actgtattta ccccccctg tacctataag acagcctacc acaaaagaca    4560
cagacaatgt agagtttaaa tacttaagcc gctatgaaca acatgtaatt agaatgttaa    4620
gattgtgtaa tatgtataaa aatttagaaa aataaacact tgttgcagtt aataaattgc    4680
gtatgttgtg ttttaaaaat ttaaaagaag acaccaaatc agatgccgcc ggtcgccgcc    4740
ggtaggcggg acttccggta caagatggcg gaaattca                            4778
```

<210> SEQ ID NO 2
<211> LENGTH: 18
<212> TYPE: DNA
<213> ORGANISM: Erythrovirus B19

-continued

```
<400> SEQUENCE: 2
gataactggt ggtgctct                                                 18

<210> SEQ ID NO 3
<211> LENGTH: 14
<212> TYPE: DNA
<213> ORGANISM: Erythrovirus B19

<400> SEQUENCE: 3
acttctgact ggga                                                     14

<210> SEQ ID NO 4
<211> LENGTH: 17
<212> TYPE: DNA
<213> ORGANISM: Erythrovirus B19

<400> SEQUENCE: 4
gaatgtaaca aatttga                                                  17

<210> SEQ ID NO 5
<211> LENGTH: 14
<212> TYPE: DNA
<213> ORGANISM: Erythrovirus B19

<400> SEQUENCE: 5
ttatttaata atgt                                                     14

<210> SEQ ID NO 6
<211> LENGTH: 13
<212> TYPE: DNA
<213> ORGANISM: Erythrovirus B19

<400> SEQUENCE: 6
cttgtaactg aaa                                                      13

<210> SEQ ID NO 7
<211> LENGTH: 14
<212> TYPE: DNA
<213> ORGANISM: Erythrovirus B19

<400> SEQUENCE: 7
tttagagatg gaga                                                     14

<210> SEQ ID NO 8
<211> LENGTH: 14
<212> TYPE: DNA
<213> ORGANISM: Erythrovirus B19

<400> SEQUENCE: 8
ttaatgaaaa aaat                                                     14

<210> SEQ ID NO 9
<211> LENGTH: 14
<212> TYPE: DNA
<213> ORGANISM: Erythrovirus B19

<400> SEQUENCE: 9
cctttaaatg ttgt                                                     14

<210> SEQ ID NO 10
<211> LENGTH: 15
<212> TYPE: DNA
```

```
<213> ORGANISM: Erythrovirus B19

<400> SEQUENCE: 10
cagactttga gcagg                                                      15

<210> SEQ ID NO 11
<211> LENGTH: 14
<212> TYPE: DNA
<213> ORGANISM: Erythrovirus B19

<400> SEQUENCE: 11
tggaataatg aaaa                                                       14

<210> SEQ ID NO 12
<211> LENGTH: 20
<212> TYPE: DNA
<213> ORGANISM: Erythrovirus B19

<400> SEQUENCE: 12
tttccattta atgatgtagc                                                 20

<210> SEQ ID NO 13
<211> LENGTH: 17
<212> TYPE: DNA
<213> ORGANISM: Erythrovirus B19

<400> SEQUENCE: 13
ttggtggtct gggatga                                                    17

<210> SEQ ID NO 14
<211> LENGTH: 23
<212> TYPE: DNA
<213> ORGANISM: Erythrovirus B19

<400> SEQUENCE: 14
gaagctgcaa aagccatttt agg                                             23

<210> SEQ ID NO 15
<211> LENGTH: 14
<212> TYPE: DNA
<213> ORGANISM: Erythrovirus B19

<400> SEQUENCE: 15
accagggtag atca                                                       14

<210> SEQ ID NO 16
<211> LENGTH: 23
<212> TYPE: DNA
<213> ORGANISM: Erythrovirus B19

<400> SEQUENCE: 16
ataaccagca atggtgacat tac                                             23

<210> SEQ ID NO 17
<211> LENGTH: 17
<212> TYPE: DNA
<213> ORGANISM: Erythrovirus B19

<400> SEQUENCE: 17
catgctaaag ccttaaa                                                    17

<210> SEQ ID NO 18
<211> LENGTH: 14
```

```
<212> TYPE: DNA
<213> ORGANISM: Erythrovirus B19

<400> SEQUENCE: 18
agccctgaca tggg                                                    14

<210> SEQ ID NO 19
<211> LENGTH: 21
<212> TYPE: DNA
<213> ORGANISM: Erythrovirus B19

<400> SEQUENCE: 19
tggtgtaatg cacaaagctg g                                            21

<210> SEQ ID NO 20
<211> LENGTH: 30
<212> TYPE: DNA
<213> ORGANISM: Erythrovirus B19

<400> SEQUENCE: 20
ccactatgaa aactgggcaa taaactacac                                   30

<210> SEQ ID NO 21
<211> LENGTH: 17
<212> TYPE: DNA
<213> ORGANISM: Erythrovirus B19

<400> SEQUENCE: 21
tttgatttcc ctggaat                                                 17

<210> SEQ ID NO 22
<211> LENGTH: 23
<212> TYPE: DNA
<213> ORGANISM: Erythrovirus B19

<400> SEQUENCE: 22
aatgcagatg ccctccaccc aga                                          23

<210> SEQ ID NO 23
<211> LENGTH: 14
<212> TYPE: DNA
<213> ORGANISM: Erythrovirus B19

<400> SEQUENCE: 23
ctccaaacca cccc                                                    14

<210> SEQ ID NO 24
<211> LENGTH: 35
<212> TYPE: DNA
<213> ORGANISM: Erythrovirus B19

<400> SEQUENCE: 24
tcagcagcag tggtggtgaa agctctgaag aactc                             35

<210> SEQ ID NO 25
<211> LENGTH: 16
<212> TYPE: DNA
<213> ORGANISM: Erythrovirus B19

<400> SEQUENCE: 25
ccaggcgcct ggaaca                                                  16

<210> SEQ ID NO 26
```

```
<211> LENGTH: 24
<212> TYPE: DNA
<213> ORGANISM: Erythrovirus B19

<400> SEQUENCE: 26
tgaaaccccg cgctctagta cgcc                                          24

<210> SEQ ID NO 27
<211> LENGTH: 38
<212> TYPE: DNA
<213> ORGANISM: Erythrovirus B19

<400> SEQUENCE: 27
tccccgggac cagttcagga gaatcatttg tcggaagc                           38

<210> SEQ ID NO 28
<211> LENGTH: 20
<212> TYPE: DNA
<213> ORGANISM: Erythrovirus B19

<400> SEQUENCE: 28
cagtttcgtg aactgttagt                                               20

<210> SEQ ID NO 29
<211> LENGTH: 20
<212> TYPE: DNA
<213> ORGANISM: Erythrovirus B19

<400> SEQUENCE: 29
gcttggtata atggatggaa                                               20

<210> SEQ ID NO 30
<211> LENGTH: 14
<212> TYPE: DNA
<213> ORGANISM: Erythrovirus B19

<400> SEQUENCE: 30
aaatgtgctt acct                                                     14

<210> SEQ ID NO 31
<211> LENGTH: 19
<212> TYPE: DNA
<213> ORGANISM: Erythrovirus B19

<400> SEQUENCE: 31
tttgtagatt atgagtaaa                                                19

<210> SEQ ID NO 32
<211> LENGTH: 17
<212> TYPE: DNA
<213> ORGANISM: Erythrovirus B19

<400> SEQUENCE: 32
atttctttag ataatcc                                                  17

<210> SEQ ID NO 33
<211> LENGTH: 19
<212> TYPE: DNA
<213> ORGANISM: Erythrovirus B19

<400> SEQUENCE: 33
tatatagtca tcattttca                                                19
```

<210> SEQ ID NO 34
<211> LENGTH: 43
<212> TYPE: DNA
<213> ORGANISM: Erythrovirus B19

<400> SEQUENCE: 34
catggacagt tatctgacca cccccatgcc ttatcatcca gta        43

<210> SEQ ID NO 35
<211> LENGTH: 33
<212> TYPE: DNA
<213> ORGANISM: Erythrovirus B19

<400> SEQUENCE: 35
cagaacctag aggagaaaat gcagtattat cta        33

<210> SEQ ID NO 36
<211> LENGTH: 31
<212> TYPE: DNA
<213> ORGANISM: Erythrovirus B19

<400> SEQUENCE: 36
tgaagactta cacaagcctg ggcaagttag c        31

<210> SEQ ID NO 37
<211> LENGTH: 35
<212> TYPE: DNA
<213> ORGANISM: Erythrovirus B19

<400> SEQUENCE: 37
tacccggtac taactatgtt gggcctggca atgag        35

<210> SEQ ID NO 38
<211> LENGTH: 13
<212> TYPE: DNA
<213> ORGANISM: Erythrovirus B19

<400> SEQUENCE: 38
tacaagctgg gcc        13

<210> SEQ ID NO 39
<211> LENGTH: 39
<212> TYPE: DNA
<213> ORGANISM: Erythrovirus B19

<400> SEQUENCE: 39
gacagtgctg caaggattca tgactttagg tatagccaa        39

<210> SEQ ID NO 40
<211> LENGTH: 23
<212> TYPE: DNA
<213> ORGANISM: Erythrovirus B19

<400> SEQUENCE: 40
ttaaaaaata taaaaaatga aac        23

<210> SEQ ID NO 41
<211> LENGTH: 53
<212> TYPE: DNA
<213> ORGANISM: Erythrovirus B19

<400> SEQUENCE: 41
tactttactt taaaaggtgc agctgccccct gtggcccatt ttcaaggaag ttt        53

<210> SEQ ID NO 42
<211> LENGTH: 23
<212> TYPE: DNA
<213> ORGANISM: Erythrovirus B19

<400> SEQUENCE: 42
tacaacgcct cagaaaaata ccc                                          23

<210> SEQ ID NO 43
<211> LENGTH: 17
<212> TYPE: DNA
<213> ORGANISM: Erythrovirus B19

<400> SEQUENCE: 43
agcatgactt cagttaa                                                 17

<210> SEQ ID NO 44
<211> LENGTH: 26
<212> TYPE: DNA
<213> ORGANISM: Erythrovirus B19

<400> SEQUENCE: 44
tctgcagaag ccagcactgg tgcagg                                       26

<210> SEQ ID NO 45
<211> LENGTH: 17
<212> TYPE: DNA
<213> ORGANISM: Erythrovirus B19

<400> SEQUENCE: 45
aaaagcatgt ggagtga                                                 17

<210> SEQ ID NO 46
<211> LENGTH: 17
<212> TYPE: DNA
<213> ORGANISM: Erythrovirus B19

<400> SEQUENCE: 46
agtagctgcc acaatgc                                                 17

<210> SEQ ID NO 47
<211> LENGTH: 17
<212> TYPE: DNA
<213> ORGANISM: Erythrovirus B19

<400> SEQUENCE: 47
ttagatttta atgcttt                                                 17

<210> SEQ ID NO 48
<211> LENGTH: 14
<212> TYPE: DNA
<213> ORGANISM: Erythrovirus B19

<400> SEQUENCE: 48
gatgctttaa ctgt                                                    14

<210> SEQ ID NO 49
<211> LENGTH: 20
<212> TYPE: DNA
<213> ORGANISM: Erythrovirus B19

<400> SEQUENCE: 49
tatgcttact taacagtagg                                              20

<210> SEQ ID NO 50
<211> LENGTH: 14
<212> TYPE: DNA
<213> ORGANISM: Erythrovirus B19

<400> SEQUENCE: 50
agtgaagaat cagc                                                    14

<210> SEQ ID NO 51
<211> LENGTH: 17
<212> TYPE: DNA
<213> ORGANISM: Erythrovirus B19

<400> SEQUENCE: 51
ttttatgaaa tgtacaa                                                 17

<210> SEQ ID NO 52
<211> LENGTH: 20
<212> TYPE: DNA
<213> ORGANISM: Erythrovirus B19

<400> SEQUENCE: 52
gctgaagaca aagagtatca                                              20

<210> SEQ ID NO 53
<211> LENGTH: 14
<212> TYPE: DNA
<213> ORGANISM: Erythrovirus B19

<400> SEQUENCE: 53
aatgaaaaag aaca                                                    14

<210> SEQ ID NO 54
<211> LENGTH: 14
<212> TYPE: DNA
<213> ORGANISM: Erythrovirus B19

<400> SEQUENCE: 54
tggaacagaa gagc                                                    14

<210> SEQ ID NO 55
<211> LENGTH: 14
<212> TYPE: DNA
<213> ORGANISM: Erythrovirus B19

<400> SEQUENCE: 55
cttcactatg aaag                                                    14

<210> SEQ ID NO 56
<211> LENGTH: 21
<212> TYPE: DNA
<213> ORGANISM: Erythrovirus B19

<400> SEQUENCE: 56
cctcaaatat ttttaaaaat a                                            21

<210> SEQ ID NO 57
<211> LENGTH: 21
<212> TYPE: DNA
<213> ORGANISM: Erythrovirus B19

<400> SEQUENCE: 57
cctcaaatat ttttaaaaat a                                          21

<210> SEQ ID NO 58
<211> LENGTH: 17
<212> TYPE: DNA
<213> ORGANISM: Erythrovirus B19

<400> SEQUENCE: 58
catttaccat atgtact                                               17

<210> SEQ ID NO 59
<211> LENGTH: 26
<212> TYPE: DNA
<213> ORGANISM: Erythrovirus B19

<400> SEQUENCE: 59
tatgacccca cagctacaga tgcaaa                                     26

<210> SEQ ID NO 60
<211> LENGTH: 29
<212> TYPE: DNA
<213> ORGANISM: Erythrovirus B19

<400> SEQUENCE: 60
ggatatgaaa agcctgaaga attgtggac                                  29

<210> SEQ ID NO 61
<211> LENGTH: 39
<212> TYPE: DNA
<213> ORGANISM: Erythrovirus B19

<400> SEQUENCE: 61
cacttctgac tgggaaccat taactcattc taacagact                       39

<210> SEQ ID NO 62
<211> LENGTH: 39
<212> TYPE: DNA
<213> ORGANISM: Erythrovirus B19

<400> SEQUENCE: 62
atgtaaagct taaattttta ccaggaatga ctacaaaag                       39

<210> SEQ ID NO 63
<211> LENGTH: 39
<212> TYPE: DNA
<213> ORGANISM: Erythrovirus B19

<400> SEQUENCE: 63
aatattttag agatggagaa caatttatag aaaattatt                       39

<210> SEQ ID NO 64
<211> LENGTH: 39
<212> TYPE: DNA
<213> ORGANISM: Erythrovirus B19

<400> SEQUENCE: 64
attttagaga tggagaacaa tttatagaaa attatttaa                       39

<210> SEQ ID NO 65
<211> LENGTH: 39
<212> TYPE: DNA
<213> ORGANISM: Erythrovirus B19

<400> SEQUENCE: 65
taaccaatat tgatgggtac atagatacct gcatttctg					39

<210> SEQ ID NO 66
<211> LENGTH: 39
<212> TYPE: DNA
<213> ORGANISM: Erythrovirus B19

<400> SEQUENCE: 66
atgggtacat agatacctgc atttctgctt cttttagac					39

<210> SEQ ID NO 67
<211> LENGTH: 39
<212> TYPE: DNA
<213> ORGANISM: Erythrovirus B19

<400> SEQUENCE: 67
ttagacgggg agcctttcag gctaaaaaac cccgcatta					39

<210> SEQ ID NO 68
<211> LENGTH: 39
<212> TYPE: DNA
<213> ORGANISM: Erythrovirus B19

<400> SEQUENCE: 68
gaaccagggg aatctagcgc tacaggggga gatgttgtg					39

<210> SEQ ID NO 69
<211> LENGTH: 39
<212> TYPE: DNA
<213> ORGANISM: Erythrovirus B19

<400> SEQUENCE: 69
tgccatttgc tgggaagggg actaaagctg gaataaaat					39

<210> SEQ ID NO 70
<211> LENGTH: 39
<212> TYPE: DNA
<213> ORGANISM: Erythrovirus B19

<400> SEQUENCE: 70
ggactaaagc tggaataaaa tttcaaacta tggtaaatt					39

<210> SEQ ID NO 71
<211> LENGTH: 39
<212> TYPE: DNA
<213> ORGANISM: Erythrovirus B19

<400> SEQUENCE: 71
taaattggtt gtgtgaaaat agggttttta cagaggata					39

<210> SEQ ID NO 72
<211> LENGTH: 39
<212> TYPE: DNA
<213> ORGANISM: Erythrovirus B19

<400> SEQUENCE: 72
attggttgtg tgaaaatagg gttttacag aggataagt					39

<210> SEQ ID NO 73
<211> LENGTH: 39
<212> TYPE: DNA
<213> ORGANISM: Erythrovirus B19

<400> SEQUENCE: 73
ttaaccagta cactttactt agcagtagtc acagtggga    39

<210> SEQ ID NO 74
<211> LENGTH: 39
<212> TYPE: DNA
<213> ORGANISM: Erythrovirus B19

<400> SEQUENCE: 74
taaaactagc tatttataag gctaccaatt tagtgccta    39

<210> SEQ ID NO 75
<211> LENGTH: 39
<212> TYPE: DNA
<213> ORGANISM: Erythrovirus B19

<400> SEQUENCE: 75
tagctattta taaggctacc aatttagtgc ctacaagta    39

<210> SEQ ID NO 76
<211> LENGTH: 39
<212> TYPE: DNA
<213> ORGANISM: Erythrovirus B19

<400> SEQUENCE: 76
ctaccaattt agtgcctaca agtacatttt tgttacaca    39

<210> SEQ ID NO 77
<211> LENGTH: 39
<212> TYPE: DNA
<213> ORGANISM: Erythrovirus B19

<400> SEQUENCE: 77
caagtacatt tttgttacac acagactttg agcaggcta    39

<210> SEQ ID NO 78
<211> LENGTH: 39
<212> TYPE: DNA
<213> ORGANISM: Erythrovirus B19

<400> SEQUENCE: 78
cacacagact tgagcaggc taactgtatt aaagaaaat    39

<210> SEQ ID NO 79
<211> LENGTH: 39
<212> TYPE: DNA
<213> ORGANISM: Erythrovirus B19

<400> SEQUENCE: 79
gtgtcaaaat tatgaccct tgttggtggg acagcatgt    39

<210> SEQ ID NO 80
<211> LENGTH: 39
<212> TYPE: DNA
<213> ORGANISM: Erythrovirus B19

<400> SEQUENCE: 80
ggattgataa aaaatgtggc aaaaaaaata cactgtggt    39

<210> SEQ ID NO 81
<211> LENGTH: 39
<212> TYPE: DNA
<213> ORGANISM: Erythrovirus B19

```
<400> SEQUENCE: 81
atacactgtg gttttatggc ccaccaagta caggaaaaa                              39

<210> SEQ ID NO 82
<211> LENGTH: 39
<212> TYPE: DNA
<213> ORGANISM: Erythrovirus B19

<400> SEQUENCE: 82
gtacaggaaa aacaaattta gcaatggcta ttgctaaaa                              39

<210> SEQ ID NO 83
<211> LENGTH: 39
<212> TYPE: DNA
<213> ORGANISM: Erythrovirus B19

<400> SEQUENCE: 83
gcttggtggt ctgggatgag ggtattatta agtctacta                              39

<210> SEQ ID NO 84
<211> LENGTH: 39
<212> TYPE: DNA
<213> ORGANISM: Erythrovirus B19

<400> SEQUENCE: 84
gcttacttac agaggctgac gtgcagcaat ggcttacat                              39

<210> SEQ ID NO 85
<211> LENGTH: 39
<212> TYPE: DNA
<213> ORGANISM: Erythrovirus B19

<400> SEQUENCE: 85
ccccgcgctc tagtacgcca gtccccggga ccagttcag                              39

<210> SEQ ID NO 86
<211> LENGTH: 39
<212> TYPE: DNA
<213> ORGANISM: Erythrovirus B19

<400> SEQUENCE: 86
agaatcattt gtcggaagct caatttcctc cgaagctgt                              39

<210> SEQ ID NO 87
<211> LENGTH: 39
<212> TYPE: DNA
<213> ORGANISM: Erythrovirus B19

<400> SEQUENCE: 87
atcatttgtc ggaagctcaa tttcctccga agctgtagc                              39

<210> SEQ ID NO 88
<211> LENGTH: 39
<212> TYPE: DNA
<213> ORGANISM: Erythrovirus B19

<400> SEQUENCE: 88
agctcaattt cctccgaagc tgtagctgca tcgtgggaa                              39

<210> SEQ ID NO 89
<211> LENGTH: 39
<212> TYPE: DNA
```

<213> ORGANISM: Erythrovirus B19

<400> SEQUENCE: 89
tgactatgta tgggatggta taagggqttt acctgtttg                              39

<210> SEQ ID NO 90
<211> LENGTH: 39
<212> TYPE: DNA
<213> ORGANISM: Erythrovirus B19

<400> SEQUENCE: 90
ttaataacag tgggggaggc ttgggatttt gtccccatt                              39

<210> SEQ ID NO 91
<211> LENGTH: 39
<212> TYPE: DNA
<213> ORGANISM: Erythrovirus B19

<400> SEQUENCE: 91
cagtggggga ggcttgggat tttgtcccca ttgcattaa                              39

<210> SEQ ID NO 92
<211> LENGTH: 39
<212> TYPE: DNA
<213> ORGANISM: Erythrovirus B19

<400> SEQUENCE: 92
gcaaaaaatg tgcttaccta tctggcttgc aaagttttg                              39

<210> SEQ ID NO 93
<211> LENGTH: 39
<212> TYPE: DNA
<213> ORGANISM: Erythrovirus B19

<400> SEQUENCE: 93
aatgtgctta cctatctggc ttgcaaagtt ttgtagatt                              39

<210> SEQ ID NO 94
<211> LENGTH: 39
<212> TYPE: DNA
<213> ORGANISM: Erythrovirus B19

<400> SEQUENCE: 94
tttgtagatt atgagtaaag aaattggtaa atggtggga                              39

<210> SEQ ID NO 95
<211> LENGTH: 39
<212> TYPE: DNA
<213> ORGANISM: Erythrovirus B19

<400> SEQUENCE: 95
ttatgagtaa agaaattggt aaatggtggg aaagtgatg                              39

<210> SEQ ID NO 96
<211> LENGTH: 39
<212> TYPE: DNA
<213> ORGANISM: Erythrovirus B19

<400> SEQUENCE: 96
cttctttgtt tgacttagtg gctcgtatta aaagtaacc                              39

<210> SEQ ID NO 97
<211> LENGTH: 39

<212> TYPE: DNA
<213> ORGANISM: Erythrovirus B19

<400> SEQUENCE: 97
atgaaactgg gtttcaagct caagtagtaa aagactact                    39

<210> SEQ ID NO 98
<211> LENGTH: 39
<212> TYPE: DNA
<213> ORGANISM: Erythrovirus B19

<400> SEQUENCE: 98
tcctgatgct ttaactgttg ccatatcaga aattgccat                    39

<210> SEQ ID NO 99
<211> LENGTH: 39
<212> TYPE: DNA
<213> ORGANISM: Erythrovirus B19

<400> SEQUENCE: 99
ttgccatatc agaaattgcc attaaagatg ttacagaca                    39

<210> SEQ ID NO 100
<211> LENGTH: 39
<212> TYPE: DNA
<213> ORGANISM: Erythrovirus B19

<400> SEQUENCE: 100
tgccatatca gaaattgcca ttaaagatgt tacagacaa                    39

<210> SEQ ID NO 101
<211> LENGTH: 39
<212> TYPE: DNA
<213> ORGANISM: Erythrovirus B19

<400> SEQUENCE: 101
aatacaagta cccatatgta ttaggtcaag gacaagata                    39

<210> SEQ ID NO 102
<211> LENGTH: 39
<212> TYPE: DNA
<213> ORGANISM: Erythrovirus B19

<400> SEQUENCE: 102
aagatacctt agccccagag cttccaattt gggtgtact                    39

<210> SEQ ID NO 103
<211> LENGTH: 39
<212> TYPE: DNA
<213> ORGANISM: Erythrovirus B19

<400> SEQUENCE: 103
cagtaggaga tgtaaacacg cagggaattt ctggggaca                    39

<210> SEQ ID NO 104
<211> LENGTH: 39
<212> TYPE: DNA
<213> ORGANISM: Erythrovirus B19

<400> SEQUENCE: 104
agaatcagcg ttttatgtcc tggaacacag ctcttttga                    39

<210> SEQ ID NO 105

```
<211> LENGTH: 39
<212> TYPE: DNA
<213> ORGANISM: Erythrovirus B19

<400> SEQUENCE: 105
ctactatgtc ttataagttc cctccagtgc ccccagaga                              39

<210> SEQ ID NO 106
<211> LENGTH: 39
<212> TYPE: DNA
<213> ORGANISM: Erythrovirus B19

<400> SEQUENCE: 106
tccctccagt gcccccagag aatttagaag gctgtagtc                              39

<210> SEQ ID NO 107
<211> LENGTH: 39
<212> TYPE: DNA
<213> ORGANISM: Erythrovirus B19

<400> SEQUENCE: 107
cccgtttagg agtccctgat acattaggag gggacccca                              39

<210> SEQ ID NO 108
<211> LENGTH: 39
<212> TYPE: DNA
<213> ORGANISM: Erythrovirus B19

<400> SEQUENCE: 108
aacacatgaa gaccacgcag ttcagccaca aaattttat                              39

<210> SEQ ID NO 109
<211> LENGTH: 39
<212> TYPE: DNA
<213> ORGANISM: Erythrovirus B19

<400> SEQUENCE: 109
acgcagttca gccacaaaat tttatgccag ggccactgg                              39

<210> SEQ ID NO 110
<211> LENGTH: 39
<212> TYPE: DNA
<213> ORGANISM: Erythrovirus B19

<400> SEQUENCE: 110
ggccactggt aaactcagtt tccacaaagg agggagaca                              39

<210> SEQ ID NO 111
<211> LENGTH: 39
<212> TYPE: DNA
<213> ORGANISM: Erythrovirus B19

<400> SEQUENCE: 111
aggagggaga cagttctaac acaggagcgg gaaaagccc                              39

<210> SEQ ID NO 112
<211> LENGTH: 39
<212> TYPE: DNA
<213> ORGANISM: Erythrovirus B19

<400> SEQUENCE: 112
gtcaaagtac tagaatatca ttacgccctg gtccagtgt                              39
```

```
<210> SEQ ID NO 113
<211> LENGTH: 39
<212> TYPE: DNA
<213> ORGANISM: Erythrovirus B19

<400> SEQUENCE: 113
gccctggtcc agtgtctcaa ccatatcacc actgggaca              39

<210> SEQ ID NO 114
<211> LENGTH: 39
<212> TYPE: DNA
<213> ORGANISM: Erythrovirus B19

<400> SEQUENCE: 114
gtccagtgtc tcaaccatat caccactggg acacagata              39

<210> SEQ ID NO 115
<211> LENGTH: 39
<212> TYPE: DNA
<213> ORGANISM: Erythrovirus B19

<400> SEQUENCE: 115
cagataaata tgtaacaggg ataaatgcca tttctcatg              39

<210> SEQ ID NO 116
<211> LENGTH: 39
<212> TYPE: DNA
<213> ORGANISM: Erythrovirus B19

<400> SEQUENCE: 116
ctgaagacaa agagtatcaa cagggcgtgg gtaggtttc              39

<210> SEQ ID NO 117
<211> LENGTH: 39
<212> TYPE: DNA
<213> ORGANISM: Erythrovirus B19

<400> SEQUENCE: 117
aagacaaaga gtatcaacag ggcgtgggta ggtttccca              39

<210> SEQ ID NO 118
<211> LENGTH: 39
<212> TYPE: DNA
<213> ORGANISM: Erythrovirus B19

<400> SEQUENCE: 118
agggcgtggg taggtttccc aatgaaaaag aacaactaa              39

<210> SEQ ID NO 119
<211> LENGTH: 39
<212> TYPE: DNA
<213> ORGANISM: Erythrovirus B19

<400> SEQUENCE: 119
aacagttaca gggtttaaat atacacacat attttccca              39

<210> SEQ ID NO 120
<211> LENGTH: 39
<212> TYPE: DNA
<213> ORGANISM: Erythrovirus B19

<400> SEQUENCE: 120
gtttaaatat acacacatat ttcccaata aggtaccc               39
```

<210> SEQ ID NO 121
<211> LENGTH: 39
<212> TYPE: DNA
<213> ORGANISM: Erythrovirus B19

<400> SEQUENCE: 121
taccaaattt agatgacagc tttaaaactc agtttgcag                                39

<210> SEQ ID NO 122
<211> LENGTH: 39
<212> TYPE: DNA
<213> ORGANISM: Erythrovirus B19

<400> SEQUENCE: 122
agctttagga ggttggggac tacatcagcc acccctca                                 39

<210> SEQ ID NO 123
<211> LENGTH: 39
<212> TYPE: DNA
<213> ORGANISM: Erythrovirus B19

<400> SEQUENCE: 123
ggccaattgg gggtattaag tcaatgggaa taacaacat                                39

<210> SEQ ID NO 124
<211> LENGTH: 39
<212> TYPE: DNA
<213> ORGANISM: Erythrovirus B19

<400> SEQUENCE: 124
ttaagtcaat gggaataaca acattagttc aatatgctg                                39

<210> SEQ ID NO 125
<211> LENGTH: 39
<212> TYPE: DNA
<213> ORGANISM: Erythrovirus B19

<400> SEQUENCE: 125
tagttcaata tgctgtgggt attatgacag taactatga                                39

<210> SEQ ID NO 126
<211> LENGTH: 39
<212> TYPE: DNA
<213> ORGANISM: Erythrovirus B19

<400> SEQUENCE: 126
taactatgac atttaaatta gggcctcgca aagctacag                                39

<210> SEQ ID NO 127
<211> LENGTH: 39
<212> TYPE: DNA
<213> ORGANISM: Erythrovirus B19

<400> SEQUENCE: 127
accctcctca cgcagcaggc catttaccat atgtactat                                39

<210> SEQ ID NO 128
<211> LENGTH: 4611
<212> TYPE: DNA
<213> ORGANISM: Erythrovirus B19

<400> SEQUENCE: 128
acgcggggac tacagtatat atagcacggc actgccgcag ctctttctttt ctgagctgct        60

```
ttttcctgga ctttcttgct gttgtttgtg agctaactaa caggtattta tactacttgt    120
taacatacta acatggagct atttagaggg gtgcttcaag tttcttctaa tgttctggac    180
tgtgctaacg ataactggtg gtgctcttta ctggatttag acacctctga ctgggaacca    240
ctaactcata ctaacagact aatggcaata tacctaaaac agtgtggctt ctaagcttga    300
ctttaccggg gggccactag cagggtgctt gtactttttt caagttgaat gtaacaaatt    360
tgaagaaggc tatcatattc atgtggttat tgggggggcca gggttaaacc ccagaaacct    420
aacagtgtgt gtagaggggt tatttaacaa tgtactttat caccttgtaa ctggagatgt    480
aaagctaaaa tttttgccag gaatgactac aaaaggcaaa tactttagag atggagagca    540
gtttatagaa aactatttaa tgaaaaaaat acctttgaat gttgtatggt gtgttactaa    600
tattgatgga tatatagata cctgtatttc tgctactttt agaaggggag cttgccatgc    660
caagaaaccc cgcatgacca cagccataaa tgatactagt agtgatgctg gggagtctag    720
cggcacaggg gcagaggttg tgccatttaa tggaaaggga actaaggcta gcataaagtt    780
tcagactatg gtaaactggt tgtgtgaaaa tagagtgttt acagaggata agtggaaact    840
agttgacttt aaccagtaca ctttactaag cagtagtcac agtggaagtt ttcaaattca    900
aagtgcacta aaactagcaa tttataaagc aactaattta gtgcctacta gcacattttt    960
attgcataca gactttgagc aggttatgtg tattaaagac aataaaattg ttaaattgtt   1020
actttgtcaa aactatgacc ccctattggt ggggcagcat gtgttaaagt ggattgataa   1080
aaaatgtggc aagaaaaata cactgtggtt ttatgggccg ccaagtacag gaaaaacaaa   1140
cttggcaatg gctattgcta aaagtgttcc agtatatggc atggttaact ggaataatga   1200
aaactttcca tttaatgatg tagcaggaa aagcttggtg gtctgggatg aaggtattat   1260
taagtccaca attgtagaag ctgcaaaagc cattttaggc gggcaaccta ccagggtaga   1320
tcaaaaaatg cgtggaagtg tagctgtgcc tggagtacct gtggttataa ccagcaatgg   1380
tgacattact tttgttgtaa gcgggaacac tacaacaact gtacacgcta aagccttaaa   1440
agagcgcatg gtaaagttaa actttactgt aagatgcagc cctgacatgg ggttactaac   1500
agaggctgat gtacaacagt ggcttacatg gtgtaatgca caaagctggg accactatga   1560
aaactgggca ataaactaca cttttgattt ccctggaatt aatgcagatg ccctccaccc   1620
agacctccaa accaccccaa ttgtcacaga caccagtatc agcagcagtg gtggtgaaag   1680
ctctgaagaa ctcagtgaaa gcagcttttt taacctcatc accccaggcg cctggaacac   1740
tgaaaccccg cgctctagta cgcccatccc cgggaccagt tcaggagaat catctgtcgg   1800
aagcccagtt tcctccgaag ttgtagctgc atcgtgggaa gaagccttct acacaccttt   1860
ggcagaccag tttcgtgaac tgttagttgg ggttgattat gtgtgggacg gtgtaagggg   1920
tttacctgtg tgttgtgtgc agcatattaa caatagtggg ggaggcttgg gactttgtcc   1980
ccattgcatt aatgtagggg cttggtataa tggatgaaa tttcgagaat ttaccccaga   2040
tttggtgcgg tgtagctgcc atgtgggagc ttctaatccc ttttctgtgc taacctgcaa   2100
aaaatgtgct tacctgtctg gattgcaaag ctttgtagat tatgagtaaa gaaagtggca   2160
aatggtggga aagtgatgat aaaatttgcta agctgtgta tcagcaattt gtggaatttt   2220
atgaaaagct tactggaaca gacttagagc ttattcaaat attaaagat cattacaata   2280 tttctttaga taatccccta gaaaacccat cctctctgtt tgacttagtt gctcgtatta   2340
aaaataacct taaaaactct ccagacttat atagtcatca ttttcaaagt catggacagt   2400
```

```
tatctgacca cccccatgcc ttatcatcca gtaacagtca tgcagaacct agaggagaaa    2460
atgcagtatt atctagtgaa gacttacaca agcctgggca agttagcgta caactacccg    2520
gtactaacta tgttgggcct ggcaatgagc tacaagctgg gccccgcaa agtgctgttg     2580 acagtgctgc aaggattcat gactttaggt atagccaact ggctaagttg gaataaatc     2640 catatactca ttggactgta gcagatgaag agcttttaaa taatataaaa aatgaaactg    2700
ggtttcaagc acaagtagta aaagactact ttactttaaa aggtgcagct gcccctgtgg    2760
cccattttca aggaagtttg ccggaagttc ccgcttacaa cgcctcagaa aaatacccaa    2820
gcatgacttc agttaattct gcagaagcca gcactggtgc aggagggggg ggcagtaatc    2880
ctgttaaaag catgtggagt gaggggggcca ctttttagtgc caactctgta acttgtacat   2940
tttccagaca gttttttaatt ccatatgacc cagagcacca ttataaggtg ttttctcccg    3000
cagcaagtag ctgccacaat gccagtggaa aggaggcaaa ggtttgcacc attagtccca    3060
taatgggata ctcaacccca tggagatatt tagattttaa tgctttaaat ttgtttttt     3120 caccttttaga gtttcagcat ttaattgaaa actatggaag tatagctcct gatgctttaa   3180
ctgtaaccat atcagaaatt gctgttaagg atgttacaga caaaactgga gggggagtac    3240
aagttactga cagcactacc gggcgcctat gcatgttagt agaccatgaa tacaagtacc    3300
catatgtgtt agggcaaggt caggatactt tagccccaga acttcctatt tgggtatact    3360
ttccccctca atatgcttac ttgacagtag agatgttaa cacacaagga atttctggag     3420
acagcaaaaa attagcaagt gaagaatcag catttatgt tttggaacac agttcttttc    3480
agcttttagg tacaggaggt acagcaacta tgtcctataa gtttcctcca gtgccccag     3540 aaaatttaga gggctgcagt caacacttttt atgaaatgta caatcccttaa cggatctc    3600 gcttaggggt ccctgacaca ttaggagtg acccaaaatt tagatcttta acacatgaag    3660
accatgcaat tcagccccaa aactttatgc cagggccact agtaaactca gtgtctacaa    3720
aggagggaga cagctctagt actggagctg gaaaagcctt aacaggcctt agcacaggaa    3780
cctctcaaaa cactagaata tccttacgcc ctgggccagt gtctcagcca tatcaccact     3840
gggacacaga taaatatgtt acaggaataa atgccatttc tcatggtcag accacatatg    3900
gtaatgctga agataaagag tatcagcaag gagtgggtag atttccaaat gaaaaagaac    3960
agctaaaaca gttacagggc ttaaacatgc acacctattt tcccaataaa ggaacccagc    4020
aatatacaga tcaaattgag cgccccctaa tggtgggttc tgtatggaac agaagagccc    4080
ttcactatga aagccagctg tggagtaaaa ttccaaattt agatgacagt tttaaaactc    4140
agtttgcagc cttaggagga tggggtttgc atcagccacc tcctcaaata ttttttaaaaa   4200 tattaccaca aagtgggccc attggaggta ttaaatcaat gggaattact accttagttc    4260
agtatgccgt gggaattatg acagtcacta tgacatttaa attgggggcc cgtaaagcta    4320
cgggacggtg gaatcctcaa cctggagtat atccccgca cgccgcaggt catttaccat     4380
atgtactata tgacccccaca gctacagatg caaaacaaca ccacagacat ggatatgaaa    4440
agcctgaaga attgtggaca gccaaaagcc gtgtgcaccc attgtaaaca ctccccaccg    4500
tgccctcagc caggatgcgt aactaaacgc ccaccagtac cacccagact gtacctgccc    4560
ccgcgtatac ctataagaca gcctaacaca aaagatatag acaatgtaga a              4611
```

<210> SEQ ID NO 129
<211> LENGTH: 4846
<212> TYPE: DNA
<213> ORGANISM: Erythrovirus B19

<400> SEQUENCE: 129

```
atctgatttg gtgtcttctt tttaaaattt tggcgggctt tttcccgcct tatgcaaata      60
agctgccatg tttaatattt tattttaatt taattggaca gacgcctaac ggttattata     120
ggcggagtta cgggcggtat ataagcagct gtgctctgtg gcactttctt ttctggttgc     180
ttttgactgg aactcacttg ctgttctttg cctgctaact aacaggtatt tatactaact     240
tttaatttac taacatggag ctatttcggg gtgtcttgca catttcctct aacattctgg     300
actgtgctaa tgataactgg tggtgctcta tgctagactt agatacttct gattgggaac     360
cactaactca ttctaacaga ttaatggcaa tatatttaag cagtgttgct tctaagcttg     420
attttactgg ggggccgcta gcaggttgct tatactttt ccaggtggag tgtaacaaat      480
ttgaggaagg ctatcatatt catgtagtta ttggtggtcc aggactaaat gctagaaact     540
taactgtgtg tgtagaaggt ttatttaata atgttcttta ccaccttgta actgaaagtg     600
ttaaacttaa attttgcca gggatgacta ccaaaggaaa atattttaga gatggagagc      660
agtttataga aaattactta atgaaaaaaa ttcctttaaa tgttgtgtgg tgtgtaacaa     720
atattgacgg gtatatagac acctgtattt ccgcctcttt tcggcgagga gcttgtcaag     780
ctaaaagacc ccgcattgcc gcaaatgcag acagtgttac tagtgaaacc ggggagtcta     840
gctgtgcagg gggagatgtt gtaccatttg ctggaaaggg aacaaaagcg gggttaaagt     900
tcaaaccat ggtaaattgg ctatgtgaaa acagagtatt tactgaagat aaatggaagt      960
tagtagattt taaccagtat accttattaa gtagtagtca cagtggcagc tttcaaatac    1020
aaagtgcctt aaagttagct atttataaag ctactaactt agtacccact agtacattct    1080
tgttacatgc agactttgag caggttactt gcattaaaga aaataaaata gttaaattat    1140
tactgtgtca aaactatgat cctctgctag tggggcaaca tgtgttaagg tggattgaca    1200
aaaaatgtgg taaaaaaaac accctatggt tttacgggcc accaagtact ggaaaaacaa    1260
atttagctat ggctattgct aaaactgtac ccgtgtatgg aatggttaac tggaataatg    1320
aaaactttcc atttaatgat gtggcgggga aagtttggt ggtctgggat gaaggcatta     1380
ttaagtccac tattgtggaa gctgcaaaag ccattctagg tggtcagcca accagggtag    1440
atcagaaaat gcgtggcagt gtggcagtgc ccggtgtgcc tgtggtcata accagcaacg    1500
gtgacattac atttgttgta agtggtaata ccactacaac tgtgcatgct aaagccttaa    1560
aagaacggat ggtaaagcta aattttacca taggtgtag ccctgacatg ggtttactaa     1620
cagaggctga tgtgcaacag tggctaactt ggtgtaatgc acaaagctgg agccactatg    1680
aaaactgggc aataaactac acgtttgatt ccctggaat aaatgcagat gccctccacc     1740
cagatctcca aaccacccc attgtcccag acaccagtat cagcagcagt ggtggtgaaa     1800
gctctgaaga actcagtgaa agcagctttt tcaacctcat cactccaggc gcctggaaca    1860
gtgaaacccc gcgctctagt acgcccgtcc ccgggaccag ttcaggagaa tcatttgtcg    1920
gaagcccagt ttcctccgaa gtggtagccg cgtcgtggga ggaagctttt tacacgccgc    1980
ttgcagatca gtttcgtgaa ctgttagtag gggttgacta tgtatgggat ggtgtaaggg    2040
gattgcctgt ttgctgtgtg gaacatatta ataacagtgg gggagggttg gggctttgtc    2100
ctcattgtat tcatgtggga gcttggtata atggatggaa atttagagag tttactccag    2160
acttagtgcg ctgtagttgt catgtaggag cctctaaccc attttctgtg ttaacttgta    2220
aaaaatgtgc ttacctgtct ggtttacaaa gctttgtaga ttatgagtaa aaccactgac    2280
```

```
aaatggtggg aaagtagtga caaatttgcc caggacgtgt ataagcagtt tgtacaattt    2340
tatgaaaaag ctactggaac agatttagag cttattcaaa ttttaaaaga tcattacaac    2400
atttctttag acaatccttt agaaaacccc tcttctttat ttgacttagt tgctcgcatt    2460
aaaagcaatc ttaaaaactc tccagaccta tatagtcatc attttcagag ccatggacag    2520
ttatctgacc accccattc cttatcaccc agtaacagta gtacagaacc tagaggagaa    2580
aatgcagtat tatctagtga agacttacac aagcctgggc aagttagcat acaattaccc    2640
ggtactaact atgttgggcc tggcaatgag ctacaagctg ggcctccgca gaatgctgtg    2700
gacagtgctg caaggattca tgactttagg tatagccaat tggctaagtt gggaataaat    2760
ccttatactc attggacggt agcagatgag gaattgttaa aaatatataa aaatgaaaca    2820
gggtttcaag cacaagcagt aaaagactac tttactttaa aaggtgcagc tgcccctgtg    2880
gcccattttc aaggaagttt accggaagtg cccgcgtaca acgcctcaga aaatacccc    2940 agcatgactt cagttaactc tgcagaagcc agcactggtg caggcggggg aggtagcaac    3000
cctacaaaaa gcatgtggaa tgaagggggct acattcactg ctaattctgt aacatgcaca    3060
ttctctaggc aattttttaat tccatatgat ccagagcatc attataaagt gttctcccca    3120
gcagctagta gctgccacaa tgctagcgga aaagaggcaa aagtgtgcac tattagtccc    3180
attatggggt actctactcc gtggagatac ttagattta atgctttaaa cttgtttttc    3240
tcaccattag agtttcagca cttaattgaa aattatggca gcatagctcc agatgcttta    3300
actgtaacta tttcagaaat tgctgtaaaa gatgttacag acaaaacagg gggaggtgtg    3360
caagttactg acagcacaac aggacgtttg tgtatgttag tggatcatga gtataagtac    3420
ccatatgtgc taggtcaggg acaagacaca ctagctccag aactgcccat tgggtgtac    3480 tttccccccc aatatgctta cttaacagta ggtgaagtaa acacacaagg aatttcagga    3540
gacagcaaaa aattagctag tgaagaatca gcttttatg tgttagagca cagttcattt    3600
gaacttttag gtacaggggg atcagccaca atgtcctaca aatttccagc agtgccccca    3660
gaaaacttag aaggttgcag ccaacatttt tatgaaatgt caaccccct gtacggttcc    3720 cgattagggg tacctgacac attaggaggg gaccctaaat ttagatcatt aacacacgaa    3780
gaccatgcaa ttcagccaca aaactttatg cctgggccac taataaattc agtatctacc    3840
aaagaaggag acaattctaa tacaggtgct ggaaaagccc ttacggggct tagtactggc    3900
actagtcaaa acaccagaat ttccctacgc ccagggccag tgtctcagcc ataccatcac    3960
tgggacactg ataaatatgt tacaggaata aatgccattt cacatggaca aaccaccta    4020 ggaaatgctg aggacaaaga atatcagcaa ggggtaggaa gatttccaaa cgaaaaagaa    4080
cagcttaagc agttcaggg tcttaacatg cacacatact ttcctaataa aggaaccccaa    4140 caatacacag accaaattga acgccccctt atggtaggct ctgtttggaa cagaagagca    4200
cttcactatg aaagtcagct gtggagtaaa atccctaact agatgatag ttttaaaact    4260 caatttgcag ccctaggagg ttggggtttg catcaaccac cccctcaaat attttaaaa    4320 atactaccgc aaagtgggcc aattggaggt attaaatcca tgggaattac tactttagtt    4380
caatatgctg tgggaataat gacagttact atgacattta aattgggacc tcgaaaggct    4440
actggaaggt ggaatcccca gcctggagtg tatcctcctc atgcagctgg tcatttacca    4500
tatgtactgt atgaccccac agctacagat gcaaagcaac accacagaca cggatatgaa    4560
aagcctgaag aattgtggac tgccaaaagc cgtgtgcacc cattgtaaac attccccacc    4620
gtgccctctg ccaggaaccg tcaccaatcg cccacctgta ccgcccagat tatatgtgcc    4680
```

-continued

| | |
|---|---|
| ccctccaata ccccgtaggc aaccatctat aaaagataca gacgctgtag agtataaatt | 4740 |
| actaacccga tatgaacaac atgtaataag aatgctaaga ttatgtaata tgtacacaaa | 4800 |
| cttggaaaaa taaaaacctt aaataaaaaa ttaatagtgt atggtg | 4846 |

<210> SEQ ID NO 130
<211> LENGTH: 5112
<212> TYPE: DNA
<213> ORGANISM: Erythrovirus B19

<400> SEQUENCE: 130

| | |
|---|---|
| gaattccgcc aaatcagatg ccgccggtcg ccgccggtag gcgggacttc cggtacaaga | 60 |
| tggcggacaa ttacgtcatt tcctgtgacg tcatttcctg tgacgtcaca ggaaatgacg | 120 |
| taattgtccg ccatcttgta ccggaagtcc cgcctaccgg cggcgaccgg cggcatctga | 180 |
| tttggtgtct tcttttaaat tttagcgggc ttttttcccg ccttatgcaa atgggcagcc | 240 |
| attttaagtg ttttactata attttattgg ttagttttgt aacggttaaa atgggcggag | 300 |
| cgtaggcggg gactacagta tatatagcac ggtactgccg cagctctttc tttctgggct | 360 |
| gcttttt cct ggactttctt gctgttttt gtgagctaac taacaggtat ttatactact | 420 |
| tgttaacatc ctaacatgga gctatttaga ggggtgcttc aagtttcttc taatgttcta | 480 |
| gactgtgcta acgataactg gtggtgctct ttactggatt tagacacttc tgactgggaa | 540 |
| ccactaactc atactaacag actaatggca atatacttaa gcagtgtggc ttctaagctt | 600 |
| gactttaccg gggggccact agcagggtgc ttgtacttt tcaagtaga atgtaacaaa | 660 |
| tttgaagaag gctatcatat tcatgtggtt actgggggc cagggttaaa ccccagaaac | 720 |
| cttacagtgt gtgtagaggg gttatttaat aatgtacttt atcaccttgt aactgaaaat | 780 |
| gtgaagctaa aattttgcc aggaatgact acaaaaggca aatactttag agatggagag | 840 |
| cagtttatag aaaactattt aatgaaaaaa ataccttaa atgttgtatg gtgtgttact | 900 |
| aatattgatg gatatataga tacctgtatt tctgctactt ttagaagggg agcttgccat | 960 |
| gccaagaaac cccgcattac cacagccata aatgatacta gtagtgatgc tgggagtct | 1020 |
| agcggcacag gggcagaggt tgtgccattt aatgggaagg gaactaaggc tagcataaag | 1080 |
| tttcaaacta tggtaaactg gttgtgtgaa aacagagtgt ttacagagga taagtggaaa | 1140 |
| ctagttgact ttaaccagta cactttacta agcagtagtc acagtggaag ttttcaaatt | 1200 |
| caaagtgcac taaaactagc aatttataaa gcaactaatt tagtgcctac tagcacattt | 1260 |
| ttattgcata cagactttga gcaggttatg tgtattaaag acaataaaat tgttaaattg | 1320 |
| ttactttgtc aaaactatga cccctattg gtgggcagc atgtgtaaaa gtggattgat | 1380 |
| aaaaatgtg gtaagaaaaa tacactgtgg ttttatgggc cgccaagtac aggaaaaaca | 1440 |
| aacttggcaa tggccattgc taaaagtgtt ccagtatatg gcatggttaa ctggaataat | 1500 |
| gaaaactttc catttaatga tgtagcagga aaaagcttgg tggtctggga tgaaggtatt | 1560 |
| attaagtcta caattgtaga agctgcaaaa gccattttag gcgggcaacc caccagggta | 1620 |
| gatcaaaaaa tgcgtggaag tgtagctgtg cctggagtac ctgtggttat aaccagcaat | 1680 |
| ggtgacatta cttttgttgt aagcgggaac actacaacaa ctgtacatgc taaagcctta | 1740 |
| aaagagcgca tggtaaagtt aaactttact gtaagatgca gccctgacat ggggttacta | 1800 |
| acagaggctg atgtacaaca gtggcttaca tggtgtaatg cacaaagctg ggaccactat | 1860 |
| gaaaactggg caataaacta cacttttgat ttccctggaa ttaatgcaga tgccctccac | 1920 |

```
ccagacctcc aaaccacccc aattgtcaca gacaccagta tcagcagcag tggtggtgaa    1980
agctctgaag aactcagtga aagcagcttt tttaacctca tcaccccagg cgcctggaac    2040
actgaaaccc cgcgctctag tacgcccatc cccgggacca gttcaggaga atcatttgtc    2100
ggaagcccag tttcctccga agttgtagct gcatcgtggg aagaagcctt ctacacacct    2160
ttggcagacc agtttcgtga actgttagtt ggggttgatt atgtgtggga cggtgtaagg    2220
ggtttacctg tgtgttgtgt gcaacatatt aacaatagtg ggggagggtt gggactttgt    2280
ccccattgca ttaatgtagg ggcttggtat aatggatgga aatttcgaga atttacccca    2340
gatttggtgc gatgtagctg ccatgtggga gcttctaatc ccttttctgt gctaacctgc    2400
aaaaaatgtg cttacctgtc tggattgcaa agctttgtag attatgagta aaaaagtgg     2460
caaatggtgg gaaagtgatg ataaatttgc taaagctgtg tatcagcaat ttgtggaatt    2520
ttatgaaaag gttactggaa cagacttaga gcttattcaa atattaaaag atcattataa    2580
tatttcttta gataatcccc tagaaaaccc atcctctctg tttgacttag ttgctcgtat    2640
taaaaataac cttaaaaact ctccagactt atatagtcat cattttcaaa gtcatggaca    2700
gttatctgac cacccccatg ccttatcatc cagtagcagt catgcagaac ctagaggaga    2760
aaatgcagta ttatctagtg aagacttaca caagcctggg caagttagcg tacaactacc    2820
cggtactaac tatgttgggc ctggcaatga gctacaagct gggcccccgc aaagtgctgt    2880
tgacagtgct gcaaggattc atgactttag gtatagccaa ctggctaagt tgggaataaa    2940
tccatatact cattggactg tagcagatga agagctttta aaaatataaa aaatgaaac     3000
tgggtttcaa gcacaagtag taaaagacta ctttactttta aaaggtgcag ctgcccctgt    3060
ggcccatttt caaggaagtt tgccggaagt tcccgcttac aacgcctcag aaaaatacc     3120
aagcatgact tcagttaatt ctgcagaagc cagcactggt gcaggagggg ggggcagtaa    3180
ttctgtcaaa agcatgtgga gtgagggggc cacttttagt gctaactctg taacttgtac    3240
attttccaga cagtttttaa ttccatatga cccagagcac cattataagg tgttttctcc    3300
cgcagcgagt agctgccaca atgccagtgg aaaggaggca aaggtttgca ccatcagtcc    3360
cataatggga tactcaaccc catggagata tttagatttt aatgctttaa atttattttt    3420
ttcaccttta gagtttcagc acttaattga aaattatgga agtatagctc ctgatgcttt    3480
aactgtaacc atatcagaaa ttgctgttaa ggatgttaca gacaaaactg agggggggt     3540
acaggttact gacagcacta cagggcgcct atgcatgtta gtagaccatg aatacaagta    3600
cccatatgtg ttagggcaag gtcaggatac tttagcccca gaacttccta tttgggtata    3660
cttccccct caatatgctt acttaacagt aggagatgtt aacacacaag gaatttctgg     3720
agacagcaaa aaattagcaa gtgaagaatc agcatttat gttttggaac acagttcttt     3780
tcagctttta ggtacaggag gtacagcatc tatgtcttat aagtttcctc cagtgcccc     3840
agaaaattta gagggctgca gtcaacactt ttatgaaatg tacaatccct tatacggatc    3900
ccgcttaggg gttcctgaca cattaggagg tgacccaaaa tttagatctt taacacatga    3960
agaccatgca attcagcccc aaaacttcat gccagggcca ctagtaaact cagtgtctac    4020
aaaggaggga gacagctcta atactggagc tggaaaagcc ttaacaggcc ttagcacagg    4080
tacctctcaa aacactagaa tatccttacg ccctgggcca gtgtctcagc cataccacca    4140
ctggacacaa ataaatatg tcacaggaat aaatgccatt tctcatggtc agaccactta     4200
tggtaacgct gaagacaaag agtatcagca aggagtgggg agatttccaa atgaaaaaga    4260
acagctaaaa cagttacagg gtttaaacat gcacacctac tttcccaata aaggaaccca    4320
```

```
gcaatataca gatcaaattg agcgccccct aatggtgggt tctgtatgga acagaagagc    4380
ccttcactat gaaagccagc tgtggagtaa aattccaaat ttagatgaca gttttaaaac    4440
tcagtttgca gccttaggag gatggggttt gcatcagcca cctcctcaaa tattttaaa    4500 aatattacca caaagtgggc caattggagg tattaaatca atgggaatta ctaccttagt    4560
tcagtatgcc gtgggaatta tgacagtaac tatgacattt aaattggggc cccgtaaagc    4620
tacgggacgg tggaatcctc aacctggagt atatcccccg cacgcagcag gtcatttacc    4680
atatgtacta tatgaccccca cagctacaga tgcaaaacaa caccacagac atggatatga    4740
aaagcctgaa gaattgtgga cagccaaaag ccgtgtgcac ccattgtaaa cactccccac    4800
cgtgccctca gccaggatgc gtaactaaac gcccaccagt accacccaga ctgtacctgc    4860
cccctcctgt acctataaga cagcctaaca caaaagatat agacaatgta gaatttaagt    4920
acttaaccag atatgaacaa catgttatta gaatgttaag attgtgtaat atgtatcaaa    4980
atttagaaaa ataaacattt gttgtggtta aaaaattatg ttgttgcgct ttaaaaattt    5040
aaaagaagac accaaatcag atgccgccgg tcggccggta ggcgggactt ccggtacaag    5100
atggcggaat tc                                                       5112
```

<210> SEQ ID NO 131
<211> LENGTH: 4844
<212> TYPE: DNA
<213> ORGANISM: Erythrovirus B19

<400> SEQUENCE: 131

```
ttttaaattt tcgcgggctt ttccccgcct tatgcaaatt acctgccatg tttaatgctt      60
tattttaatt tgattggaca aaaagttaac ggttttatg ggcggagtta cgcaaggtat     120
ataagcagat gaattttgta aactttctt tcctggctgc ttttactgg ggataacttg     180 ctgttatttg cctgctaatt aacaggtatt tatactaact tttaatttac taacatggag    240
ctatttaggg gtgtgttgca tatttcctct aacatttttag actgtgctaa tgataactgg    300
tggtgctcta tgctggattt agatacttct gactgggaac cactaactca ctctaacaga    360
ctaatggcaa tatatttaag taatgttgct tctaaactgg attttactgg ggggccgctg    420
gcgggttgct tatacttttt tcaggtggaa tgtaacaaat ttgaggaagg ctaccatatt    480
catgtagtta ttggtggtcc aggacttaat gctagaaact taacagtgtg tgtagaaggc    540
ttgtttaata atgtgcttta ccacctggta aatgaaagtg ttaaactgaa attttgcca    600 ggaatgacta caaaaggaaa gtattttaga gatggagagc agtttatga aaattaccta    660 atgaaaaaaa ttccttttaaa tgttgtgtgg tgtgtaacaa atattgacgg gtatatagac    720
acctgtattt ctgcatcttt tagacgagga gcttgccatg ctaaaaaacc tcgaattagt    780
acaaacacag acactgtaaa taatgaagga ggggaatcaa gctgtggagg gggagatgtg    840
gtgccatttg ccgggaaggg aaccaaggca ggcttaaagt tcaaacaat ggtaaattgg    900 ctatgtgaaa acagagtgtt tactgaagac aaatggaagt tagtggattt taatcagtat    960
acattattaa gcagtagtca tagtgggagt tttcaaatac aaagtgcatt aaagctagct   1020
atttataaag ctactaactt agttcctact agtacatttt taatgcattc agactttgag   1080
caggttacct gcattaaaga aaataaaata gttaaactat tattatgcca gaattatgat   1140
cctcttttag tgggtcaaca tgttttaaag tggattgaca aaaaatgtgg taaaaaaaac   1200
accctgtggt tttacgggcc cccaagtact ggaaaaacaa atttggcaat ggctattgct   1260
```

```
aaaactgtcc cagtgtatgg catggttaat tggaataatg aaaattttcc atttaatgat    1320
gtagcgggga aaagtttggt ggtctgggat gaaggcatta ttaagtccac tattgtggaa    1380
gctgcaaaag ccattttagg tgggcagcca accagggtag atcaaaaaat gcgtggcagt    1440
gtggcagtgc ctggtgtgcc agtggtaata accagcaatg gtgacattac ctttgttgta    1500
agtggtaata ccactacaac tgtccatgct aaagccttaa aggagcgaat ggtaaagcta    1560
aactttaccg taagatgcag ccctgacatg ggcttactta cagaggctga tgtacagcaa    1620
tggctaactt ggtgtaatgc acaaagctgg aaccactatg aaaactgggc aataaactac    1680
acgtttgatt tccctggaat aaatgcagat gccctccacc cagacctcca aaccgtcccc    1740
attgtcgcag acaccagtgt cagcagcagt ggtggtgaaa gctctgaaga actcagtgaa    1800
agcagctttt tcaacctcat cactcccggc gcctggaaca gtgaaacccc gcgctctagt    1860
acacccgtcc ccgggaccag ttcaggagaa tcatttgtcg gaagcccagt ttcctccgaa    1920
gtggtagccg cgtcgtggga ggaagccttt tacactccac ttgcagacca gtttcgtgaa    1980
ctgttagttg gggttgacta tgtgtgggat ggtgtgaggg gattgcctgt ttgttgtgtg    2040
cagcatatta ataatagtgg gggagggtta ggcctttgtc ctcattgtat taatgtggga    2100
gcttggtata atggatggaa gtttcgtgaa tttactccag atttggtacg gtgcagctgc    2160
catgtaggag cttctaatcc cttttctgtg ttaacctgca aaaaatgtgc ttacttgtct    2220
ggattacaga gttttgtgga ttatgagtaa aaaaagtgac aagtggtggg aaagtgatga    2280
taaatttgct aaggacgtgt ataagcaatt tgtagaattt tatgaaaaag ttactgagac    2340
agacttagag cttattcaaa tattaaaaga tcattataat atttctttag ataatcccctt    2400 agaaaaccca tcttccctgt ttgacttagt tgctcgtatt aaaagtaatc ttaaagacac    2460
tccagaccta tatagtcatc attttcaaag tcatggacag ttatttgacc accccatgc    2520 cttatcaccc agtagcagtc atacagaacc tagaggagaa gatgcagtat tatctagtga    2580
agacttacac aagcctgggc gagttagcat acaactaccc ggtactaact atattgggcc    2640
tggcaatgag ctacaagctg gccccccgca aagtgctgtg gatagtgctg caaggattca    2700
tgactttagg tatagccaat tggctaagct gggaataaat ccatatactc attggactgt    2760
agcagatgag gaactgttaa aaaatataaa aaatgaaact gggtttcaag cacaagcagt    2820
aaaagattac tttactttaa aaggtgcagc tgccccctgtg gcccatttc aaggaagttt    2880 gccggaagtt cccgcataca acgcctcaga aaagtaccca agcatgactt cagttaattc    2940
tgcagaagcc agcactggtg caggagggggg aggcagtaat cctgtcaaaa gcatgtggag    3000
tgagggcgcc acttttactg ccaactctgt aacttgtaca ttttccagac agttttaat    3060 cccatatgac ccagagcacc attataaagt gttttctccc gcagctagta gctgccataa    3120
tgccagtggg aaagaggcaa aggtttgcac tattagtccc ataatgggct actcaacgcc    3180
atggagatac ttagacttta atgctttaaa cttattttt tcaccttag aatttcaaca    3240 tttaattgaa aattatggaa gtatagcccc tgatgcttta actgttacca tatcagaaat    3300
tgctgttaaa gatgttacag acaaaacagg aggagggtg caggttactg acagtactac    3360
agggcgttta tgcatgttag tagatcatga gtacaagtat ccatatgtgt taggtcaggg    3420
acaggatacc ttagccccag aactgcctat ttgggtgtac tttccccctc aatatgctta    3480
tttaaccgtg ggagatgtaa acacacaggg aatttcaggg gacagtaaaa agctagcaag    3540
tgaagaatca gcattttatg ttttggaaca cagttcattt gaactgttag gtacaggtgg    3600
ctctgccact atgtcctata aatttccacc agtgcccca gaaaacttgg agggttgtag    3660
```

```
ccaacacttt tatgaaatgt acaaccccct gtatgggtct cgtttagggg tacctgacac    3720
actagggggg gaccctaaat ttagatcatt aactcacgaa gatcatgcaa ttcagccaca    3780
aaactttatg cctggcccac tagtaaactc agtgtccact aaagagggag acacttccaa    3840
tacaggcgcc ggaaaagccc ttacggggct tagtactggc actagtcaaa gcaccagaat    3900
atccctgcgc ccaggaccag tgtctcagcc ataccattac tgggacactg ataagtatgt    3960
cacaggaata aatgctattt cacacggaca aaccacttat ggaaatgctg aagacaaaga    4020
gtatcagcaa ggggtaggaa gattcccaaa tgaaaagag caacttaaac agttacaagg    4080
cctaaacatt cacacatact ttccaaacaa aggaacccaa caatacacag atcaaattga    4140
acgcccctta atggtagggt ctgtgtggaa cagaagagct cttcattatg agagtcagct    4200
gtggagtaaa atcccccaact tagatgacag ttttaaaacc caatttgcag ccctgggcgg    4260
gtggggttta catcaaccac ctcctcaaat attttttaaaa atactgccac aaagtggacc    4320
aattgggggt attaaatcca tgggaatcac taccctagtt caatatgcag tgggaattat    4380
gacagttact atgacatttta aattgggacc tcgtaaggct actggtaggt ggaatccaca    4440
gcctggagtg tatcctcctc atgcagctgg tcatttacca tatgtactgt atgaccctac    4500
agctacagat gcaaaccaac accacaaaca cggatatgaa aagcctgaag aattgtggac    4560
tgccaaaagc cgtgtgcacc cattgtaaac actccccacc gtgtcctcag ccaggaaccg    4620
taaccaaccg tcctcctgta ccacccagat tatatgtgcc cccgccaata ccccgcagag    4680
aaccgcttgt aaaagataca aatgctgtag aatataagtt actaacccgt tatgaacaac    4740
atgtaattag aatgcttaga ttgtgtaata tgtatacaaa tttggaaaaa taaataactt    4800
aaataaatag ctaatagtgt atgttacttt aaaaatttttt aaaa                   4844

<210> SEQ ID NO 132
<211> LENGTH: 5028
<212> TYPE: DNA
<213> ORGANISM: Erythrovirus B19

<400> SEQUENCE: 132
gacgtcacag gaaatgacgt aactgtccgc catcttgtac cggaagtccc gcctaccggc      60
ggcgaccggc ggcatctgat ttggtgtctt cttttttgaaa ttttggcggg cttttttcccg    120 ccttatgcaa ataagcggcc atgtttaatg ttatatttta atttaattgg acaaacgcct     180
aacggttact aggggcggag ttacgggcgg tatataagca gctgcgttcc ctgacacttt     240
cttttctggt tgcttttgac tggaactcac ttgctgttct ttgcctgcta agtaacaggt     300
atttatacta acttttaatt tactaacatg gagctatttc ggggtgtctt gcacatttcc     360
tctaacattc tggactgtgc taatgataac tggtggtgct ctatgctaga cttagatact     420
tctgactggg aaccactaac ccattctaac agattaatgg caatatattt aagcagtgtt     480
gcttctaaac ttgattttac tggggggccg ctagcaggtt gcttatactt ttttcaggtg     540
gaatgtaaca aatttgagga aggctatcat atccatgtag ttattggtgg tccaggacta     600
aatgctagaa acttaactgt gtgcgtagaa ggtttattta ataatgttct ttaccatctt     660
gtaactgaaa gtgttaaact taaattttttg ccagggatga ctaccaaagg aaaatatttt    720
agagatggag agcagtttat agaaaattac ttaatgaaaa aaattccttt aaatgttgtg     780
tggtgtgtaa caaatattga cgggtatata gacacctgta tttccgcctc ttttcggcga    840
ggagcttgtc atgctaaaag accccgcatt actgcaaata cagacagtgc tactaatgaa    900
```

```
actgggagt ctagctgtgg aggggagat gttgtgccat tcgctggaaa gggaacaaaa      960
gcggggttaa agtttcaaac catggtaaat tggctatgtg aaaacagagt atttactgaa     1020
gataaatgga aattagtgga ttttaaccaa tatactttat taagtagcag tcacagtggc     1080
agctttcaaa ttcaaagtgc cttaaagtta gctatttata aagctactaa cttagtaccc     1140
actagtacat tcttgttaca ttcagacttt gagcaggtta cttgcattaa agaaaataaa     1200
atagtaaaat tattattgtg tcaaaactat gatcctcttt tagtgggtca acatgtgtta     1260
aggtggattg acaaaaaatg tggtaaaaaa aacaccctgt ggttttacgg gccaccaagt     1320
actggaaaaa caaatttggc aatggctatt gctaaaactg taccagtgta tggaatggtg     1380
aattggaata atgaaaactt tccatttaat gatgtagcgg ggaaaagttt ggtggtctgg     1440
gatgaaggca ttattaagtc cactattgtg gaagctgcaa aagccatttt aggtggtcag     1500
ccaaccaggg tagatcagaa aatgcgtggc agtgtggcag tgcccggtgt gcctgtggtt     1560
ataaccagca atggtgacat tacatttgtt gtgagtggta ataccactac aactgtgcat     1620
gctaaagcct taaaggaacg gatggtaaag ctaaacttta ccataagatg tagccctgac     1680
atgggtttac ttacagaggc tgatgtacaa caatggctaa cttggtgtaa tgcacaaagc     1740
tggagccact atgaaaactg ggcaataaac tacacatttg atttccctgg aataaatgca     1800
gatgccctcc acccagatct ccaaaccacc cccattgtcc cagacaccag tatcagcagc     1860
agtggtggtg aaagctctga agaactcagt gaaagcagct ttttcaacct catcactcca     1920
ggcgcctgga acagtgaaac cccgcgctct agtacgcccg tccccgggac cagttcagga     1980
gaatcatttg tcgaagccc agtttcctcc gaagtggtag ccgcgtcgtg ggaggaagct     2040
ttttacacgc cgcttgccga tcagtttcgt gaactgttag tagggggttga ctttgtatgg     2100
gatggtgtga gggggattgcc tgtttgctgt gtggaacata taaacaacag tgggggaggg    2160
ttggggcttt gccctcattg tattaatgtg ggagcttggt ataatggatg gaaatttaga     2220
gagtttactc cagacttagt gcgctgcagt tgtcatgtag gagcctctaa cccatttttct   2280
gtgttaactt gtaaaaaatg tgcttacctg tctggattac aaagttttgt agattatgag     2340
taaaaccact aacaaatggt gggaaagcag tgacaaattt gcccaggacg tgtataagca     2400
gtttgtgcaa ttttatgaaa aagctactgg aacagactta gagcttattc aaattttaaa     2460
agaccattac aacatttctt tagataatcc tttagaaaac ccctcttctt tatttgactt     2520
agttgctcgc attaaaagta atcttaaaaa ctctccagac ctatatagtc atcattttca     2580
gagccatgga cagttatctg accacccca tgccttatca tccagtaaca gtagtgcaga     2640
acctagagga gaaaatgcag tattatctag tgaagactta cacaagcctg gcaagttag     2700
catacaatta cccggtacta actatgttgg gcctggcaat gagctacaag ctgggcctcc     2760
gcagaatgct gtggacagtg ctgcaaggat tcatgacttt aggtatagcc aattggctaa     2820
gttgggaata aatccttata cacattggac ggtagcagat gaagaattgt taaaaaatat     2880
aaaaaatgaa acagggtttc aagcacaagc agtaaaagat tactttacttt taaaaggtgc    2940
agctgcccct gtggcccatt ttcaaggaag tttaccggaa gtgccgcgt acaacgcctc     3000
agaaaaatac cccagcatga cttcagttaa ctctgcagaa gccagcactg gtgcaggcgg     3060
gggaggtagc aaccctacaa aaagcatgtg gagtgaaggg gctacatttta ctgctaattc    3120
tgtaacgtgt acattctcta ggcaattttt aattccatat gatccagagc atcattataa     3180
agtgttctct ccagcagcta gtagctgcca caatgctagt ggggaaagagg caaaagtgtg    3240
cactattagt cccattatgg ggtactctac tccgtggaga tacttagatt ttaatgcttt     3300
```

```
aaatttgttt ttctcaccat tagagtttca gcacttaatt gaaaattatg gtagtatagc    3360
tccagatgct ttaactgtaa ctatttcaga aattgctgta aaagatgtca cagacaaaac    3420
aggaggaggt gtgcaagtta ctgacagcac cacaggacgt tgtgtatgt tagtggatca    3480 tgagtataaa tacccatatg tgctaggtca gggacaagac acactagctc cagaactgcc    3540
catttgggtt tactttcccc cccagtatgc ttacttaaca gtaggtgaag taaacacaca    3600
aggaatttca ggagacagca aaaaattggc tagtgaagaa tcagcttttt atgtgttaga    3660
gcacagttca tttgaacttt tgggtacagg gggatctgcc actatgtcct acaaatttcc    3720
agctgtgccc ccagaaaacc tagaaggctg cagccaacat tttttatgaaa tgtacaaccc    3780 tttgtacggt tctcgtttag gggtacctga cacattagga ggggacccta aatttagatc    3840
attgacacac gaagaccacg caattcagcc acaaaacttt atgcctgggc cactaataaa    3900
ttcagtgtct accaaagaag gagacaattc taatacaggt gctggaaaag cccttacggg    3960
gcttagtact ggcactagcc aaaacaccag aatttcccta cgccccgggc cagtatctca    4020
gccataccat cactgggaca ctgataaata tgttacagga ataaatgcca tttcacatgg    4080
acaaaccact tatggaaatg ctgaggacaa agagtatcag caaggggtag gaagatttcc    4140
aaatgaaaaa gaacagctta agcagttaca aggtcttaac atgcacacat acttccctaa    4200
taaaggaacc caacaataca cagaccaaat tgaacgccct cttatggtgg gctctgtttg    4260
gaacagaaga gctcttcact atgaaagtca gctgtggagt aaaatcccta acttagatga    4320 cagtttttaaa actcaatttg cagccctagg cgggtgggg ttgcatcaac cacccctca    4380 aatattttta aaaatactac cacaaagtgg gccaattgga ggtattaaat ccatgggaat    4440
tactacttta gttcaatatg ctgtgggaat aatgacagtt accatgacct ttaaattggg    4500
acctcgaaag gctactggaa ggtggaatcc ccagcctggc gtttatcctc ctcatgcagc    4560
tggtcattta ccatatgtac tgtatgaccc cacagctaca gatgcaaagc aacaccacag    4620
acacggatat gaaaagcctg aagaattgtg gactgccaaa agccgtgtgc acccattgta    4680
aacattcccc accgtgtcct cagccaggaa ccgtcaccca ccgccacct gtgccgccca    4740 gattatatgt gcccctcca ataccccgta ggcaaccatc tataaaagat acagacgctg    4800
tagaatataa attattaact agatatgaac aacatgtaat tagaatgcta agattatgta    4860
atatgtacac aagtttggaa aaataaaagc cttaaataaa taattcatag tgtatggttc    4920
tttaaaaatt tcaaaagaa gacaccaaat cagatgccgc cggtcgccgc cggtaggcgg    4980
gacttccggt acaagatggc ggacagttac gtcatttcct gtgacgtc                 5028

<210> SEQ ID NO 133
<211> LENGTH: 5017
<212> TYPE: DNA
<213> ORGANISM: Erythrovirus B19

<400> SEQUENCE: 133
acaggaaatg acgtaactgt ccgccatctt gaaccggaag tcccgcctac cggcggcgac       60
cggcggcatc tgatttggtg tcttcttttt aaaattttg gcgggctttt tcccgcctta      120
tgcaaatgaa cagccatgtt tggtgtatta ttttaatttt attggacaca ggcctaacgg      180
ttattatagg cggagttacg gacagtatat aagcagctga gtttcgtgac actttctttt      240
ctggttgctt cttactggaa ctcacttgct gttatttgcc tgctaactaa caggtattta      300
tactaacttt taacttacta acatggaact atttagggg gtgctgcaca tttcctctaa      360
```

```
cattctggac tgcgctaatg ataactggtg gtgctctatg ctggacctag acacttctga      420
ctgggagcca ctaacccact ctaacagact catggcaata tatttaagca gcgttgcttc      480
taagcttgat tttactgggg ggccactggc aggttgctta tacttttttc aggtggaatg      540
taacaaattt gaggaaggct atcacattca tgtggttatt ggtggtccag gactgaatgc      600
tagaaattta actgtgtgtg tagaaggttt atttaataat gttctttacc atcttgtaac      660
tgaaactgtt aaacttaaat ttttgccagg gatgactact aaaggaaaat attttagaga      720
tggagagcag tttatagaaa attacttaat gaaaaaaatt cctttaaatg ttgtgtggtg      780
tgtaacaaat attgacgggt atatagacac ctgtatttct gcctcttttc ggcgaggagc      840
ctgtcatgct aaaagacccc gcattactgc aaatacagac aatgttacta gtgaaaccgg      900
ggagtctagc tgtggagggg gagatgttgt accatttgct ggaaagggaa caaaggcagg      960
gttaaagttt caaccatgg taaattggct atgtgaaaac agagtattta ctgaggataa      1020
atggaaatta gtagatttta accaatatac tttattaagc agtagtcaca gtggcagctt      1080
tcagatacaa agtgcattaa agttagctat ctataaagcc actaacttag tacctactag      1140 cactttttg ttacattcag actttgagca ggttacttgc attaaagata ataaaatagt      1200
taaattgtta ctgtgccaaa actatgatcc tcttctagta gggcaacatg tgttaaagtg      1260
gattgacaaa aaatgtggta aaaaaaacac cttgtggttt tacgggccac caagtactgg      1320
aaaaacaaat ttggctatgg ctattgccaa aactgttcca gtgtatgcca tggttaattg      1380
gaataatgaa aactttccat ttaatgatgt agcgggaaaa agtttggtgg tctgggatga      1440
aggcataatt aaatccacta ttgtggaagc tgcaaaagcc attttaggtg gccagccaac      1500
cagggtagat caaaaaatgc gtggcagtgt ggcagtgcct ggtgtgcctg tggttataac      1560
cagcaatggt gacattacct ttgttgtaag tggtaatacc actacaactg tgcatgctaa      1620
agccttaaaa gaaaggatgg taaagctaaa ctttaccgta agatgcagcc ctgacatggg      1680
cttacttaca gaggctgatg tgcagcaatg gctaacttgg tgtaatgcac aaagctggaa      1740
ccactatgaa aactgggcaa taaactacac gtttgatttc cctggaataa atgcagatgc      1800
cctccaccca gacctccaaa ccaccccat tgtcccagac accagtatca gcagcagtgg      1860
tggtgaaagc tctgaagaac tcagtgaaag cagctttttc aacctcatca ctccaggcgc      1920
ctggaacagt gaaaccccgc gctctagtac gcccgtcccc gggaccagtt caggagaatc      1980
atttgtcgga agcccagttt cctccgaagt ggtagccgcg tcgtgggagg aagcctttta      2040
cacgccactt gcagatcagt ttcgtgaact gttagtaggg gttgactttg tatgggatgg      2100
tgtgagggga ttgcctgttt gttgtgtgga acatattaat aacagtgggg gagggttggg      2160
gctttgtcct cattgtatta atgtgggagc ttggtataat ggatggaaat ttagagagtt      2220
tactccagac ttagtgcgct gtagttgtca tgtaggagct tctaacccat ttctgtgtt      2280 aacttgtaag aaatgtgctt acctgtctgg attacaaagc tttgtagatt atgagtaaaa      2340
ccactgacag atggtgggaa agtaatgaca catttgccca ggacgtgtat aagcaatttg      2400 tacaattta tgaaaagtc actggtacag atttagaact tattcaaatt ttaaaagatc      2460
attataacat ttctttagat aatcctttag agaaccctc ttccttattt gacttagttg      2520
ctcgcattaa aagtaatctt aaaaactctc cagacctata tagtcatcat tttcagagcc      2580
atggacagtt atctgaccac ccccatgcct tatcatccag taacagtagt acagaaccta      2640
gaggagaaaa tgcagtatta tctaatgaag acttacacaa gcctgggcaa gttagcatgc      2700
aactacccgg tactaactat gttgggcctg gcaatgagtt acaagctggg cctccgcaga      2760
```

```
atgctgtgga cagtgctgca aggattcatg actttaggta tagccaattg gctaagttgg    2820
gaataaaccc ttatactcac tggacggtag cagacgaaga gttgttaaaa aatataaaaa    2880
atgaaacagg gtttcaagca caagcagtaa aagattactt tactttaaaa ggtgcagctg    2940
cccctgtggc ccattttcaa ggaagtttac cggaagtgcc cgcgtacaac gcctcagaaa    3000
aatacccag catgacttca gttaactctg cagaagccag cactggtgca ggcggggag    3060
ggagcaaccc tacaaaaagc atgtggagtg aagggctac atttactgct aattctgtaa    3120
catgcacatt ctctaggcag ttttaattc catatgaccc agagcatcat tataaagtat    3180
tttctccagc agccagtagc tgccacaatg ctagtgggaa agaggcaaaa gtgtgcacta    3240
ttagtcctat tatgggatac tctactccgt ggagatactt agattttaat gctttgaatt    3300
tgttttttc accactagag tttcagcact taattgagaa ttatggcagt atagctccag    3360
atgctttaac tgtaactatt tcagaaattg ctgttaaaga tgttacagac aaaacaggag    3420
gaggtgtgca agtaactgac agcaccacag gacgtttgtg tatgttagtg gaccatgaat    3480
ataagtaccc atatgtgctg ggtcagggac aagacacatt agctccagaa ctgcctatt    3540
gggtgtactt tcctccccag tatgcttact aacagtagg tgaagtaaac acacaaggag    3600
tttcaggaga cagcaaaaaa ttggctagtg aagaatcagc ttttatgtt ttggaacaca    3660
gctcctttca actttaggt acaggtggct ctgctacaat gtcctataaa tttccagccg    3720
tgcccccaga aaacttagag ggctgcagtc agcatttta tgaaatgtac aacccctgt    3780
atggttctcg tttaggagtg cctgacacat taggagggga ccctaaattt agatcattaa    3840
cacacgagga ccacgcaatt cagccacaaa actttatgcc tgggccactg attaactcag    3900
tgtctaccaa agaaggagac acctctaata caggtgctgg aaaagccctt acggggctta    3960
gtactggcac tagtcaaagc accagaattt ccctgcgccc aggtccagtg tctcagccat    4020
accatcactg ggacactgat aaatatgtaa caggaataaa tgccatctca catggacaaa    4080
ccacttatgg aaatgctgaa gacaaagagt atcagcaagg ggtaggaagg tttccaaatg    4140
aaaaagaaca acttaagcag ttacaagggc taaacatgca cacatacttt cctaataaag    4200
gtacccaaca atacacagat caaattgaaa gacctttaat ggtgggctct gtgtggaaca    4260
gaagagctct tcactatgaa agtcagttat ggagtaaaat ccctaactta gatgatagtt    4320
ttaaaactca atttgcagcg ttaggcgggt ggggattgca ccaaccaccc cctcaaatat    4380
ttttaaaaat actaccgcaa agtgggccca ttggaggtat taaatccatg ggaattacta    4440
ctttagtcca gtatgctgta ggaattatga cagtcactat gacatttaaa ttgggacctc    4500
gaaaagccac tggaaggtgg aatcctcaac ctggagttta ccctcctcat gcagctggtc    4560
atttaccata tgtactgtat gaccccacag ctacagatgc aaagcaacac cacagacacg    4620
gatatgaaaa gcctgaagaa ttgtggactg ccaaaagccg tgtgcaccca ctgtaaacat    4680
tccccaccgt gtcctaagcc aggaaccgtc acccaccgtc cacctgtacc gcctagatta    4740
tatgtgcccc ctcctgtacc cagtaggcaa ccatctgtaa aagatacaga cgctgtagaa    4800
tataaattgc taactagata tgaacaacat gtaattagaa tgcttagatt atgtaatatg    4860
tacacaaatt tggaaaaata aaagcctaaa ataataact aatagtgtat gttgctttaa    4920
aaattttaaa aagaagacac caaatcagat gccgccggtc gccgccggta ggcgggactt    4980
ccggttcaag atggcggaca gttacgtcat ttcctgt                              5017
```

<210> SEQ ID NO 134

<211> LENGTH: 50
<212> TYPE: DNA
<213> ORGANISM: Erythrovirus B19

<400> SEQUENCE: 134
tcagcagcag tggtggtgaa agctctgaag aactcagtga aagcagcttt    50

<210> SEQ ID NO 135
<211> LENGTH: 18
<212> TYPE: DNA
<213> ORGANISM: Erythrovirus B19

<400> SEQUENCE: 135
cttaaaaact ctccagac    18

<210> SEQ ID NO 136
<211> LENGTH: 17
<212> TYPE: DNA
<213> ORGANISM: Erythrovirus B19

<400> SEQUENCE: 136
tgaaaccccg cgctcta    17

<210> SEQ ID NO 137
<211> LENGTH: 21
<212> TYPE: DNA
<213> ORGANISM: Erythrovirus B19

<400> SEQUENCE: 137
aactaacagt tcacgaaact g    21

<210> SEQ ID NO 138
<211> LENGTH: 23
<212> TYPE: DNA
<213> ORGANISM: Erythrovirus B19

<400> SEQUENCE: 138
tccccgggac cagttcagga gaa    23

<210> SEQ ID NO 139
<211> LENGTH: 17
<212> TYPE: DNA
<213> ORGANISM: Erythrovirus B19

<400> SEQUENCE: 139
tcagcagcag tggtggt    17

<210> SEQ ID NO 140
<211> LENGTH: 17
<212> TYPE: DNA
<213> ORGANISM: Erythrovirus B19

<400> SEQUENCE: 140
tagagcgcgg ggtttca    17

<210> SEQ ID NO 141
<211> LENGTH: 34
<212> TYPE: DNA
<213> ORGANISM: Erythrovirus B19

<400> SEQUENCE: 141
tgaaagctct gaagaactca gtgaaagcag cttt    34

```
<210> SEQ ID NO 142
<211> LENGTH: 18
<212> TYPE: DNA
<213> ORGANISM: Erythrovirus B19

<400> SEQUENCE: 142
aatgcagatg ccctccac                                                   18

<210> SEQ ID NO 143
<211> LENGTH: 29
<212> TYPE: DNA
<213> ORGANISM: Erythrovirus B19

<400> SEQUENCE: 143
tcagcagcag tggtggtgaa agctctgaa                                       29

<210> SEQ ID NO 144
<211> LENGTH: 15
<212> TYPE: DNA
<213> ORGANISM: Erythrovirus B19

<400> SEQUENCE: 144
tgttccaggc gcctg                                                      15

<210> SEQ ID NO 145
<211> LENGTH: 18
<212> TYPE: DNA
<213> ORGANISM: Erythrovirus B19

<400> SEQUENCE: 145
cacagctaca gatgcaaa                                                   18

<210> SEQ ID NO 146
<211> LENGTH: 16
<212> TYPE: DNA
<213> ORGANISM: Erythrovirus B19

<400> SEQUENCE: 146
ggtgcacacg gctttt                                                     16

<210> SEQ ID NO 147
<211> LENGTH: 30
<212> TYPE: DNA
<213> ORGANISM: Erythrovirus B19

<400> SEQUENCE: 147
tgtccacaat tcttcaggct tttcatatcc                                      30

<210> SEQ ID NO 148
<211> LENGTH: 30
<212> TYPE: DNA
<213> ORGANISM: Erythrovirus B19

<400> SEQUENCE: 148
tggatatgaa aagcctgaag tattgtggac                                      30

<210> SEQ ID NO 149
<211> LENGTH: 20
<212> TYPE: DNA
<213> ORGANISM: Erythrovirus B19

<400> SEQUENCE: 149
ggtcatttac catatgtact                                                 20
```

```
<210> SEQ ID NO 150
<211> LENGTH: 30
<212> TYPE: DNA
<213> ORGANISM: Artificial
<220> FEATURE:
<223> OTHER INFORMATION: Description of Artificial Sequence: synthetic
      oligonucleotide; n is a universal base analogue
<220> FEATURE:
<221> NAME/KEY: misc_feature
<222> LOCATION: (16)..(16)
<223> OTHER INFORMATION: Description of Artificial Sequence: synthetic
      oligonucleotide; n is a universal base analogue

<400> SEQUENCE: 150
agctacagat gcaaancaac accacagaca                                    30

<210> SEQ ID NO 151
<211> LENGTH: 23
<212> TYPE: DNA
<213> ORGANISM: Erythrovirus B19

<400> SEQUENCE: 151
gaaaactttc catttaatga tgt                                           23

<210> SEQ ID NO 152
<211> LENGTH: 20
<212> TYPE: DNA
<213> ORGANISM: Erythrovirus B19

<400> SEQUENCE: 152 atttttttgat ctaccctggt                                              20

<210> SEQ ID NO 153
<211> LENGTH: 20
<212> TYPE: DNA
<213> ORGANISM: Erythrovirus B19

<400> SEQUENCE: 153
ttggtggtct gggatgaagg                                               20

<210> SEQ ID NO 154
<211> LENGTH: 19
<212> TYPE: DNA
<213> ORGANISM: Erythrovirus B19

<400> SEQUENCE: 154
ttttatgggc cgccaagta                                                19

<210> SEQ ID NO 155
<211> LENGTH: 20
<212> TYPE: DNA
<213> ORGANISM: Erythrovirus B19

<400> SEQUENCE: 155
ttcatcccag accaccaagg                                               20

<210> SEQ ID NO 156
<211> LENGTH: 29
<212> TYPE: DNA
<213> ORGANISM: Erythrovirus B19

<400> SEQUENCE: 156
atggctattg ctaaaactgt tccagtgta                                     29
```

```
<210> SEQ ID NO 157
<211> LENGTH: 34
<212> TYPE: DNA
<213> ORGANISM: Erythrovirus B19

<400> SEQUENCE: 157
tggaataatg aaaactttcc atttaatgat gtag                          34

<210> SEQ ID NO 158
<211> LENGTH: 26
<212> TYPE: DNA
<213> ORGANISM: Erythrovirus B19

<400> SEQUENCE: 158
caatggccat tgctaaaagt gttcca                                   26

<210> SEQ ID NO 159
<211> LENGTH: 32
<212> TYPE: DNA
<213> ORGANISM: Erythrovirus B19

<400> SEQUENCE: 159
catgtgttaa agtggattga taaaaaatgt gg                            32

<210> SEQ ID NO 160
<211> LENGTH: 34
<212> TYPE: DNA
<213> ORGANISM: Erythrovirus B19

<400> SEQUENCE: 160
ctacatcatt aaatggaaag ttttcattat tcca                          34

<210> SEQ ID NO 161
<211> LENGTH: 32
<212> TYPE: DNA
<213> ORGANISM: Erythrovirus B19

<400> SEQUENCE: 161
tggaataatg aaaattttcc atttaatgat gt                            32

<210> SEQ ID NO 162
<211> LENGTH: 20
<212> TYPE: DNA
<213> ORGANISM: Erythrovirus B19

<400> SEQUENCE: 162
ccttcatccc agaccaccaa                                          20
```

HUMAN ERYTHROVIRUS

CROSS REFERENCE TO RELATED APPLICATION

This application is a divisional of U.S. application Ser. No. 12/724,032 filed Mar. 15, 2010, now abandoned, which claims the benefit of U.S. Provisional Application No. 61/159,967 filed on Mar. 13, 2009; each of which is herein incorporated by reference in its entirety.

FIELD OF THE INVENTION

The present invention relates to human erythrovirus and includes methods and compositions useful for detection of a novel variant.

BACKGROUND OF THE INVENTION

Members of the Parvoviridae family of viruses are common animal and insect pathogens, which are further classified into the subfamily Parvoviridae based at least on the ability to infect vertebrate cells. Parvovirinae belonging to the genus *Erythrovirus* are known to infect humans and include, for example, the prototypical parvovirus B19 referred to as Au (genotype 1) as well as variants such as A6 (genotype 2), and V9 and D91.1 (genotype 3). They are non-enveloped viruses that comprise a single-stranded, linear DNA genome. For example, the prototypical human erythrovirus known as parvovirus B19-Au (See e.g., GenBank Accession Number: M13178) has a linear DNA genome of approximately 5.6 kilobases in length.

Discovered in 1975, parvovirus B19 was subsequently linked to an aplastic crisis in a patient with sickle-cell disease. The virus has since been shown to cause or be associated with a variety of conditions and diseases including erythma infectiosum (EI) (fifth disease of childhood), spontaneous abortion, and certain forms of acute arthritis.

*Erythrovirus* are ubiquitous and contagious. In the case of parvovirus B19, an estimated 60% of adults are seropositive. Children are particularly susceptible at the age when they begin to play together regularly and attend school, the peak season for infection being in the spring and early summer.

In addition to transmission through airborne infections and close contact, human erythrovirus can also be transmitted vertically from a pregnant woman to her fetus. For example, among pregnant women with active cases, about 30% of the fetuses will become infected with parvovirus B19. And, it is now well documented that parvovirus B19 can cause spontaneous abortion when infection occurs within the first six weeks after conception. Infection at this early stage causes massive abnormalities that are inconsistent with life.

Transmission of human erythrovirus also can occur via blood or plasma products of various kinds. For example, cases of symptomatic illness have been reported to be due to blood products prepared from parvovirus B19-containing plasma pools. Parvovirus B19 DNA has been detected in single donations, in plasma pools, and in plasma derivatives (e.g., clotting factors, albumin, antithrombin III, and immunoglobulins) produced by different processes. Parvovirus B19 transmission has also been found in patients treated with clotting factors, as shown by a higher seroprevalence in treated hemophiliacs, by the presence of parvovirus B19 DNA, and by active seroconversion. Unfortunately, the risk of human erythrovirus transmission by blood/plasma products is enhanced by the virus's resistance to effective inactivation methods such as heat and solvent-detergent treatments.

Therefore, health risks from exposure to human erythrovirus continue to exist, and identification and characterization of variants of the *Erythrovirus* genus will constitute an important step towards proper diagnosis and management of infection Immunodiagnostic methods have been used to test blood, serum, or plasma that is potentially contaminated with human erythrovirus. But such immunodiagnostic methods have limitations including, for example, inability to effectively detect recent or current infections and/or inability to distinguish between the different erythrovirus genotypes. There is still a need, therefore, for identifying and characterizing human erythrovirus variants and developing sensitive and effective assays for detecting them and/or distinguishing from among them.

SUMMARY OF THE INVENTION

There is now provided an isolated nucleic acid molecule comprising a nucleotide sequence as set forth in SEQ ID NO: 1, SEQ ID NO:128, SEQ ID NO:129, or a complement thereof.

In one aspect, the present invention provides nucleic acid molecules that are individually useful for detection of Parvoviridae represented by the nucleic acid sequence of SEQ ID NO:1 (i.e., partial genomic sequence of the novel variant named D11 disclosed herein), as well as those of known parvovirus B19 Au genotype 1, A6 genotype 2, V9 genotype 3, and D91.1 genotype 3. Accordingly, the invention includes an isolated nucleic acid molecule comprising a sequence consisting of at least 12, at least 15, or at least 20 contiguous nucleotides or a complement thereof, wherein the contiguous nucleotides are contained in a nucleotide sequence selected from the group consisting of:

```
                                        (SEQ ID NO: 2)
5'-GATAACTGGTGGTGCTCT-3';

(SEQ ID NO: 3)
5'-ACTTCTGACTGGGA-3';

(SEQ ID NO: 4)
5'-GAATGTAACAAATTTGA-3';

(SEQ ID NO: 5)
5'-TTATTTAATAATGT-3';

(SEQ ID NO: 6)
5'-CTTGTAACTGAAA-3';

(SEQ ID NO: 7)
5'-TTTAGAGATGGAGA-3';

(SEQ ID NO: 8)
5'-TTAATGAAAAAAAT-3';

(SEQ ID NO: 9)
5'-CCTTTAAATGTTGT-3';

(SEQ ID NO: 10)
5'-CAGACTTTGAGCAGG-3';

(SEQ ID NO: 11)
5'-TGGAATAATGAAAA-3';

(SEQ ID NO: 12)
5'-TTTCCATTTAATGATGTAGC-3';

(SEQ ID NO: 13)
5'-TTGGTGGTCTGGGATGA-3';
```

(SEQ ID NO: 14)
5'-GAAGCTGCAAAAGCCATTTTAGG-3';

(SEQ ID NO: 15)
5'-ACCAGGGTAGATCA-3';

(SEQ ID NO: 16)
5'-ATAACCAGCAATGGTGACATTAC-3';

(SEQ ID NO: 17)
5'-CATGCTAAAGCCTTAAA-3';

(SEQ ID NO: 18)
5'-AGCCCTGACATGGG-3';

(SEQ ID NO: 19)
5'-TGGTGTAATGCACAAAGCTGG-3';

(SEQ ID NO: 20)
5'-CCACTATGAAAACTGGGCAATAAACTACAC-3';

(SEQ ID NO: 21)
5'-TTTGATTTCCCTGGAAT-3';

(SEQ ID NO: 22)
5'-AATGCAGATGCCCTCCACCCAGA-3';

(SEQ ID NO: 23)
5'-CTCCAAACCACCCC-3';

(SEQ ID NO: 24)
5'-TCAGCAGCAGTGGTGGTGAAAGCTCTGAAGAACTC-3';

(SEQ ID NO: 25)
5'-CCAGGCGCCTGGAACA-3';

(SEQ ID NO: 26)
5'-TGAAACCCCGCGCTCTAGTACGCC-3';

(SEQ ID NO: 27)
5'-TCCCCGGGACCAGTTCAGGAGAATCATTTGTCGGAAGC-3';

(SEQ ID NO: 28)
5'-CAGTTTCGTGAACTGTTAGT-3';

(SEQ ID NO: 29)
5'-GCTTGGTATAATGGATGGAA-3';

(SEQ ID NO: 30)
5'-AAATGTGCTTACCT-3';

(SEQ ID NO: 31)
5'-TTTGTAGATTATGAGTAAA-3';

(SEQ ID NO: 32)
5'-ATTTCTTTAGATAATCC-3';

(SEQ ID NO: 33)
5'-TATATAGTCATCATTTTCA-3';

(SEQ ID NO: 34)
5'-CATGGACAGTTATCTGACCACCCCCATGCCTTATCATCCAGTA-3';

(SEQ ID NO: 35)
5'-CAGAACCTAGAGGAGAAAATGCAGTATTATCTA-3';

(SEQ ID NO: 36)
5'-TGAAGACTTACACAAGCCTGGGCAAGTTAGC-3';

(SEQ ID NO: 37)
5'-TACCCGGTACTAACTATGTTGGGCCTGGCAATGAG-3';

(SEQ ID NO: 38)
5'-TACAAGCTGGGCC-3';

(SEQ ID NO: 39)
5'-GACAGTGCTGCAAGGATTCATGACTTTAGGTATAGCCAA-3';

(SEQ ID NO: 40)
5'-TTAAAAAATATAAAAAATGAAAC-3';

(SEQ ID NO: 41)
5'-TACTTTACTTTAAAAGGTGCAGCTGCCCCTGTGGCCCATTTTCAAGGAAGTTT-3';

(SEQ ID NO: 42)
5'-TACAACGCCTCAGAAAAATACCC-3';

(SEQ ID NO: 43)
5'-AGCATGACTTCAGTTAA-3';

(SEQ ID NO: 44)
5'-TCTGCAGAAGCCAGCACTGGTGCAGG-3';

(SEQ ID NO: 45)
5'-AAAAGCATGTGGAGTGA-3';

(SEQ ID NO: 46)
5'-AGTAGCTGCCACAATGC-3';

(SEQ ID NO: 47)
5'-TTAGATTTTAATGCTTT-3';

(SEQ ID NO: 48)
5'-GATGCTTTAACTGT-3';

(SEQ ID NO: 49)
5'-TATGCTTACTTAACAGTAGG-3';

(SEQ ID NO: 50)
5'-AGTGAAGAATCAGC-3';

(SEQ ID NO: 51)
5'-TTTTATGAAATGTACAA-3';

(SEQ ID NO: 52)
5'-GCTGAAGACAAAGAGTATCA-3';

(SEQ ID NO: 53)
5'-AATGAAAAGAACA-3';

(SEQ ID NO: 54)
5'-TGGAACAGAAGAGC-3';

(SEQ ID NO: 55)
5'-CTTCACTATGAAAG-3';

(SEQ ID NO: 56)
5'-CCTCAAATATTTTTAAAAATA-3';

(SEQ ID NO: 57)
5'-CCTCAAATATTTTTAAAAATA-3';

(SEQ ID NO: 58)
5'-CATTTACCATATGTACT-3';

(SEQ ID NO: 59)
5'-TATGACCCCACAGCTACAGATGCAAA-3';
and (SEQ ID NO: 60)
5'-GGATATGAAAAGCCTGAAGAATTGTGGAC-3'.

In another aspect, the present invention provides nucleic acid molecules that are individually useful for specific detection of the Parvoviridae represented by the nucleic acid sequence of SEQ ID NO: 1. Accordingly, the invention includes an isolated nucleic acid molecule comprising at least 12, at least 15, or at least 20 contiguous nucleotides of a nucleotide sequence or a complement thereof. The nucleotide sequence is selected from the group consisting of (SEQ ID NO: 61)
5'-CACTTCTGACTGGGAACCATTAACTCATTCTAACAGACT-3', (SEQ ID NO: 62)
5'-ATGTAAAGCTTAAATTTTTACCAGGAATGACTACAAAAG-3', -continued (SEQ ID NO: 63)
5'-AATATTTTAGAGATGGAGAACAATTTATAGAAAATTATT-3', (SEQ ID NO: 64)
5'-ATTTTAGAGATGGAGAACAATTTATAGAAAATTATTTAA-3', (SEQ ID NO: 65)
5'-TAACCAATATTGATGGGTACATAGATACCTGCATTTCTG-3', (SEQ ID NO: 66)
5'-ATGGGTACATAGATACCTGCATTTCTGCTTCTTTTAGAC-3', (SEQ ID NO: 67)
5'-TTAGACGGGGAGCCTTTCAGGCTAAAAAACCCCGCATTA-3', (SEQ ID NO: 68)
5'-GAACCAGGGGAATCTAGCGCTACAGGGGGAGATGTTGTG-3', (SEQ ID NO: 69)
5'-TGCCATTTGCTGGGAAGGGGACTAAAGCTGGAATAAAAT-3', (SEQ ID NO: 70)
5'-GGACTAAAGCTGGAATAAAATTTCAAACTATGGTAAATT-3', (SEQ ID NO: 71)
5'-TAAATTGGTTGTGTGAAAATAGGGTTTTTACAGAGGATA-3', (SEQ ID NO: 72)
5'-ATTGGTTGTGTGAAAATAGGGTTTTTACAGAGGATAAGT-3', (SEQ ID NO: 73)
5'-TTAACCAGTACACTTTACTTAGCAGTAGTCACAGTGGGA-3', (SEQ ID NO: 74)
5'-TAAAACTAGCTATTTATAAGGCTACCAATTTAGTGCCTA-3', (SEQ ID NO: 75)
5'-TAGCTATTTATAAGGCTACCAATTTAGTGCCTACAAGTA-3', (SEQ ID NO: 76)
5'-CTACCAATTTAGTGCCTACAAGTACATTTTTGTTACACA-3', (SEQ ID NO: 77)
5'-CAAGTACATTTTTGTTACACACAGACTTTGAGCAGGCTA-3', (SEQ ID NO: 78)
5'-CACACAGACTTTGAGCAGGCTAACTGTATTAAAGAAAAT-3', (SEQ ID NO: 79)
5'-GTGTCAAAATTATGACCCCTTGTTGGTGGGACAGCATGT-3', (SEQ ID NO: 80)
5'-GGATTGATAAAAAATGTGGCAAAAAAAATACACTGTGGT-3', (SEQ ID NO: 81)
5'-ATACACTGTGGTTTTATGGCCCACCAAGTACAGGAAAAA-3', (SEQ ID NO: 82)
5'-GTACAGGAAAAACAAATTTAGCAATGGCTATTGCTAAAA-3', (SEQ ID NO: 83)
5'-GCTTGGTGGTCTGGGATGAGGGTATTATTAAGTCTACTA-3', (SEQ ID NO: 84)
5'-GCTTACTTACAGAGGCTGACGTGCAGCAATGGCTTACAT-3', (SEQ ID NO: 85)
5'-CCCCGCGCTCTAGTACGCCAGTCCCCGGGACCAGTTCAG-3', (SEQ ID NO: 86)
5'-AGAATCATTTGTCGGAAGCTCAATTTCCTCCGAAGCTGT-3', (SEQ ID NO: 87)
5'-ATCATTTGTCGGAAGCTCAATTTCCTCCGAAGCTGTAGC-3', (SEQ ID NO: 88)
5'-AGCTCAATTTCCTCCGAAGCTGTAGCTGCATCGTGGGAA-3', (SEQ ID NO: 89)
5'-TGACTATGTATGGGATGGTATAAGGGGTTTACCTGTTTG-3', (SEQ ID NO: 90)
5'-TTAATAACAGTGGGGGAGGCTTGGGATTTTGTCCCCATT-3', (SEQ ID NO: 91)
5'-CAGTGGGGGAGGCTTGGGATTTTGTCCCCATTGCATTAA-3', (SEQ ID NO: 92)
5'-GCAAAAAATGTGCTTACCTATCTGGCTTGCAAAGTTTTG-3', (SEQ ID NO: 93)
5'-AATGTGCTTACCTATCTGGCTTGCAAAGTTTTGTAGATT-3', (SEQ ID NO: 94)
5'-TTTGTAGATTATGAGTAAAGAAATTGGTAAATGGTGGGA-3', (SEQ ID NO: 95)
5'-TTATGAGTAAAGAAATTGGTAAATGGTGGGAAAGTGATG-3', (SEQ ID NO: 96)
5'-CTTCTTTGTTTGACTTAGTGGCTCGTATTAAAAGTAACC-3', (SEQ ID NO: 97)
5'-ATGAAACTGGGTTTCAAGCTCAAGTAGTAAAAGACTACT-3', (SEQ ID NO: 98)
5'-TCCTGATGCTTTAACTGTTGCCATATCAGAAATTGCCAT-3', (SEQ ID NO: 99)
5'-TTGCCATATCAGAAATTGCCATTAAAGATGTTACAGACA-3', (SEQ ID NO: 100)
5'-TGCCATATCAGAAATTGCCATTAAAGATGTTACAGACAA-3', (SEQ ID NO: 101)
5'-AATACAAGTACCCATATGTATTAGGTCAAGGACAAGATA-3', (SEQ ID NO: 102)
5'-AAGATACCTTAGCCCCAGAGCTTCCAATTTGGGTGTACT-3', (SEQ ID NO: 103)
5'-CAGTAGGAGATGTAAACACGCAGGGAATTTCTGGGGACA-3', (SEQ ID NO: 104)
5'-AGAATCAGCGTTTTATGTCCTGGAACACAGCTCTTTTGA-3', (SEQ ID NO: 105)
5'-CTACTATGTCTTATAAGTTCCCTCCAGTGCCCCCAGAGA-3', (SEQ ID NO: 106)
5'-TCCCTCCAGTGCCCCCAGAGAATTTAGAAGGCTGTAGTC-3', (SEQ ID NO: 107)
5'-CCCGTTTAGGAGTCCCTGATACATTAGGAGGGGACCCCA-3', (SEQ ID NO: 108)
5'-AACACATGAAGACCACGCAGTTCAGCCACAAAATTTTAT-3', (SEQ ID NO: 109)
5'-ACGCAGTTCAGCCACAAAATTTTATGCCAGGGCCACTGG-3', (SEQ ID NO: 110)
5'-GGCCACTGGTAAACTCAGTTTCCACAAAGGAGGGAGACA-3', (SEQ ID NO: 111)
5'-AGGAGGGAGACAGTTCTAACACAGGAGCGGGAAAAGCCC-3', (SEQ ID NO: 112)
5'-GTCAAAGTACTAGAATATCATTACGCCCTGGTCCAGTGT-3', (SEQ ID NO: 113)
5'-GCCCTGGTCCAGTGTCTCAACCATATCACCACTGGGACA-3', (SEQ ID NO: 114)
5'-GTCCAGTGTCTCAACCATATCACCACTGGGACACAGATA-3', (SEQ ID NO: 115)
5'-CAGATAAATATGTAACAGGGATAAATGCCATTTCTCATG-3', (SEQ ID NO: 116)
5'-CTGAAGACAAAGAGTATCAACAGGGCGTGGGTAGGTTTC-3', -continued (SEQ ID NO: 117)
5'-AAGACAAAGAGTATCAACAGGGCGTGGGTAGGTTTCCCA-3', (SEQ ID NO: 118)
5'-AGGGCGTGGGTAGGTTTCCCAATGAAAAAGAACAACTAA-3'

(SEQ ID NO: 119)
5'-AACAGTTACAGGGTTTAAATATACACACATATTTTCCCA-3', (SEQ ID NO: 120)
5'-GTTTAAATATACACACATATTTTCCCAATAAAGGTACCC-3', (SEQ ID NO: 121)
5'-TACCAAATTTAGATGACAGCTTTAAAACTCAGTTTGCAG-3', (SEQ ID NO: 122)
5'-AGCTTTAGGAGGTTGGGGACTACATCAGCCACCCCCTCA-3', (SEQ ID NO: 123)
5'-GGCCAATTGGGGGTATTAAGTCAATGGGAATAACAACAT-3', (SEQ ID NO: 124)
5'-TTAAGTCAATGGGAATAACAACATTAGTTCAATATGCTG-3', (SEQ ID NO: 125)
5'-TAGTTCAATATGCTGTGGGTATTATGACAGTAACTATGA-3', (SEQ ID NO: 126)
5'-TAACTATGACATTTAAATTAGGGCCTCGCAAAGCTACAG-3',
and (SEQ ID NO: 127)
5'-ACCCTCCTCACGCAGCAGGCCATTTACCATATGTACTAT-3'.

In other aspects, the present invention provides an isolated nucleic acid molecule consisting of a nucleotide sequence or a complement thereof, wherein the nucleotide sequence is selected from the group consisting of:

(SEQ ID NO: 136)
5'-TGAAACCCCGCGCTCTA-3';

(SEQ ID NO: 137)
5'-AACTAACAGTTCACGAAACTG-3';

(SEQ ID NO: 138)
5'-TCCCCGGGACCAGTTCAGGAGAA-3';

(SEQ ID NO: 139)
5'-TCAGCAGCAGTGGTGGT-3';

(SEQ ID NO: 140)
5'-TAGAGCGCGGGGTTTCA-3';

(SEQ ID NO: 141)
5'-TGAAAGCTCTGAAGAACTCAGTGAAAGCAGCTTT-3';

(SEQ ID NO: 142)
5'-AATGCAGATGCCCTCCAC-3';

(SEQ ID NO: 143)
5'-TCAGCAGCAGTGGTGGTGAAAGCTCTGAA-3';

(SEQ ID NO: 144)
5'-TGTTCCAGGCGCCTG-3';

(SEQ ID NO: 145)
5'-CACAGCTACAGATGCAAA-3';

(SEQ ID NO: 146)
5'-GGTGCACACGGCTTTT-3';

(SEQ ID NO: 147)
5'-TGTCCACAATTCTTCAGGCTTTTCATATCC-3';

(SEQ ID NO: 148)
5'-TGGATATGAAAAGCCTGAAGTATTGTGGAC-3';

(SEQ ID NO: 149)
5'-GGTCATTTACCATATGTACT-3';

(SEQ ID NO: 150)
5'-AGCTACAGATGCAAANCAACACCACAGACA-3';

(SEQ ID NO: 151)
5'-GAAAACTTTCCATTTAATGATGT-3';

(SEQ ID NO: 152)
5'-ATTTTTTGATCTACCCTGGT-3';

(SEQ ID NO: 153)
5'-TTGGTGGTCTGGGATGAAGG-3';

(SEQ ID NO: 154)
5'-GTTTTATGGGCCGCCAAGTA-3';

(SEQ ID NO: 155)
5'-TTCATCCCAGACCACCAAGG-3';

(SEQ ID NO: 156)
5'-ATGGCTATTGCTAAAACTGTTCCAGTGTA-3';

(SEQ ID NO: 157)
5'-TGGAATAATGAAAACTTTCCATTTAATGATGTAG-3';
and (SEQ ID NO: 158)
5'-CAATGGCCATTGCTAAAAGTGTTCCA-3'.

In another aspect, the present invention provides an isolated polynucleotide comprising a nucleotide sequence or a complement thereof. The nucleotide sequence is selected from the group consisting of:

(SEQ ID NO: 159)
5'-CATGTGTTAAAGTGGATTGATAAAAAATGTGG-3';

(SEQ ID NO: 160)
5'-CTACATCATTAAATGGAAAGTTTTCATTATTCCA-3';
and (SEQ ID NO: 161)
5'-TGGAATAATGAAAATTTTCCATTTAATGATGT-3';
and (SEQ ID NO: 162)
5'-CCTTCATCCCAGACCACCAA-3'.

In some aspects, the present invention provides an isolated nucleic acid molecule that anneals under a stringent condition to a polynucleotide comprising a nucleotide sequence as set forth in SEQ ID NO: 1, SEQ ID NO:128, SEQ ID NO:129, or a complement thereof, but does not anneal under the stringent condition to a non-parvovirus DNA or RNA molecule that may be present in a test sample (i.e., binds specifically to parvovirus B19 nucleic acid).

In one aspect, the present invention provides an isolated nucleic acid molecule that anneals under a stringent condition to a nucleotide sequence as set forth in SEQ ID NO: 1, SEQ ID NO:128, SEQ ID NO:129, or a complement thereof, wherein the isolated nucleic acid molecule also anneals under the stringent condition to a DNA or a RNA of parvovirus B19 Au, A6, V9, or D91.1.

In another aspect, the present invention provides an isolated nucleic acid molecule that anneals under a stringent condition to a nucleotide sequence or a complement thereof, wherein the nucleotide sequence is as set forth in SEQ ID NO: 1, SEQ ID NO:128, SEQ ID NO:129, SEQ ID NO:130, SEQ ID NO:131, SEQ ID NO:132, and SEQ ID NO:133.

In other aspects, the present invention provides an isolated nucleic acid molecule that anneals under a stringent condition to a nucleotide sequence as set forth in SEQ ID NO: 1, SEQ ID NO:128, SEQ ID NO:129, or a complement thereof, wherein the isolated nucleic acid molecule does not anneal under the stringent condition to a DNA or a RNA of parvovirus B19 Au, A6, V9, or D91.1.

In various other aspects, the present invention provides an isolated nucleic acid molecule comprising an open reading frame, a partial open reading frame, or a complement thereof, wherein the open reading frame is comprised in SEQ ID NO: 1, SEQ ID NO:128, SEQ ID NO:129, or a complement thereof.

In other aspects, the present invention provides an isolated human erythrovirus comprising a genome comprising a nucleotide sequence as set forth in SEQ ID NO: 1, SEQ ID NO:128, or SEQ ID NO:129.

In one aspect, the present invention provides a kit comprising at least one primer and at least one probe, wherein the at least one primer comprises a primer nucleic acid sequence as set forth in (SEQ ID NO: 136), (SEQ ID NO: 137), (SEQ ID NO: 139), (SEQ ID NO: 140), (SEQ ID NO: 142), (SEQ ID NO: 144), (SEQ ID NO: 145), (SEQ ID NO: 146), (SEQ ID NO: 149), (SEQ ID NO: 151), (SEQ ID NO: 152), (SEQ ID NO: 154), or (SEQ ID NO: 155), wherein the at least one probe comprises a probe nucleic acid sequence as set forth in (SEQ ID NO: 138), (SEQ ID NO: 141), (SEQ ID NO: 143), (SEQ ID NO: 147), (SEQ ID NO: 148), (SEQ ID NO: 150), (SEQ ID NO: 153), (SEQ ID NO: 156), (SEQ ID NO: 157), (SEQ ID NO: 158), or complements thereof.

In another aspect, the kit comprises a forward primer, a reverse primer, and a probe, wherein the forward primer comprises a forward primer nucleic acid sequence as set forth in (SEQ ID NO: 136), (SEQ ID NO: 139), (SEQ ID NO: 142), (SEQ ID NO: 145), (SEQ ID NO: 149), (SEQ ID NO: 151), or (SEQ ID NO: 154), wherein the reverse primer comprises a reverse primer nucleic acid sequence as set forth in (SEQ ID NO: 137), (SEQ ID NO: 140), (SEQ ID NO: 144), (SEQ ID NO: 146), (SEQ ID NO: 152), or (SEQ ID NO: 155), wherein the probe comprises a probe nucleic acid sequence as set forth in (SEQ ID NO: 136), (SEQ ID NO: 137), (SEQ ID NO: 138), (SEQ ID NO: 139), (SEQ ID NO: 140), (SEQ ID NO: 141), (SEQ ID NO: 142), (SEQ ID NO: 143), (SEQ ID NO: 144), (SEQ ID NO: 145), (SEQ ID NO: 146), (SEQ ID NO: 147), (SEQ ID NO: 148), (SEQ ID NO: 149), (SEQ ID NO: 150), (SEQ ID NO: 151), (SEQ ID NO: 152), (SEQ ID NO: 153), (SEQ ID NO: 154), (SEQ ID NO: 155), (SEQ ID NO: 156), (SEQ ID NO: 157), (SEQ ID NO: 158), or complements thereof.

In some aspects, the present invention provides a method for detecting a parvovirus B19 in a sample. The method comprises:

a) performing PCR with at least a portion of the sample using a forward primer having a forward primer nucleic acid sequence and a reverse primer having a reverse primer nucleic acid sequence, wherein the forward primer nucleic acid sequence is as set forth in (SEQ ID NO: 136), (SEQ ID NO: 139), (SEQ ID NO: 142), (SEQ ID NO: 145), (SEQ ID NO: 149), (SEQ ID NO: 151), or (SEQ ID NO: 154), wherein the reverse primer nucleic acid sequence is as set forth in (SEQ ID NO: 137), (SEQ ID NO: 140), (SEQ ID NO: 144), (SEQ ID NO: 146), (SEQ ID NO: 152), or (SEQ ID NO: 155); and b) determining the presence or absence of an amplicon, wherein the presence of the amplicon is indicative of the presence of the parvovirus B19 in the sample, wherein determining comprises annealing an oligonucleotide to the amplicon.

In further aspects, the present invention provides a method for determining parvovirus B19 in a sample. The method comprises a) amplifying parvovirus B19 nucleic acid in the sample using at least one nucleic acid molecule comprising i) a sequence consisting of at least 12, at least 15, or at least 20 contiguous nucleotides or a complement thereof, wherein the contiguous nucleotides are contained in a nucleotide sequence selected from the group consisting of: (SEQ ID NO: 2), (SEQ ID NO: 3), (SEQ ID NO: 4), (SEQ ID NO: 5), (SEQ ID NO: 6), (SEQ ID NO: 7), (SEQ ID NO: 8), (SEQ ID NO: 9), (SEQ ID NO: 10), (SEQ ID NO: 11), (SEQ ID NO: 12), (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), (SEQ ID NO: 39), (SEQ ID NO: 40), (SEQ ID NO: 41), (SEQ ID NO: 42), (SEQ ID NO: 43), (SEQ ID NO: 44), (SEQ ID NO: 45), (SEQ ID NO: 46), (SEQ ID NO: 47), (SEQ ID NO: 48), (SEQ ID NO: 49), (SEQ ID NO: 50), (SEQ ID NO: 51), (SEQ ID NO: 52), (SEQ ID NO: 53), (SEQ ID NO: 54), (SEQ ID NO: 55), (SEQ ID NO: 56), (SEQ ID NO: 57), (SEQ ID NO: 58), (SEQ ID NO: 59), and (SEQ ID NO: 60); or ii) at least 12, at least 15, or at least 20 contiguous nucleotides of a nucleotide sequence or a complement thereof, wherein the nucleotide sequence is selected from the group consisting of: (SEQ ID NO: 61), (SEQ ID NO: 62), (SEQ ID NO: 63), (SEQ ID NO: 64), (SEQ ID NO: 65), (SEQ ID NO: 66), (SEQ ID NO: 67), (SEQ ID NO: 68), (SEQ ID NO: 69), (SEQ ID NO: 70), (SEQ ID NO: 71), (SEQ ID NO: 72), (SEQ ID NO: 73), (SEQ ID NO: 74), (SEQ ID NO: 75), (SEQ ID NO: 76), (SEQ ID NO: 77), (SEQ ID NO: 78), (SEQ ID NO: 79), (SEQ ID NO: 80), (SEQ ID NO: 81), (SEQ ID NO: 82), (SEQ ID NO: 83), (SEQ ID NO: 84), (SEQ ID NO: 85), (SEQ ID NO: 86), (SEQ ID NO: 87), (SEQ ID NO: 88), (SEQ ID NO: 89), (SEQ ID NO: 90), (SEQ ID NO: 91), (SEQ ID NO: 92), (SEQ ID NO: 93), (SEQ ID NO: 94), (SEQ ID NO: 95), (SEQ ID NO: 96), (SEQ ID NO: 97), (SEQ ID NO: 98), (SEQ ID NO: 99), (SEQ ID NO: 100), (SEQ ID NO: 101), (SEQ ID NO: 102), (SEQ ID NO: 103), (SEQ ID NO: 104), (SEQ ID NO: 105), (SEQ ID NO: 106), (SEQ ID NO: 107), (SEQ ID NO: 108), (SEQ ID NO: 109), (SEQ ID NO: 110), (SEQ ID NO: 111), (SEQ ID NO: 112), (SEQ ID NO: 113), (SEQ ID NO: 114), (SEQ ID NO: 115), (SEQ ID NO: 116), (SEQ ID NO: 117), (SEQ ID NO: 118), (SEQ ID NO: 119), (SEQ ID NO: 120), (SEQ ID NO: 121), (SEQ ID NO: 122), (SEQ ID NO: 123), (SEQ ID NO: 124), (SEQ ID NO: 125), (SEQ ID NO: 126), and (SEQ ID NO: 127); and b) detecting an amplicon generated in step (a), wherein detection of the amplicon indicates presence of the variant in the sample, wherein detecting optionally comprises the step of annealing at least one nucleic acid molecule of step (a)(ii) to the amplicon.

In some aspects, the present invention provides for a method for determining parvovirus B19 in a sample. The method comprises a) amplifying parvovirus B19 nucleic acid in the sample using at least one nucleic acid molecule comprising a sequence consisting of at least 12, at least 15, or at least 20 contiguous nucleotides or a complement thereof, wherein the contiguous nucleotides are contained in a nucleotide sequence selected from the group consisting of: (SEQ ID NO: 2), (SEQ ID NO: 3), (SEQ ID NO: 4), (SEQ ID NO: 5), (SEQ ID NO: 6), (SEQ ID NO: 7), (SEQ ID NO: 8), (SEQ ID NO: 9), (SEQ ID NO: 10), (SEQ ID NO: 11), (SEQ ID NO: 12), (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), (SEQ ID NO: 39), (SEQ ID NO: 40), (SEQ ID NO: 41), (SEQ ID NO: 42), (SEQ ID NO: 43), (SEQ ID NO: 44), (SEQ ID NO: 45), (SEQ ID NO: 46), (SEQ ID NO: 47), (SEQ ID NO: 48), (SEQ ID NO: 49), (SEQ ID NO: 50), (SEQ ID NO: 51), (SEQ ID NO: 52), (SEQ ID NO: 53), (SEQ ID NO: 54), (SEQ ID NO: 55), (SEQ ID NO: 56), (SEQ ID NO: 57), (SEQ ID NO: 58), (SEQ ID NO: 59), and (SEQ ID NO: 60); and b) detecting an amplicon generated in step (a), wherein detection of the amplicon indicates presence of the parvovirus B19 in the sample, wherein detecting optionally comprises the step of annealing at least one nucleic acid molecule to the amplicon.

In other aspects, the present invention provides a method for determining parvovirus B19 in a sample. The method comprises:

a) amplifying parvovirus B19 nucleic acid in the sample with at least one pair of primers comprising a first primer and a second primer, wherein the first primer comprises a nucleotide sequence as set forth in (SEQ ID NO:154) or (SEQ ID NO:159); and b) detecting an amplicon generated in step (a), wherein detection of the amplicon indicates presence of the parvovirus B19 in the sample. In one embodiment, the detecting step (b) comprises contacting the amplicon with a polynucleotide probe comprising a nucleotide sequence as set forth in (SEQ ID NO:160) or (SEQ ID NO:161).

Advantages and benefits of the present invention will be apparent to one skilled in the art from reading this specification.

BRIEF DESCRIPTION OF THE FIGURES

FIG. 1 shows a partial genomic DNA sequence corresponding to a novel parvovirus B19 variant disclosed herein (i.e., SEQ ID NO: 1 for the D11 variant). Open reading frames (ORF) for VP1 and VP2 proteins begin at nucleotide position 2105 and 2786, respectively, whereas the partial ORF for NS1 protein is shown from nucleotide position 1 through 2109, where nucleotide position 2107-2109, namely GAG, encodes glutamic acid.

Figure 2A:
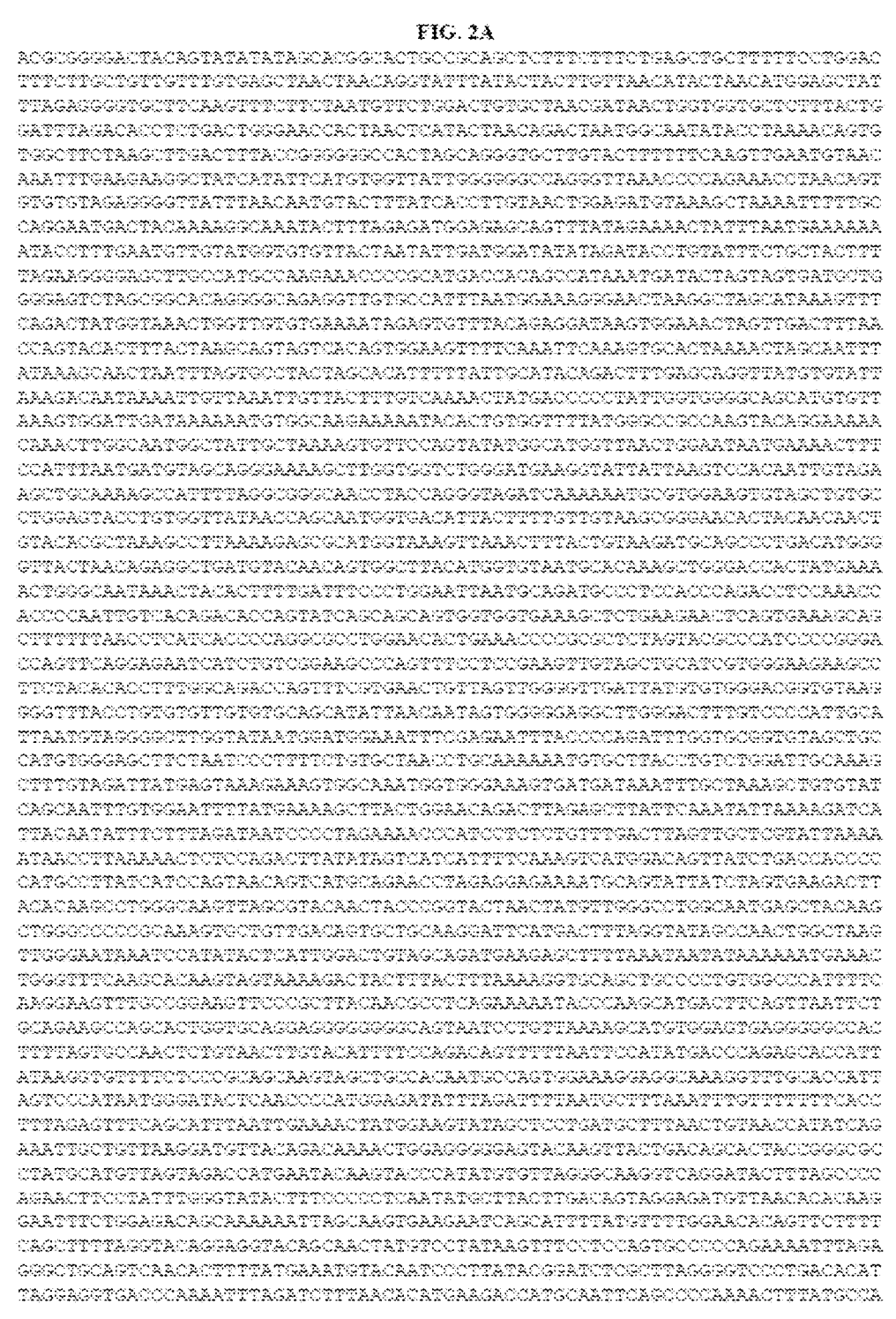

FIG. 2A-B shows a partial genomic DNA sequence corresponding to a novel parvovirus B19 variant disclosed and referred to herein as E3 (i.e., SEQ ID NO: 128). The open reading frame (ORF) for VP1 protein begins at nucleotide position 2141, whereas nucleotide position 1 through 2145 comprises the partial ORF for NS1 protein.

FIG. 3A-B shows a partial genomic DNA sequence corresponding to a novel parvovirus B19 variant disclosed and referred to herein as P1 (i.e., SEQ ID NO: 129). The open reading frame (ORF) for VP1 protein begins at nucleotide position 2263, whereas nucleotide position 1 through 2267 comprises the partial ORF for NS1 protein.

Figure 4A:
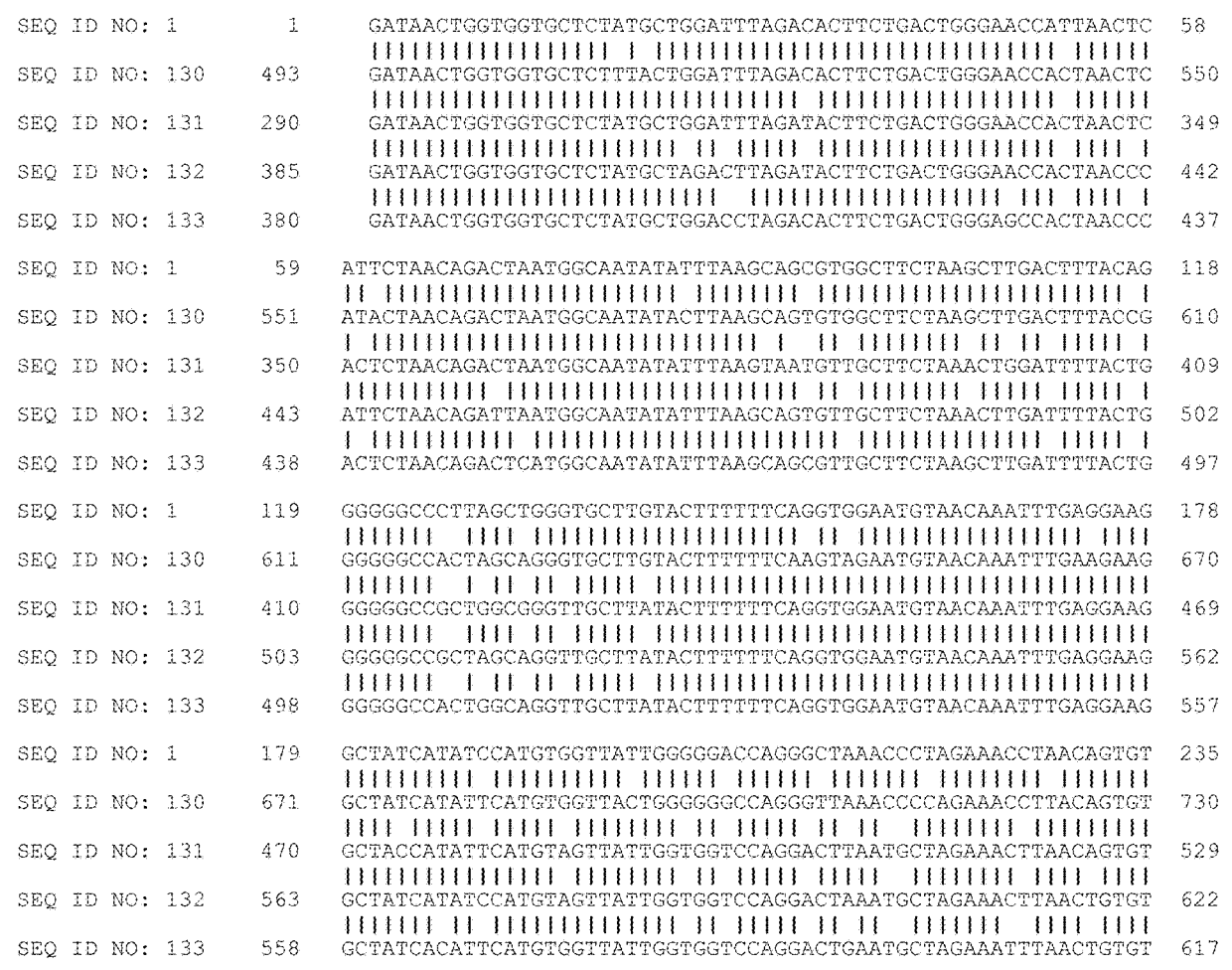
Figure 4C:
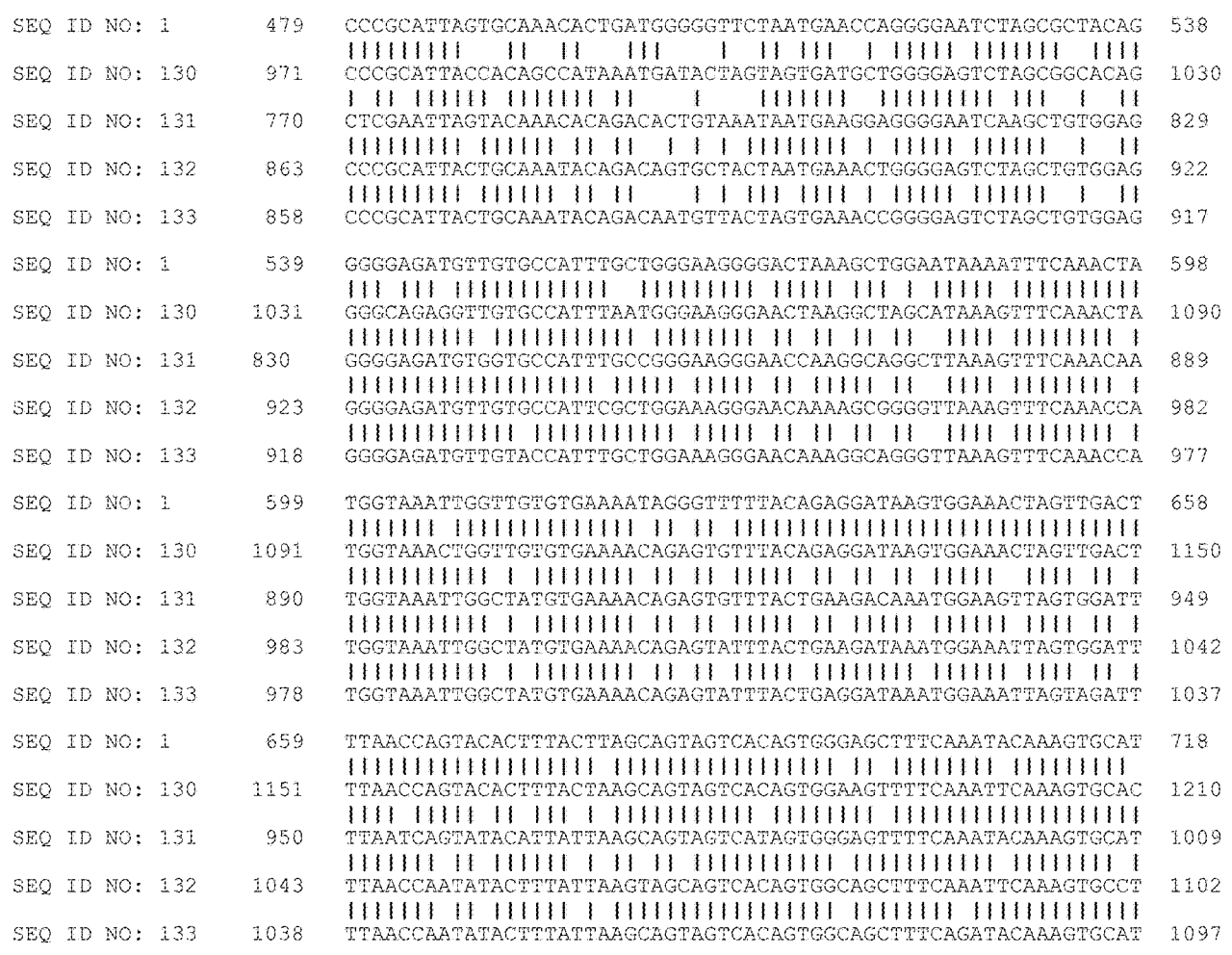
Figure 4D:
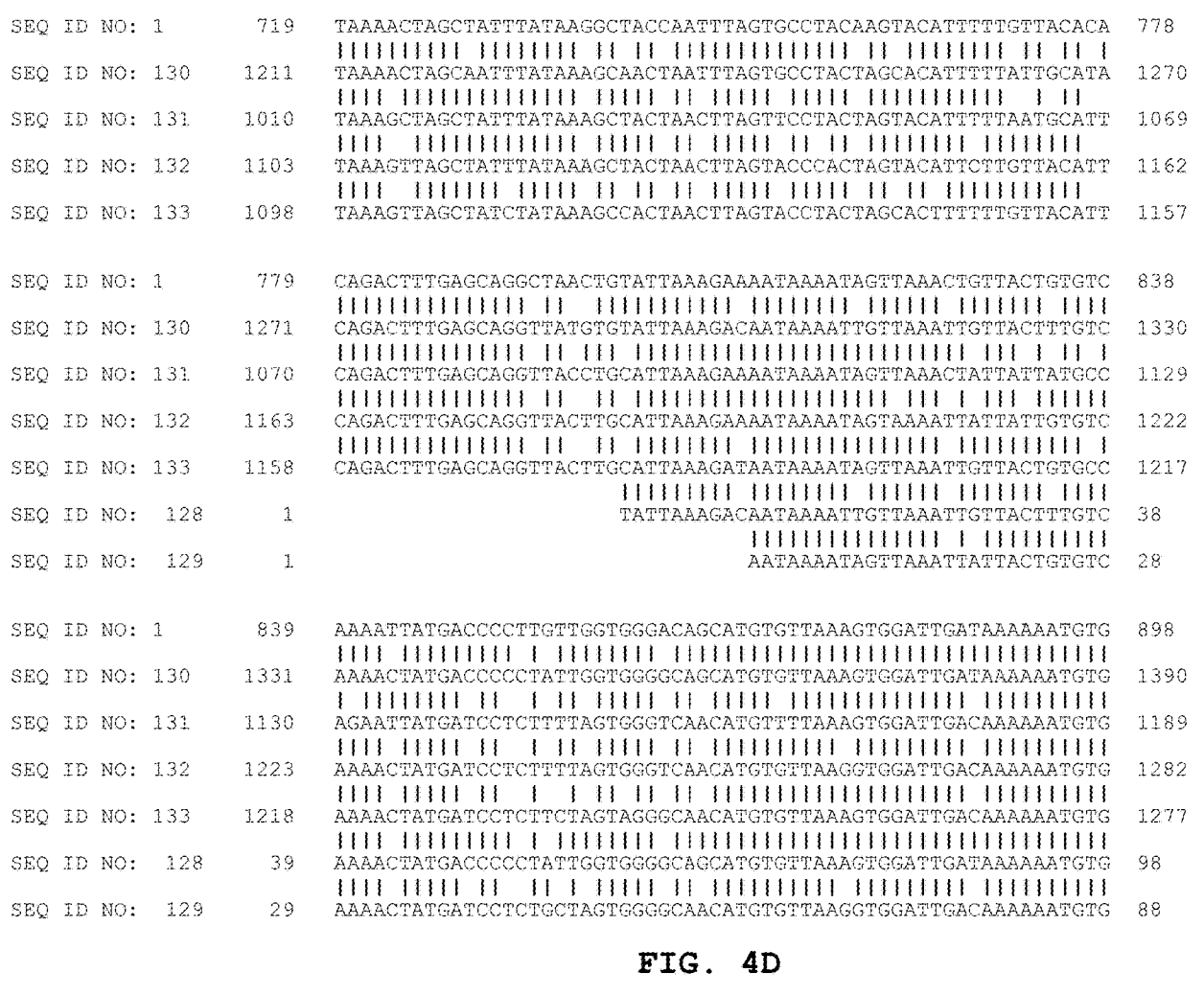
Figure 4F:
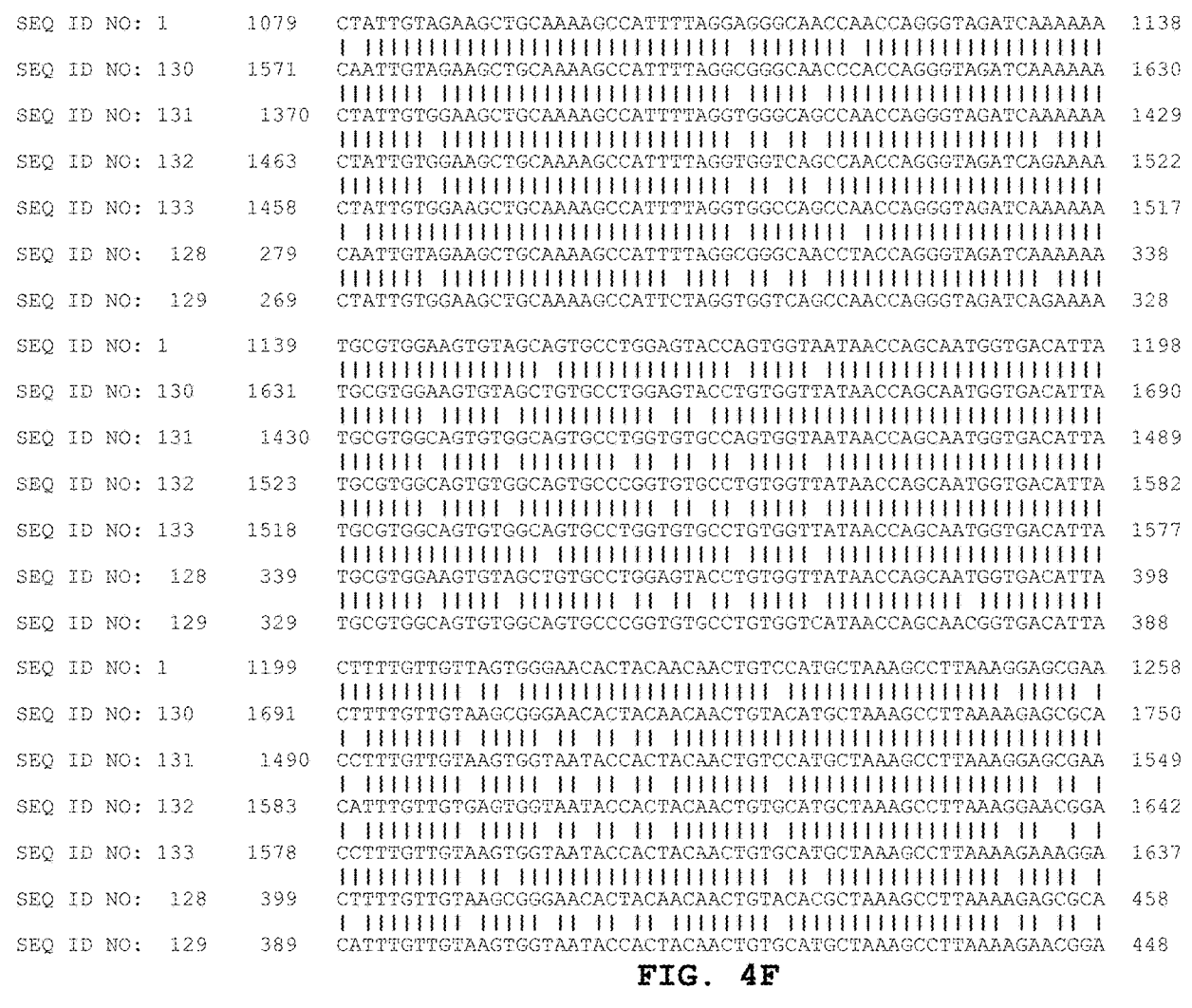
Figure 4G:
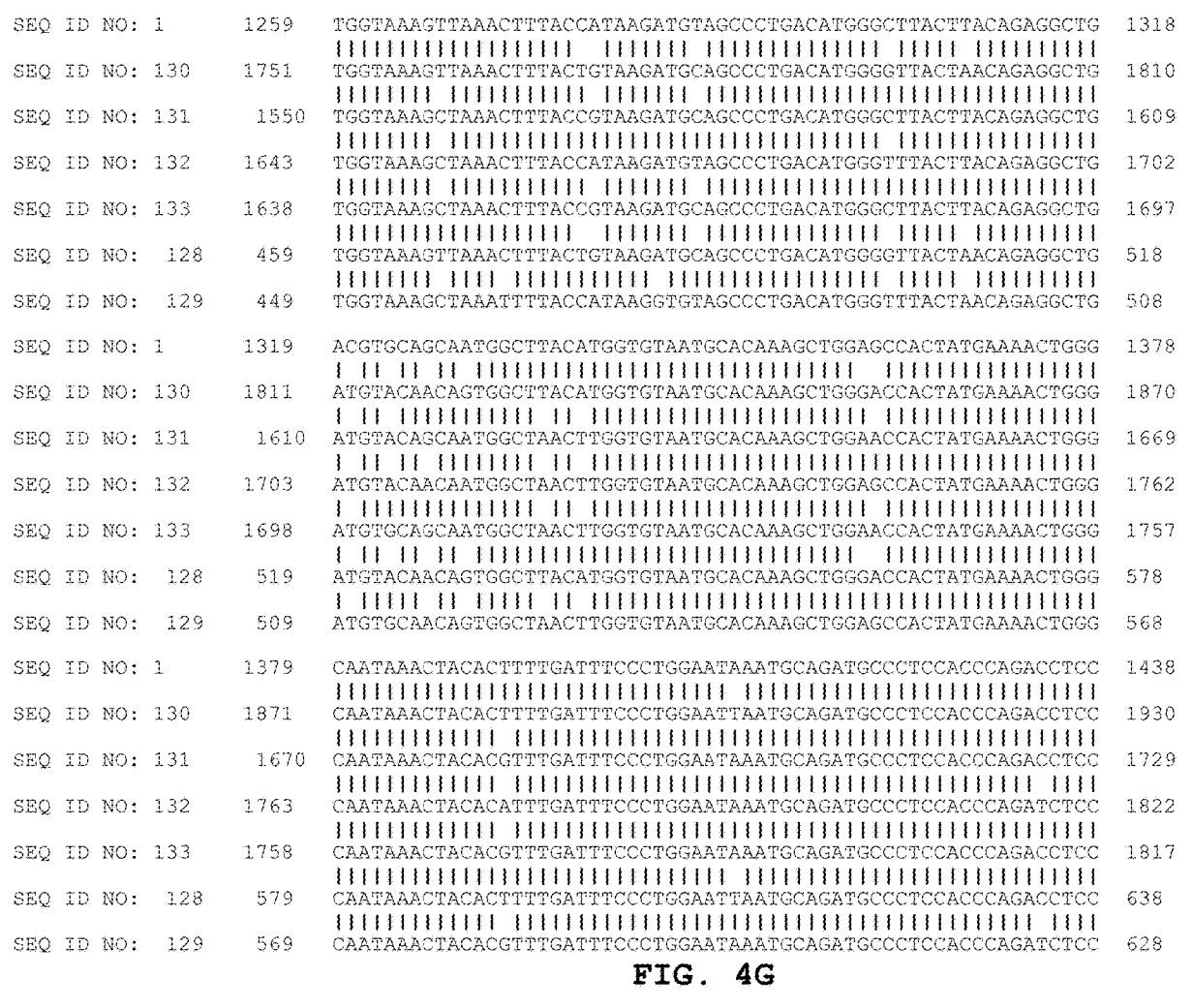
Figure 4I:
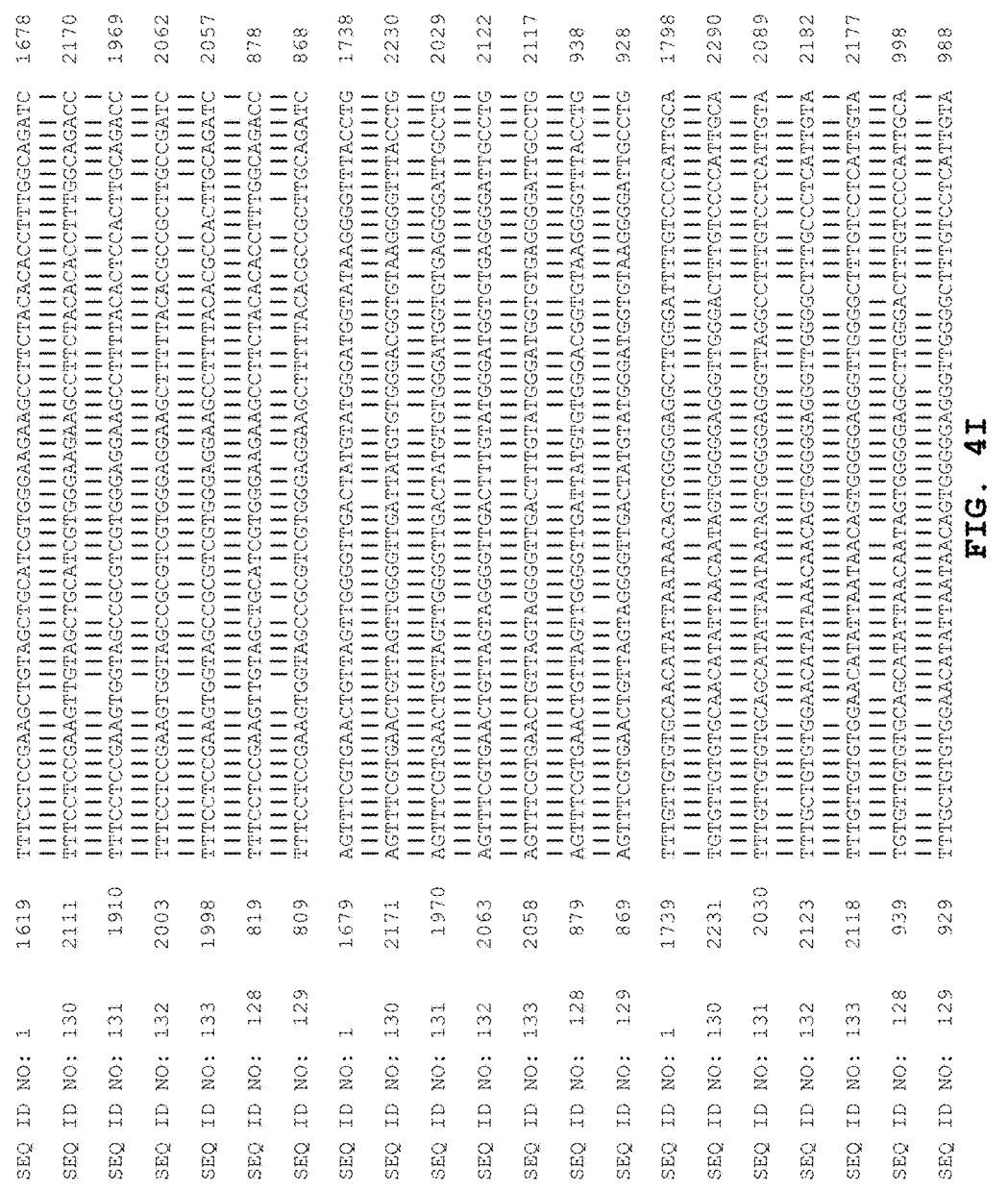
Figure 4J:
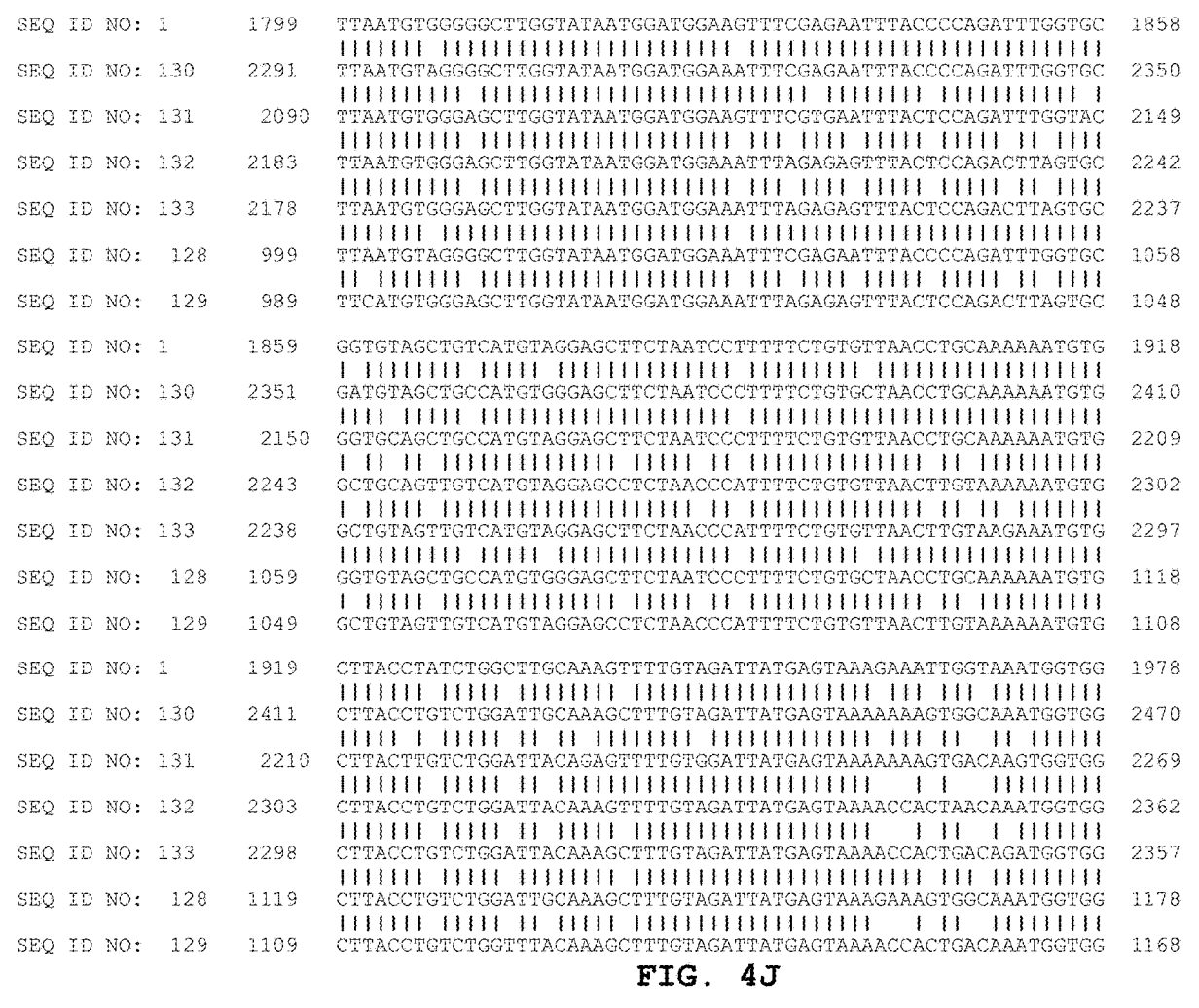
Figure 4K:
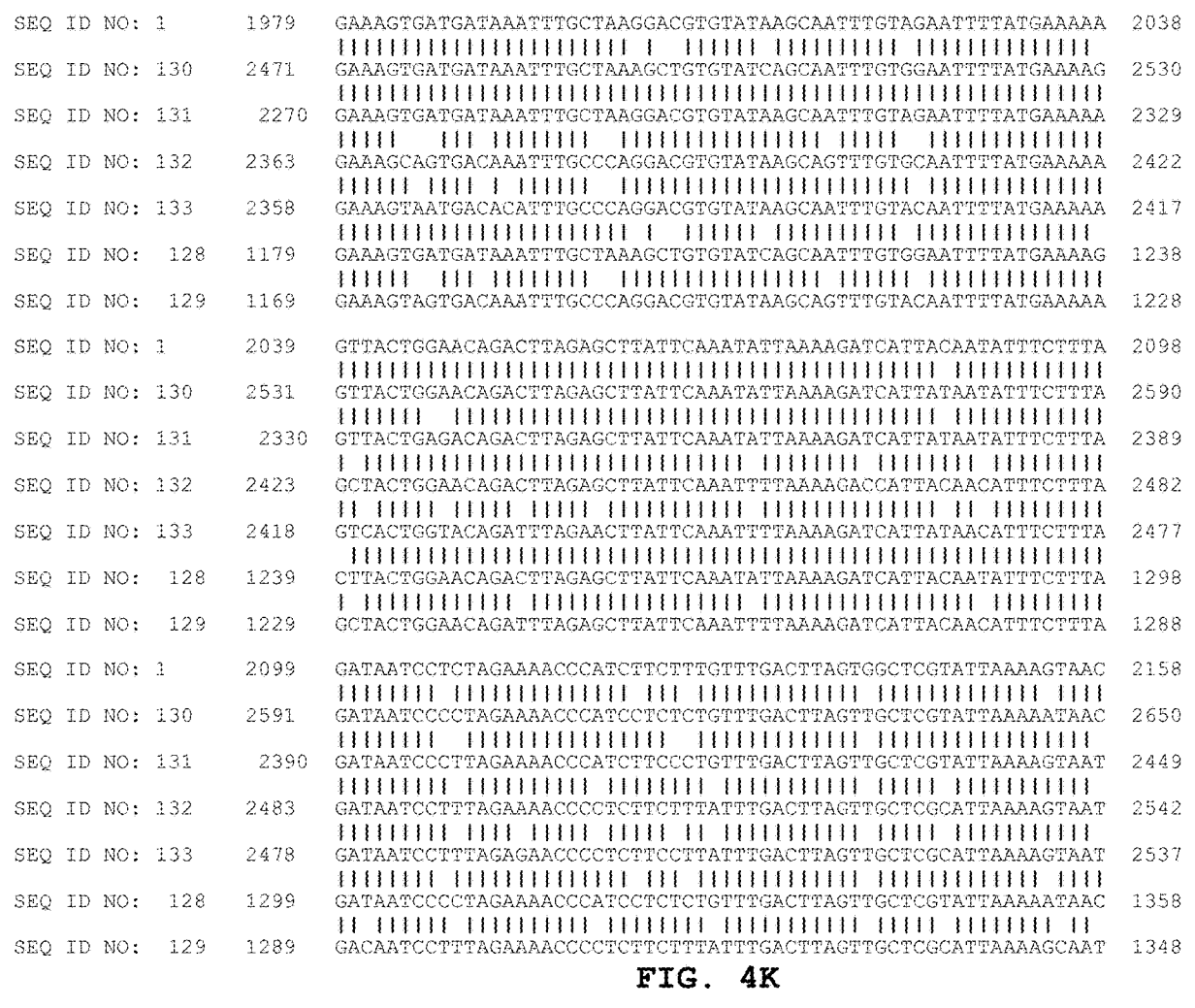
Figure 4L:
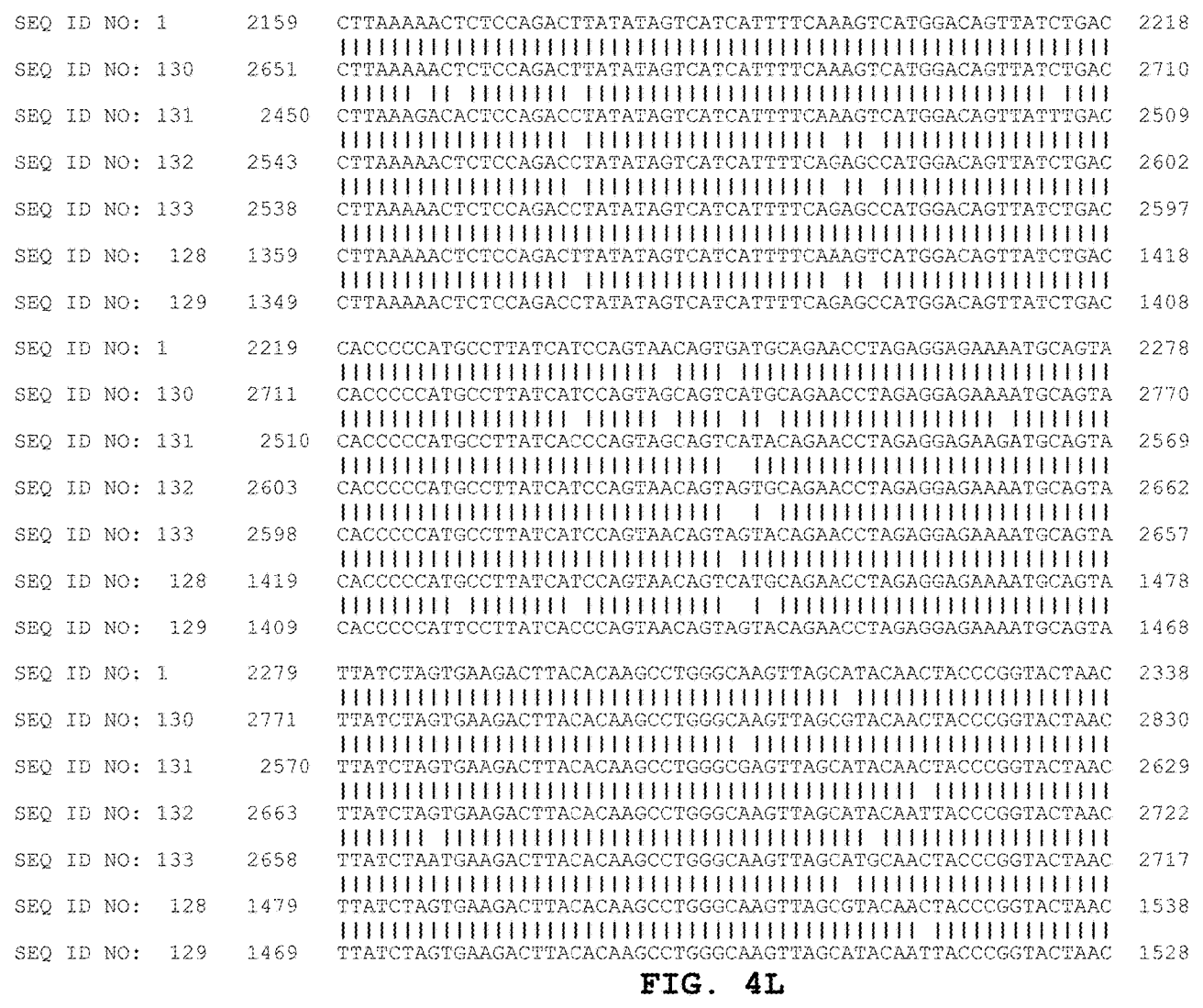
Figure 4M:
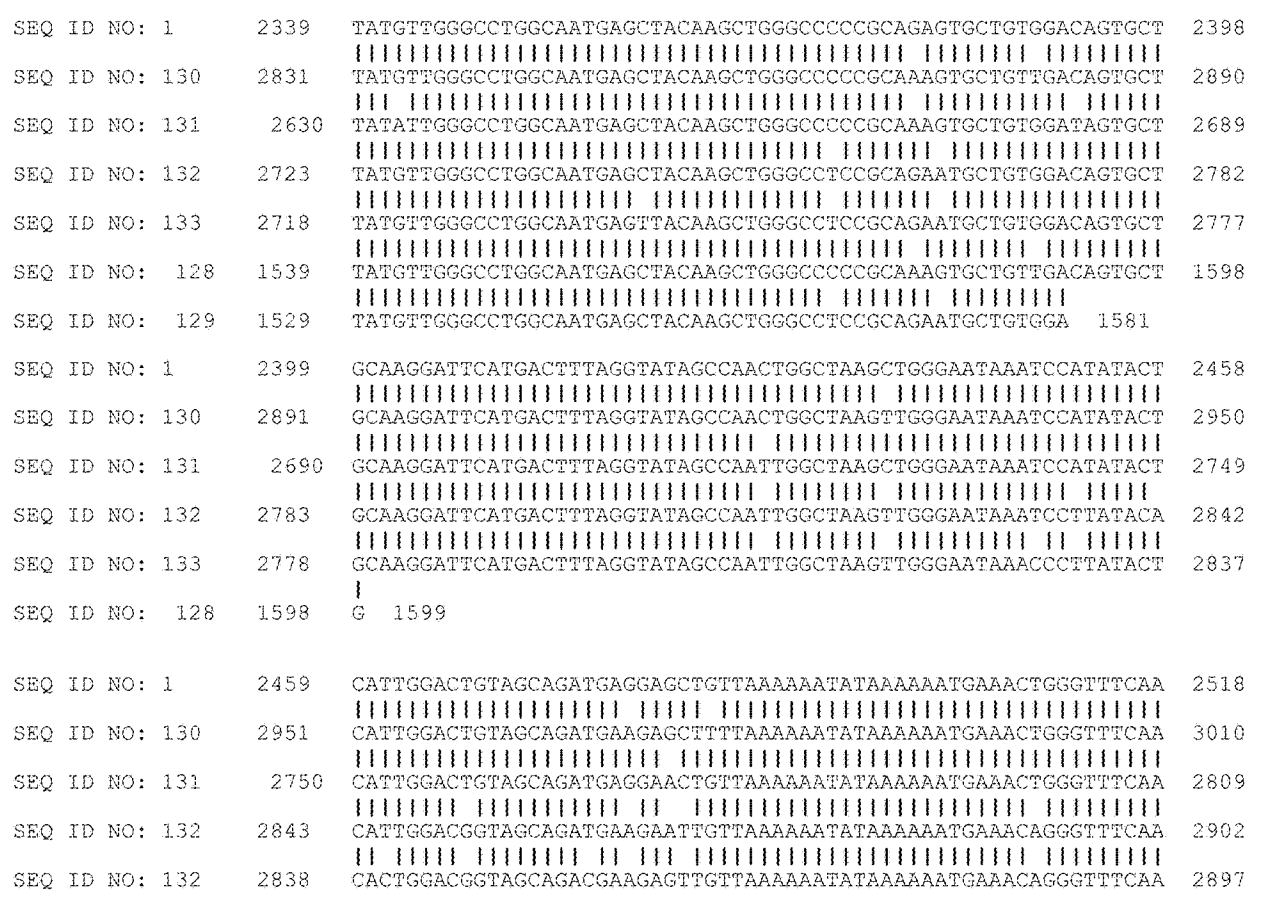
Figure 4P:
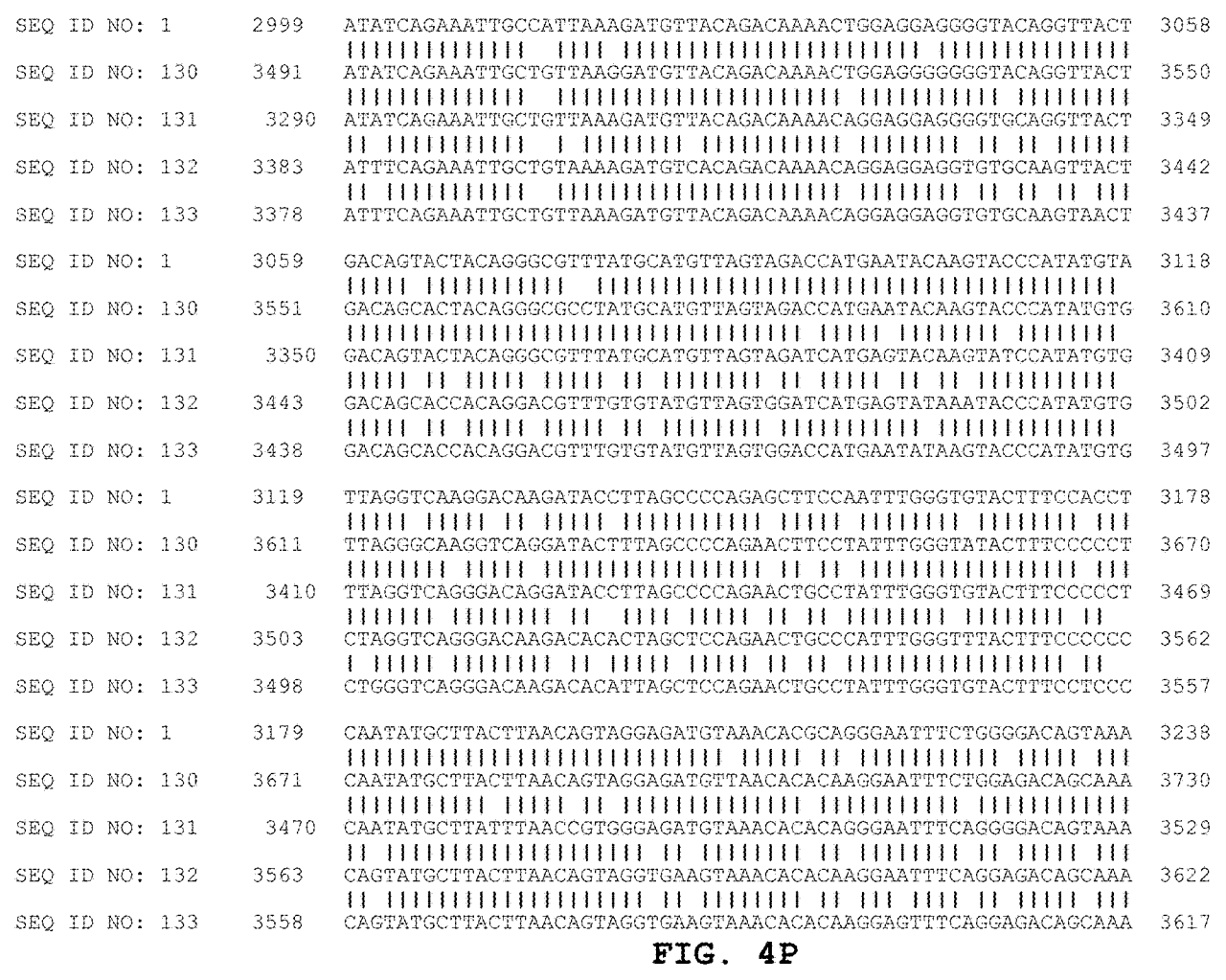
Figure 4T:
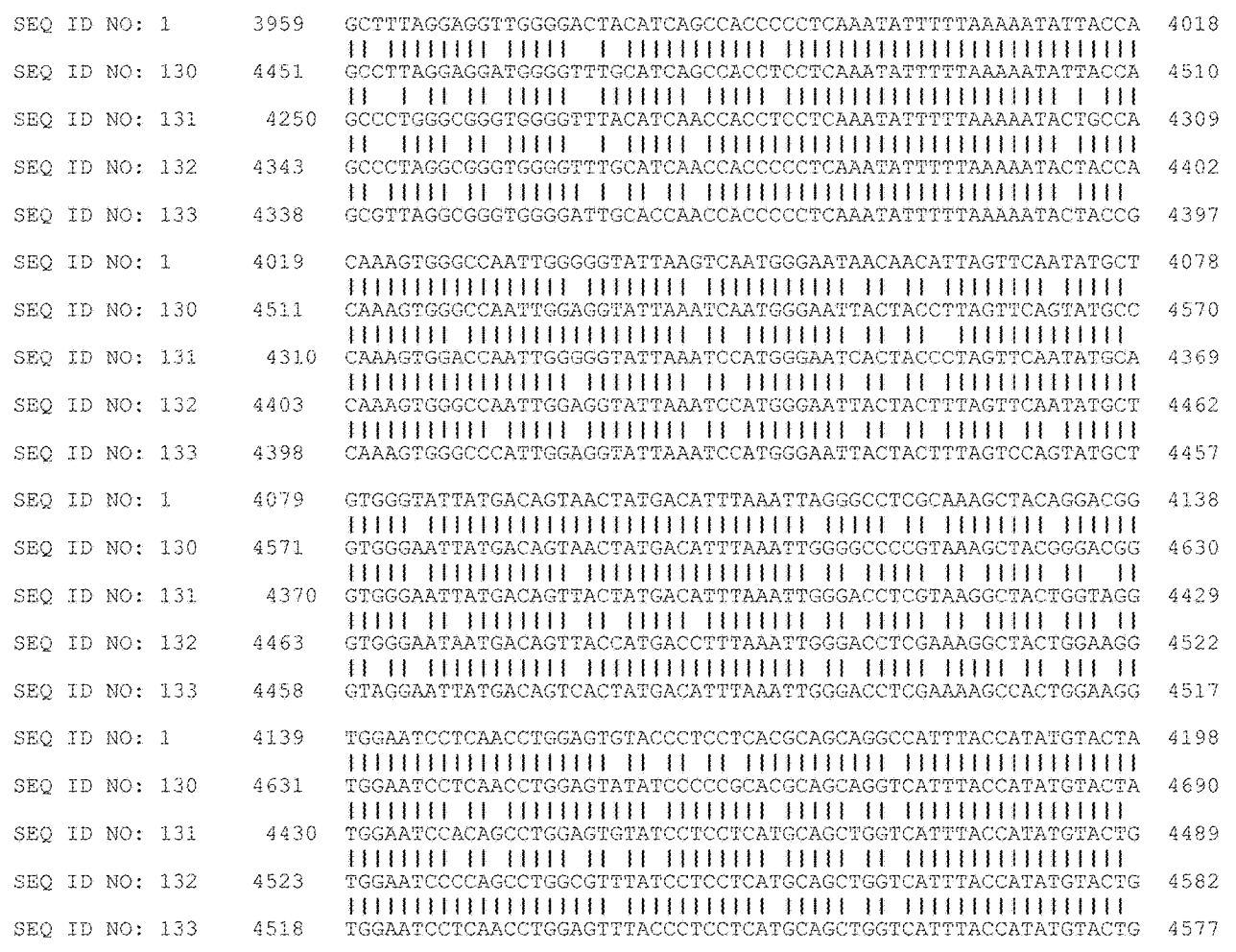

FIG. 4A-U shows an alignment of partial DNA sequences of the novel human parvovirus B19 variants of the invention (i.e., SEQ ID NO: 1 for the D11 variant, SEQ ID NO: 128 for the E3 variant, SEQ ID NO: 129 for the P1 variant); Au human parvovirus B19 DNA, genotype 1 (i.e., SEQ ID NO: 130 for Accession Number: M13178); A6 human parvovirus B19 DNA, genotype 2 (i.e., SEQ ID NO: 131 for Accession Number: AY064476); V9 human parvovirus B19 DNA, genotype 3 (i.e., SEQ ID NO: 132 for Accession Number: NC_004295); and D91.1 human parvovirus B19 DNA, genotype 3 (i.e., SEQ ID NO: 133 for Accession Number: AY083234). In the alignment, the nucleotide shown at position 1 for SEQ ID NO:1, SEQ ID NO:128, and SEQ ID NO: 129 corresponds to the nucleotide at position 154 in FIG. 1, 991 in FIG. 2A-B, and 1122 in FIG. 3A-B, respectively.

Figure 5C:
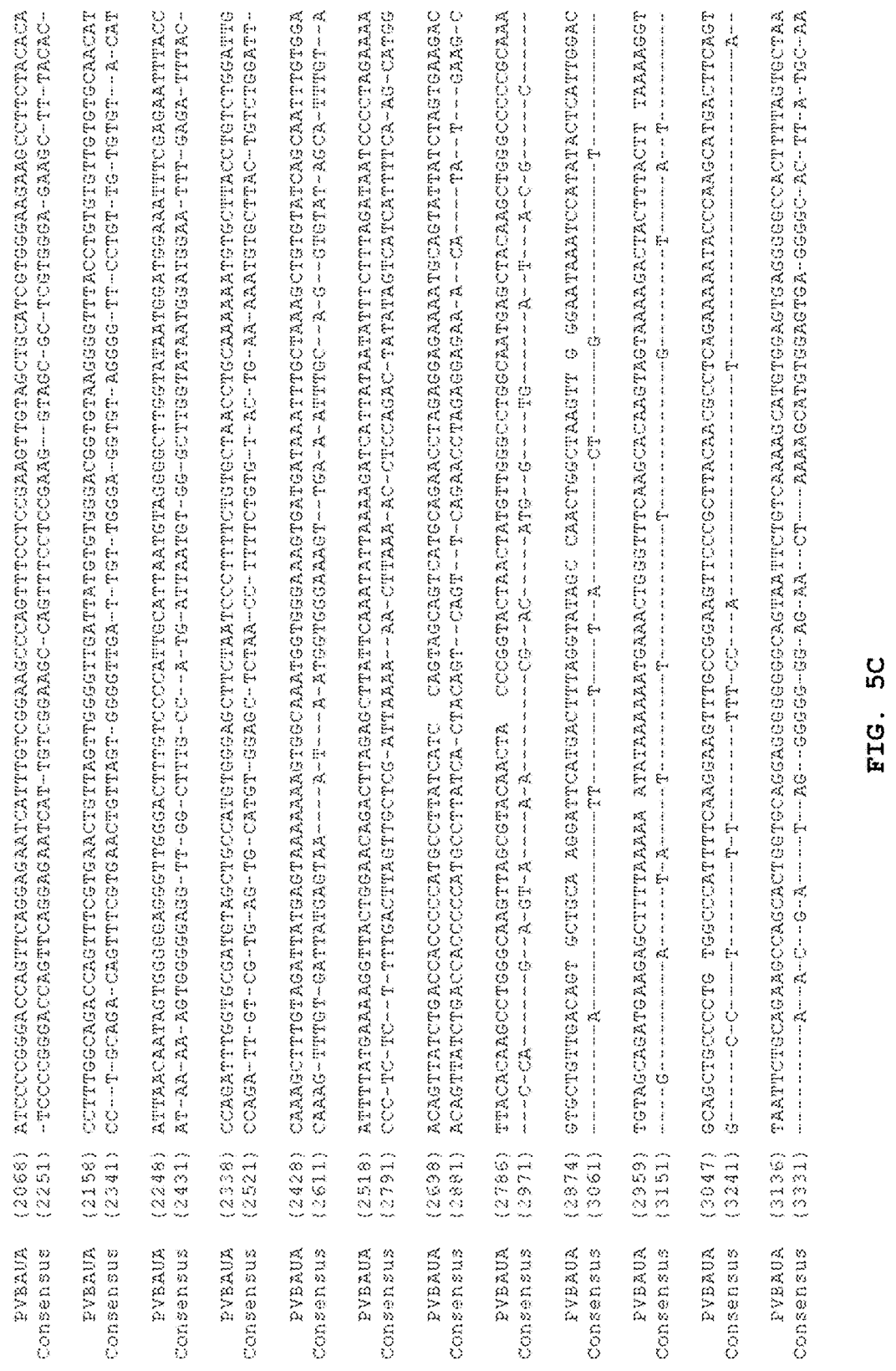

FIG. 5A-E shows alignment of 97% consensus sequence to parvovirus B19 Genotype 1 prototype strain Au (i.e., PVBAUA, SEQ ID NO:130).

FIG. 6 shows alignment of the parvovirus B19 Genotype 1 prototype strain Au (i.e., PVBAUA, SEQ ID NO:130) with the 97% consensus sequence showing the highly conserved region from nucleotides 1351 to 2426.

FIG. 7 shows alignment of the parvovirus B19 Genotype 1 prototype strain Au (i.e., PVBAUA SEQ ID NO:130) with the 97% consensus sequence showing the highly conserved region from nucleotides 3704 to 4804.

FIG. 10 shows target region and oligonucleotide sequences derived from highly conserved regions of the parvovirus B19 genome.

DETAILED DESCRIPTION

Figure 8:
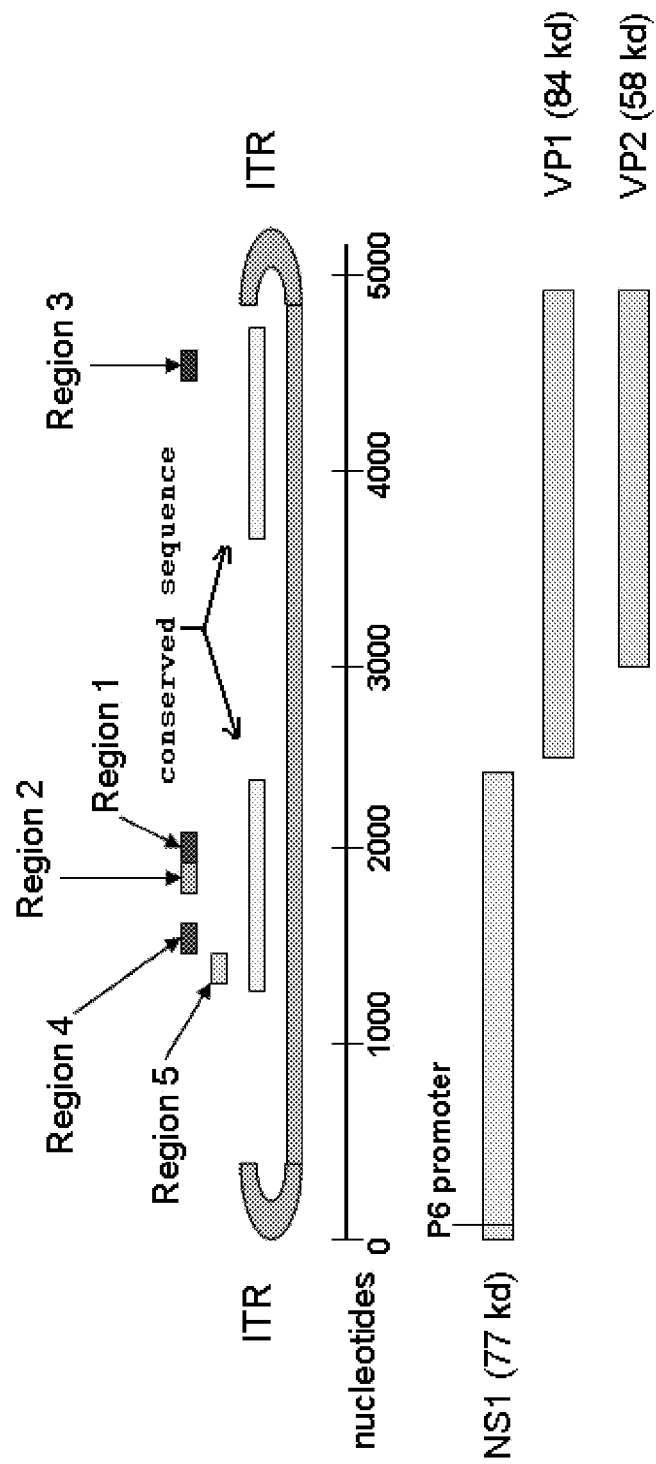
FIG. 8 shows a graphical depiction of the parvovirus B19 genome and transcription map showing conserved sequences and target regions. ITR—Inverted Terminal Repeat, NS1—Non-Structural Protein 1, VP1—Viral Protein 1, and VP2—Viral Protein 2.

It has been found in accordance with this invention novel human erythrovirus variants (herein named the "D11," "P1," or "E3" variant) that contain previously unreported variations in viral DNA sequence. While the new variants described herein share some nucleic acid homology with other previously known variants of the human erythrovirus family, regions of the viral genome show divergence. This divergence indicates three previously unknown human erythrovirus variants that have eluded current detection methods, and knowledge of these variants provides for new methods for viral screening and detection.

The term "human erythrovirus" herein refers to viral members of the genus *Erythrovirus*.

The term "parvovirus B19" or "B19" herein refers to parvovirus B19 of the family Parvoviridae including genotypes 1, 2, and 3. For example, "parvovirus B19" at least includes parvovirus B19 genotype 1 (e.g., GenBank Accession Number: M13178) and related variants such as, for example, A6 parvovirus B19 genotype 2 (e.g., GenBank Accession Number: AY064476), V9 human parvovirus B19 genotype 3 (e.g., GenBank Accession Number: NC_004295), D91.1 parvovirus B19 genotype 3 (e.g., GenBank Accession Number: AY083234), and the parvovirus B19 variants (i.e., D11, E3, and P1) of the present invention. Fryer et al., (*Emerg. Infect. Diseases* 2006 12:151-154) discloses a phylogenetic analysis of members of the Parvoviridae subfamily including members of the *Erythrovirus* genus.

The term "universal base" herein refers to a moiety that may be substituted for any base. The "universal base" need not contribute to hybridization, but should not significantly detract from hybridization. Exemplary universal bases include, without limitation, inosine, 5-nitroindole and 4-nitrobenzimidazole.

In one embodiment, the present invention provides an isolated nucleic acid molecule comprising a nucleotide sequence as set forth in SEQ ID NO: 1, SEQ ID NO: 128, SEQ ID NO: 129, or a complement thereof. In some embodiments, the isolated nucleic acid molecule comprises single-stranded or double-stranded nucleic acid. In other embodiments, the isolated nucleic acid molecule comprises ribonucleic acid (RNA), deoxyribonucleic acid (DNA), or any combination thereof.

The term "nucleic acid" or "nucleic acid molecule" herein broadly refers to a polymer of any size comprising RNA, DNA, modified RNA or DNA, spliced messenger RNA, RNA or DNA mimetics, or combinations thereof (e.g., RNA/DNA hybrids). The term, therefore, includes polymers composed of naturally-occurring nucleotide bases, sugars and covalent internucleoside (backbone) linkages as well as nucleic acid molecules having non-naturally-occurring portions that function similarly. Further, the term "nucleic acid molecule" also includes polymers that are double-stranded, single-stranded, or any combination thereof.

In another aspect of the invention, an isolated nucleic acid molecule is provided that can anneal to DNA or RNA of the novel parvovirus B19 variant (i.e., D11) of the invention, as well as to one or more of other parvovirus sequences such as, for example, sequences of Au, A6, V9, or D91.1 parvovirus, thereby providing probes and primers useful for detection of multiple forms in a single test. Thus, according to this aspect, the invention relates to nucleic acid molecules useful for detection of parvovirus B19, including the novel variant characterized by the nucleic acid sequence of SEQ ID NO:1, and one or more variants known as Au, A6, V9, and D91.1 (see FIG. 4). Accordingly, the present invention includes an isolated nucleic acid molecule comprising a sequence consisting of at least 12, at least 15, or at least 20 contiguous nucleotides or a complement thereof, wherein the contiguous nucleotides are contained in a nucleotide sequence selected from the group consisting of: (SEQ ID NO: 2), (SEQ ID NO: 3), (SEQ ID NO: 4), (SEQ ID NO: 5), (SEQ ID NO: 6), (SEQ ID NO: 7), (SEQ ID NO: 8), (SEQ ID NO: 9), (SEQ ID NO: 10), (SEQ ID NO: 11), (SEQ ID NO: 12), (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 24), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), (SEQ ID NO: 39), (SEQ ID NO: 40), (SEQ ID NO: 41), (SEQ ID NO: 42), (SEQ ID NO: 43), (SEQ ID NO: 44), (SEQ ID NO: 45), (SEQ ID NO: 46), (SEQ ID NO: 47), (SEQ ID NO: 48), (SEQ ID NO: 49), (SEQ ID NO: 50), (SEQ ID NO: 51), (SEQ ID NO: 52), (SEQ ID NO: 53), (SEQ ID NO: 54), (SEQ ID NO: 55), (SEQ ID NO: 56), (SEQ ID NO: 57), (SEQ ID NO: 58), (SEQ ID NO: 59), (SEQ ID NO: 60), (SEQ ID NO: 134), and (SEQ ID NO: 135).

In another aspect of the invention, an isolated nucleic acid molecule is provided that can anneal to DNA or RNA of the novel parvovirus B19 variants (i.e., D11, E3 and P1) of the invention, as well as to one or more other parvovirus sequences such as, for example, sequences of Au, A6, V9, or D91.1 parvovirus, thereby providing probes and primers useful for detection of multiple forms in a single test. Thus, according to this aspect, the invention relates to nucleic acid molecules useful for detection of parvovirus B19, including one or more of the novel variants characterized by the nucleic acid sequence of SEQ ID NO:1, SEQ ID NO:128, and SEQ ID NO: 129, and one or more variants known as Au, A6, V9, and D91.1. Accordingly, the present invention includes an isolated nucleic acid molecule comprising a sequence, or a complement thereof, present in an erythrovirus genome comprising a nucleotide sequence as set forth in SEQ ID NO:1, SEQ ID NO:128, and SEQ ID NO: 129, wherein the sequence is present in at least one other parvovirus genome. In one embodiment, the at least one other parvovirus genome is parvovirus B19 Au, A6, V9, and D91.1.

In another embodiment, the present invention includes an isolated nucleic acid molecule comprising a sequence consisting of at least 12, at least 15, or at least 20 contiguous nucleotides or a complement thereof, wherein the contiguous nucleotides are contained in a nucleotide sequence selected from the group consisting of: (SEQ ID NO: 13), (SEQ ID NO: 14), (SEQ ID NO: 15), (SEQ ID NO: 16), (SEQ ID NO: 17), (SEQ ID NO: 18), (SEQ ID NO: 19), (SEQ ID NO: 20), (SEQ ID NO: 21), (SEQ ID NO: 22), (SEQ ID NO: 23), (SEQ ID NO: 25), (SEQ ID NO: 26), (SEQ ID NO: 27), (SEQ ID NO: 28), (SEQ ID NO: 29), (SEQ ID NO: 30), (SEQ ID NO: 31), (SEQ ID NO: 32), (SEQ ID NO: 33), (SEQ ID NO: 34), (SEQ ID NO: 35), (SEQ ID NO: 36), (SEQ ID NO: 37), (SEQ ID NO: 38), (SEQ ID NO: 134), and (SEQ ID NO: 135).

In other embodiments, the present invention provides an isolated nucleic acid molecule consisting of a nucleotide sequence or a complement thereof, wherein the nucleotide sequence is selected from the group consisting of: (SEQ ID NO: 136), (SEQ ID NO: 137), (SEQ ID NO: 138), (SEQ ID NO: 139), (SEQ ID NO: 140), (SEQ ID NO: 141), (SEQ ID NO: 142), (SEQ ID NO: 143), (SEQ ID NO: 144), (SEQ ID NO: 145), (SEQ ID NO: 146), (SEQ ID NO: 147), (SEQ ID NO: 148), (SEQ ID NO: 149), (SEQ ID NO: 150), (SEQ ID NO: 151), (SEQ ID NO: 152), (SEQ ID NO: 153), (SEQ ID NO: 154), (SEQ ID NO: 155), (SEQ ID NO: 156), (SEQ ID NO: 157), and (SEQ ID NO: 158).

In other aspects, the isolated nucleic acid molecules allow for discrimination between the newly discovered D11 variant of the present invention and other known parvovirus B19 such as, for example, Au, A6, V9, and D91.1. Thus, the present invention provides an isolated nucleic acid molecule comprising at least 12, at least 15, or at least 20, contiguous nucleotides of a nucleotide sequence or its complement thereof. The nucleotide sequence is based on regions within the genome of the newly discovered D11 variant of the present invention. The at least 12, at least 15, or at least 20, contiguous nucleotides can provide for specific and/or sensitive detection of a human erythrovirus in a sample. Accordingly, the present invention includes an isolated nucleic acid molecule comprising at least 12, at least 15, or at least 20 contiguous nucleotides of a nucleotide sequence or a complement thereof, wherein the nucleotide sequence is selected from the group consisting of: (SEQ ID NO: 61), (SEQ ID NO: 62), (SEQ ID NO: 63), (SEQ ID NO: 64), (SEQ ID NO: 65), (SEQ ID NO: 66), (SEQ ID NO: 67), (SEQ ID NO: 68), (SEQ ID NO: 69), (SEQ ID NO: 70), (SEQ ID NO: 71), (SEQ ID NO: 72), (SEQ ID NO: 73), (SEQ ID NO: 74), (SEQ ID NO: 75), (SEQ ID NO: 76), (SEQ ID NO: 77), (SEQ ID NO: 78), (SEQ ID NO: 79), (SEQ ID NO: 80), (SEQ ID NO: 81), (SEQ ID NO: 82), (SEQ ID NO: 83), (SEQ ID NO: 84), (SEQ ID NO: 85), (SEQ ID NO: 86), (SEQ ID NO: 87), (SEQ ID NO: 88), (SEQ ID NO: 89), (SEQ ID NO: 90), (SEQ ID NO: 91), (SEQ ID NO: 92), (SEQ ID NO: 93), (SEQ ID NO: 94), (SEQ ID NO: 95), (SEQ ID NO: 96), (SEQ ID NO: 97), (SEQ ID NO: 98), (SEQ ID NO: 99), (SEQ ID NO: 100), (SEQ ID NO: 101), (SEQ ID NO: 102), (SEQ ID NO: 103), (SEQ ID NO: 104), (SEQ ID NO: 105), (SEQ ID NO: 106), (SEQ ID NO: 107), (SEQ ID NO: 108), (SEQ ID NO: 109), (SEQ ID NO: 110), (SEQ ID NO: 111), (SEQ ID NO: 112), (SEQ ID NO: 113), (SEQ ID NO: 114), (SEQ ID NO: 115), (SEQ ID NO: 116), (SEQ ID NO: 117), (SEQ ID NO: 118), (SEQ ID NO: 119), (SEQ ID NO: 120), (SEQ ID NO: 121), (SEQ ID NO: 122), (SEQ ID NO: 123), (SEQ ID NO: 124), (SEQ ID NO: 125), (SEQ ID NO: 126), and (SEQ ID NO: 127).

In one embodiment, the nucleotide sequence is selected from the group consisting of (SEQ ID NO: 61), (SEQ ID NO: 64), (SEQ ID NO: 65), (SEQ ID NO: 66), (SEQ ID NO: 68), (SEQ ID NO: 70), (SEQ ID NO: 81), (SEQ ID NO: 84), (SEQ ID NO: 86), (SEQ ID NO: 87), (SEQ ID NO: 88), (SEQ ID NO: 89), (SEQ ID NO: 97), (SEQ ID NO: 102), (SEQ ID NO: 109), SEQ ID NO: 114), (SEQ ID NO: 119), (SEQ ID NO: 120), (SEQ ID NO: 121), and (SEQ ID NO: 127).

In other aspects, the isolated nucleic acid molecules allow for discrimination between the newly discovered variants of the present invention (i.e., D11, E3, and P1) and at least one other known parvovirus B19 such as, for example, Au, A6, V9, and D91.1. Thus, the present invention provides an isolated nucleic acid molecule comprising a sequence present in an erythrovirus genome or a complement thereof, wherein the genome comprises a nucleotide sequence as set forth in SEQ ID NO:1, SEQ ID NO:128 or SEQ ID NO: 129, wherein the sequence is not present in at least one other parvovirus genome. The nucleotide sequence is based on regions of the genome of the newly discovered D11, E3 and/or P1 variants of the present invention. The contiguous nucleotides can provide for specific and/or sensitive detection of a human erythrovirus in a sample.

In another aspect, the present invention provides an isolated polynucleotide comprising a nucleotide sequence or a complement thereof. The nucleotide sequence is selected from the group consisting of:

```
                                                  (SEQ ID NO: 159)
5'-CATGTGTTAAAGTGGATTGATAAAAAATGTGG-3';

(SEQ ID NO: 160)
5'-CTACATCATTAAATGGAAAGTTTTCATTATTCCA-3';

(SEQ ID NO: 161)
5'-TGGAATAATGAAAATTTTCCATTTAATGATGT-3';
and (SEQ ID NO: 162)
5'-CCTTCATCCCAGACCACCAA-3'.
```

In other aspects, the present invention provides an isolated nucleic acid molecule that anneals under a stringent condition to a polynucleotide comprising a nucleotide sequence as set forth in SEQ ID NO: 1 or a complement thereof, but does not anneal under the stringent condition to other DNA or RNA molecules that may be present in a test sample (i.e., binds specifically to parvovirus B19 nucleic acid). In one embodiment, the nucleotide sequence is as set forth in SEQ ID NO: 128 or a complement thereof. In another embodiment, the nucleotide sequence is as set forth in SEQ ID NO: 129 or a complement thereof. As used herein, a stringent condition is a highly stringent condition or a moderately stringent condition.

Stringency conditions are known to those skilled in the art and can be found, for example, in *Current Protocols in Molecular Biology* (1999. Ausubel F M, Brent R, Kingston R E, Moore D D, Seidman J G, Smith J A, Struhl K, editors. John Wiley & Sons, Inc.) or Sambrook et al., *Molecular Cloning: A Laboratory Manual*, New York: Cold Spring Harbor Press (1989). Stringency conditions relate to the set of conditions under which nucleic acid hybrids comprising double-stranded regions are formed and/or maintained. It is well known in the art that two complementary single-stranded nucleic acids (DNA or RNA) can anneal to one another so that complexes called hybrids are formed. Formation or subsequent stability of a formed hybrid can be affected by the conditions under which hybridization (i.e., annealing) occurs, by any wash conditions subsequent to hybridization, or both. Thus, through one or more nucleic acid hybridization steps, which can precede one or more wash steps, two nucleic acid sequences having a certain degree of complementary identity to one another can anneal together and form a hybrid comprising one or more contiguous regions of double-stranded nucleic acid. Further, formation of hybrids can occur in a variety of environments such as, for example, in solution, with one component immobilized on a solid support such as a nylon membrane, nitrocellulose paper, polystyrene, or in situ (e.g., in suitably prepared cells or histological sections).

It is well known in the art that a number of factors affect hybrid formation and/or stability such as, for example, temperature, duration, frequency, or salt or detergent concentration of the hybridization and/or wash conditions. Thus, for example, the stringency of a condition can be primarily due to the wash conditions, particularly if the hybridization condition used is one which allows less stable hybrids to form along with stable hybrids (e.g., wash conditions at higher stringency can remove less stable hybrids). In general, longer sequences require higher temperatures for proper annealing, while shorter sequences need lower temperatures. Hybridization generally depends on the ability of denatured nucleic acids to reanneal when complementary strands are present in a favorable environment at temperatures below their melting temperature. The higher the degree of desired homology between two sequences, the higher the relative temperature which can be used. As a result, it follows that higher relative temperatures would tend to make the reaction conditions more stringent, while lower temperatures less so.

Generally, stringency can be altered or controlled by, for example, manipulating temperature and salt concentration during hybridization and washing. For example, a combination of high temperature and low salt concentration increases stringency. The skilled artisan will recognize how to adjust the temperature, ionic strength, etc. of the stringent condition as necessary to accommodate factors such as polynucleotide length and the like.

A "highly stringent condition," as defined herein, can be identified by a condition that comprises 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a wash consisting of 0.1×SSC at 55° C.

A "moderately stringent condition," as defined herein, can be identified by washing and/or hybridization conditions less stringent than those described above for a highly stringent condition. An example of a moderately stringent condition is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing in 1×SSC at about 35-50° C.

Sometimes, nucleic acid duplex or hybrid stability is expressed as the melting temperature or $T_m$, which is the temperature at which 50% of one nucleic acid dissociates from a nucleic acid duplex. Accordingly, this melting temperature can be used to define the required stringency conditions. If sequences are related and substantially identical to each other, rather than identical, then it can be useful to first establish the lowest temperature at which only homologous annealing occurs with a particular concentration of salt (e.g., SSC or SSPE). Then, assuming 1% mismatching results in a 1° C. decrease in the $T_m$, the temperature of the final wash in the hybridization reaction is reduced accordingly (for example, if sequences having >95% identity with each other are sought, the final wash temperature is decreased by 5° C.). In practice, the change in $T_m$ can be between 0.5° C. and 1.5° C. per 1% mismatch.

In other aspects, the present invention provides an isolated nucleic acid molecule that anneals under a highly stringent condition to a polynucleotide comprising a nucleotide sequence as set forth in SEQ ID NO: 1 or a complement thereof, wherein the isolated nucleic acid molecule does not anneal under the highly stringent condition to a DNA or a RNA of parvovirus B19 Au, A6, V9, or D91.1 variant. In one embodiment, the polynucleotide comprises the nucleotide sequence as set forth in SEQ ID NO: 128 or a complement thereof. In another embodiment, the polynucleotide comprises the nucleotide sequence as set forth in SEQ ID NO: 129 or a complement thereof. Stringency conditions are as described above.

The annealing portion of a hybridizing nucleic acid molecule can vary in length but is typically at least about 6, illustratively, at least about 10, 12, 15, 20, 25, 30, 50, 60, 70, 80, 90, 100, 150, 200, 250, 300, 400, 500, 600, 700, 800, 900, or 1000 nucleotides in length. However, binding enhancers such as minor groove binding nucleic acids can allow annealing to shorter nucleic acid targets with increased sequence-specificity compared to ordinary length nucleic acids (Kutyavin I V, et al., *Nucleic Acid Research* 2000 28:655-661). The annealing portion of the annealing nucleic acid is at least 60%, e.g., at least 70%, 80%, 95% or at least 98% identical to the sequence of a portion or an of a nucleic acid expressly described herein, or its complement. Annealing nucleic acids of the type described herein can be used, for example, as cloning probes, primers (e.g., a PCR primer), or diagnostic probes.

As described above, oligonucleotide primers and probes can be derived from the nucleic acid sequences disclosed herein. In various embodiments, primers and probes are used in combination with each other. The present invention finds use in a variety of different applications including, but not limited to, research, medical, and diagnostic applications.

In some embodiments, primers and probes can be designed from regions of SEQ ID NO: 1, SEQ ID NO: 128, or SEQ ID NO:129, wherein the primers and probes each comprise one or more conserved nucleotides also present in a corresponding region of the genome of another human erythroviruses such as parvovirus B19 Au, A6, V9, and D91.1. For example, a nucleotide sequence alignment can be performed with at least two parvovirus sequences using, e.g., a computer algorithm to determine identical contiguous nucleotide sequences common to the at least two parvovirus. Accordingly, the primers and probes can provide for reagents for use in, for example, a parvovirus detection assay or kit thereby expanding the repertoire of parvovirus variants that can be detected by the assay or kit.

In another embodiment, the present invention provides a kit comprising at least one primer and at least one probe, wherein the at least one primer comprises a primer nucleic acid sequence as set forth in (SEQ ID NO: 136), (SEQ ID NO: 137), (SEQ ID NO: 139), (SEQ ID NO: 140), (SEQ ID NO: 142), (SEQ ID NO: 144), (SEQ ID NO: 145), (SEQ ID NO: 146), (SEQ ID NO: 149), (SEQ ID NO: 151), (SEQ ID NO: 152), (SEQ ID NO: 154), or (SEQ ID NO: 155), wherein the at least one probe comprises a probe sequence consisting of: (SEQ ID NO: 138), (SEQ ID NO: 141), (SEQ ID NO: 143), (SEQ ID NO: 147), (SEQ ID NO: 148), (SEQ ID NO: 150), (SEQ ID NO: 153), (SEQ ID NO: 156), (SEQ ID NO: 157), (SEQ ID NO: 158), or complements thereof.

In another embodiment, the kit comprises a forward primer, a reverse primer, and a probe, wherein the forward primer comprises a forward primer nucleic acid sequence as set forth in (SEQ ID NO: 136), (SEQ ID NO: 139), (SEQ ID NO: 142), (SEQ ID NO: 145), (SEQ ID NO: 149), (SEQ ID NO: 151), or (SEQ ID NO:154, wherein the reverse primer comprises a reverse primer nucleic acid sequence as set forth in (SEQ ID NO: 137), (SEQ ID NO: 140), (SEQ ID NO: 144), (SEQ ID NO: 146), (SEQ ID NO: 152), or (SEQ ID NO:155, wherein the probe comprises a probe nucleic acid sequence as set forth in (SEQ ID NO: 136), (SEQ ID NO: 137), (SEQ ID NO: 138), (SEQ ID NO: 139), (SEQ ID NO: 140), (SEQ ID NO: 141), (SEQ ID NO: 142), (SEQ ID NO: 143), (SEQ ID NO: 144), (SEQ ID NO: 145), (SEQ ID NO: 146), (SEQ ID NO: 147), (SEQ ID NO: 148), (SEQ ID NO: 149), (SEQ ID NO: 150), (SEQ ID NO: 151), (SEQ ID NO: 152), (SEQ ID NO: 153), (SEQ ID NO: 154), (SEQ ID NO: 155), (SEQ ID NO: 156), (SEQ ID NO: 157), (SEQ ID NO: 158), or complements thereof. In some embodiments, the probe nucleic acid sequence is as set forth in (SEQ ID NO: 138), (SEQ ID NO: 141), (SEQ ID NO: 143), (SEQ ID NO: 147), (SEQ ID NO: 148), (SEQ ID NO: 150), (SEQ ID NO: 153), (SEQ ID NO: 156), (SEQ ID NO: 157), (SEQ ID NO: 158), or complements thereof.

In some aspects, the present invention provides a method for detecting a parvovirus B19 in a sample. The method comprises:

a) performing PCR with at least a portion of the sample using a forward primer having a forward primer nucleic acid sequence and a reverse primer having a reverse primer nucleic acid sequence, wherein the forward primer nucleic acid sequence is as set forth in (SEQ ID NO: 136), (SEQ ID NO: 139), (SEQ ID NO: 142), (SEQ ID NO: 145), (SEQ ID NO: 149), (SEQ ID NO: 151), or (SEQ ID NO:154, wherein the reverse primer nucleic acid sequence is as set forth in (SEQ ID NO: 137), (SEQ ID NO: 140), (SEQ ID NO: 144), (SEQ ID NO: 146), (SEQ ID NO: 152), or (SEQ ID NO:155); and (b) determining the presence or absence of an amplicon, wherein the presence of the amplicon is indicative of the presence of the parvovirus B19 in the sample. In one embodiment, determining comprises annealing an oligonucleotide to the amplicon, wherein the oligonucleotide comprises a sequence as set forth in (SEQ ID NO: 138), (SEQ ID NO: 141), (SEQ ID NO: 143), (SEQ ID NO: 147), (SEQ ID NO: 148), (SEQ ID NO: 150), (SEQ ID NO: 153), (SEQ ID NO: 156), (SEQ ID NO: 157), (SEQ ID NO: 158), or complements thereof. In one embodiment, the oligonucleotide further comprises a detectable label. In another embodiment, the PCR is a real-time PCR.

In some embodiments, primers and probes can be designed from regions of SEQ ID NO: 1, SEQ ID NO: 128, or SEQ ID NO:129 that comprise one or more unique nucleotides as compared to the corresponding region of the genome of other human erythroviruses such as parvovirus B19 Au, A6, V9, and D91.1. Accordingly, the primers and probes can provide for assays that facilitate detection of a parvovirus B19 as well as provide for assays that distinguish between one or more of the new variants disclosed herein or other previously known human erythroviruses such as parvovirus B19 Au, A6, V9, and D91.1. Accordingly, the primers and probes can provide for a more specific parvovirus detection assay that can discriminate from among the parvovirus variants.

In other aspects, the present invention provides a method for determining parvovirus B19 in a sample. The method comprises:

(a) amplifying parvovirus B19 nucleic acid in the sample with at least one pair of primers comprising a first primer and a second primer, wherein the first primer comprises a nucleotide sequence as set forth in (SEQ ID NO:154) or (SEQ ID NO:159); and (b) detecting an amplicon generated in step (a), wherein detection of the amplicon indicates presence of the parvovirus B19 in the sample.

In one embodiment, the detecting step (b) comprises contacting the amplicon with a polynucleotide probe comprising a nucleotide sequence as set forth in (SEQ ID NO:160) or (SEQ ID NO:161). Preferably, the polynucleotide probe further comprises at least one detectable label. In another embodiment, the second primer comprises the sequence shown in (SEQ ID NO:162).

In other embodiments, the polynucleotide probe comprises a quencher molecule coupled to a pyrimidine ring of a thymine base. In one embodiment, the thymidine base is in nucleotide position 10 of (SEQ ID NO:160). For example, the quencher can be a Black Hole Quencher® (e.g., BHQ1).

In still further embodiments, the polynucleotide probe comprises a quencher molecule incorporated into the backbone of the probe. In one embodiment, the quencher replaces the nucleotide at position 10 of (SEQ ID NO:160).

Another example of a hybridization assay probe is a structure referred to as a "molecular beacon," which is described, for example, in U.S. Pat. No. 5,925,517. Molecular beacons are oligonucleotide hybridization probes that comprise a label pair and form a stem-and-loop structure. The loop component comprises a probe sequence that is complementary to a target sequence. The stem comprises an affinity pair (or nucleic acid arms) that hold the probe in a closed conformation in the absence of a target nucleic acid sequence. The stem is formed by the annealing of complementary arm sequences that are located on either side of the probe sequence. Hybridization of the target nucleic acid and the target complement sequence separates the members of the affinity pair, thereby shifting the probe to an open conformation. The shift to the open confirmation is detectable due to reduced interaction of the label pair, which may be, for example, a fluorophore and a quencher (e.g., DABCYL and EDANS).

The simultaneous use of two or more probes using donor-acceptor energy transfer is known in the art. Accordingly, molecular beacons can be synthesized that possess differently colored fluorophores, enabling assays to be carried out that simultaneously detect different targets in the same reaction. For example, multiplex assays can contain a number of different primer sets, each set enabling the amplification of a unique gene sequence from a different pathogenic agent, and a corresponding number of molecular beacons can be present, each containing a probe sequence specific for one of the amplicons, and each labeled with a fluorophore of a different color. The color of the resulting fluorescence, if any, identifies the pathogenic agent in the sample, and the number of amplification cycles required to generate detectable fluorescence provides a quantitative measure of the number of target organisms present. If more than one type of pathogen is present in the sample, the fluorescent colors that occur identify which are present. Moreover, due to the inherent design of gene amplification assays, the use of molecular beacons enables the abundance of a rare pathogen to be determined in the presence of a much more abundant pathogen.

In general, primers can provide for specific amplification (e.g., by PCR) of a target nucleic acid to produce an amplification product (also referred to as an "amplicon"). In one embodiment, the target nucleic acid is DNA or RNA of the novel human erythrovirus disclosed herein. In some embodiments, the target nucleic acid comprises a genome comprising a nucleotide sequence as set forth in SEQ ID NO: 1. In other embodiments, the target nucleic acid comprises an RNA molecule transcribed from a genome comprising a nucleotide sequence as set forth in SEQ ID NO: 1. In one embodiment, the genome comprises the nucleotide sequence as set forth in SEQ ID NO: 128 or SEQ ID NO: 129.

In some embodiments, a primer sequence can be at least about 10 nucleotides in length, illustratively about 10 to about 100, about 12 to about 75, about 14 to about 65, about 16 to about 60, about 20 to about 55, about 25 to about 50, or about 30 to about 45, and the like. In one embodiment, a primer sequence is about 15 to about 20 nucleotides in length.

Probes are generally designed so as to have a nucleotide sequence complementary to one or more variant nucleotides within a target region sequence. Probes suitable for use in amplification-based detection methods can be designed from any sequence positioned within the sequence of an amplification product that would be produced using two selected primers. In various embodiments, a probe sequence can be at least about 10 nucleotides in length, illustratively about 10 to about 100, about 12 to about 75, about 14 to about 65, about 16 to about 60, about 20 to about 55, about 25 to about 50, or about 30 to about 45, and the like. In one embodiment, a probe sequence is about 15 to about 20 nucleotides in length.

Depending on the number of nucleotide residues, a nucleic acid molecule also can be referred to as an "oligonucleotide" or "oligomer." The term "oligonucleotide" or "oligomer" typically refers to a nucleic acid molecule having a relatively short sequence of nucleotides. For example, an oligonucleotide can be about 5 to about 500 nucleotide residues in length. Oligonucleotides, which can be double-stranded or single-stranded, may be used as single-stranded probes for detecting complementary DNA or RNA because they can bind readily to their complements. Non-limiting examples of procedures that use oligonucleotides are nucleic acid testing (NAT), DNA microarrays, amplified fragment-length polymorphism (AFLP) analysis, fragment analysis, Southern blots, and fluorescent in situ hybridization (FISH). Oligonucleotides composed of DNA are often used in the polymerase chain reaction (PCR), a procedure well-known to those skilled in the art. In this regard, the oligonucleotide also can be referred to as a "primer," which is a short piece of DNA that binds to its complementary target sequence. This generates a place for a polymerase to bind and extend the primer by the addition of nucleotides to make a complementary copy of the target sequence. An oligonucleotide can also be referred to as a "probe" which is a short piece of DNA or RNA that can be used to detect and identify specific DNA or RNA molecules bearing the complementary sequence. Probe detection is achieved through fluorescence, colorimetry, radioactivity, antigen binding, or enzymatic activity.

In some embodiments, the isolated nucleic acid molecule is an oligonucleotide having at least about 5 nucleotide residues in length, illustratively about 5 to about 500, about 8 to about 400, about 10 to about 300, about 12 to about 200, about 14 to about 100, about 16 to about 90, about 18 to about 80, about 20 to about 70, about 25 to about 60, or about 30 to about 50.

One skilled in the art will appreciate that the isolated nucleic acid molecules of the present invention can be obtained by standard molecular biology techniques such as PCR and others described in *Current Protocols in Molecular Biology* (1999. Ausubel F M, Brent R, Kingston R E, Moore D D, Seidman J G, Smith J A, Struhl K, editors. John Wiley & Sons, Inc.) or by chemical synthesis or by nucleic acid analogs.

Methods involving chemical synthesis may be automated and commercially available and can include, for example, phosphodiester, phosphotriester, or phosphoramidite methods. U.S. Pat. Nos. 4,458,066; 4,415,732; and *Meth. Enzymol.* 1979 68:90 and 109, which are incorporated herein by reference, disclose examples of chemical synthesis methods. Chemical nucleic acid synthesis allows for the incorporation of unnatural or modified bases, as well as a variety of labeling moieties, into a nucleic acid molecule. Further, modified backbone chemistries such as, for example, peptide linkages, phosphorothioates, phosphoroamidates, phosphotriesters, 2'-O-Methyl RNA, 2'-O—Mt RNA, P-Ethoxy DNA, and P-Ethoxy 2'-O—Mt RNA are also readily available and known in the art. Furthermore, the uses of cross-linkable probes in nucleic acid hybridization assays to cross-link to target sequences are known in the art. For example, compounds based on furocoumarin or psoralen attached to nucleic acid molecules through adduct formation are described in U.S. Pat. No. 4,826,967 and U.S. Pat. No. 5,082,934, both incorporated herein by reference, describes a photoactivatable nucleoside analogue comprising a coumarin moiety linked through its phenyl ring to the 1-position of a ribose or deoxyribose sugar moiety in the absence of an intervening base moiety.

Nucleic acid analogs and mimics have similar chemical structures as native nucleic acid molecules but with unique modifications. Nucleic acid analogs, such as locked nucleic acids (LNAs), peptide nucleic acids (PNAs), and morpholinos, improve the capabilities of traditional nucleic acid molecules beyond the limitations associated with standard nucleic acids chemistry (Karkare S and Bhatnagar D. *Appl. Microbiol. Biotechnol.* 2006 71:575-586.) Such nucleic acid analogs greatly expand and improve the capabilities to detect and identify related nucleic acid sequences.

In some aspects, an isolated nucleic acid molecule of the present invention further comprises one or more heterologous nucleotides. The term "heterologous nucleotides" herein refers to a nucleotide or nucleotides that are not a natural part of the isolated nucleic acid molecule but which are naturally or artificially joined to the isolated nucleic acid molecule. Examples of a heterologous nucleic acid sequence include, but is not limited to, a vector sequence, a sequence that is complementary to a base sequence of a purification probe, a control sequence such as, for example, an enhancer or a promoter sequence (i.e., a sequence that is recognized by an RNA polymerase that binds to that sequence and initiates transcription to produce RNA transcripts), and a sequence comprising one or more restriction enzyme sites.

The term "control sequence" herein refers to sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, messenger RNA splicing signals, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

In one embodiment, the one or more heterologous nucleotides comprise a sequence that is complementary to a base sequence of a purification probe. The purification probe can be joined to solid supports such as, for example, a matrix or particles free in solution. Non-limiting examples of a solid support include nitrocellulose, nylon, glass, polyacrylate, mixed polymers, polystyrene, silane polypropylene, and magnetically-attractable particles. For example, the purification probe, which may comprise a DNA or RNA sequence, can be labeled with amine or biotin tags via a cross-linker. These biotin or amine labeled purification probes are then amenable to immobilization and detection strategies that allow in vitro nucleic acid:nucleic acid or protein:nucleic acid interactions. Thus, annealing of the heterologous segment of the isolated nucleic acid molecule with its complementary base sequence of the purification probe can facilitate sample purification of molecules that anneal to the virus-specific sequence segment of the isolated nucleic acid molecule. U.S. Pat. No. 6,534,273, incorporated herein by reference, describes a method for capturing a target nucleic acid molecule in a sample onto a solid support.

In one embodiment, the isolated nucleic acid molecules of the present invention are joined to a solid support such as those described above.

In some embodiments, the one or more heterologous nucleotides comprise one or more repeating base sequences, for example, one or more repeating base sequences that are complementary to one or more repeating base sequences of the purification probe. A repeating base sequences can be a regularly repeating base sequence, such as those formed, for example, by nucleic acid homopolymers of poly-adenine ($A_n$), poly-thymine ($T_n$), poly-cytosine ($C_n$), poly-guanine ($G_n$), and poly-uridine ($U_n$). Repeating sequences also can include mixed polymers, such as AT repeats ($[AT]_n$), and the like.

The number of bases of the repeating base sequence of the one or more heterologous nucleotides of the isolated nucleic acid molecule can be equal to, greater than, or less than the number of bases of the repeating base sequence of the purification probe. The lengths of the complementary repeating sequences can determine the melting temperature ($T_m$) of the heterologous segment:purification probe complex. In one embodiment, the repeating base sequence of the heterologous segment is longer than the complementary repeating base sequence of the purification probe. In another embodiment, the repeating base sequence of the heterologous segment or the purification probe can be at least about 5 bases in length, illustratively about 5 to about 40, about 10 to about 30, or about 15 to about 20, and the like.

In other embodiments, the one or more heterologous nucleotides comprise an operably linked control sequence. In one embodiment, the control sequence is an enhancer or a promoter sequence that is specifically recognized by an RNA polymerase that binds to that sequence and initiates transcription to produce RNA transcripts. Non-limiting examples of promoters recognized by an RNA polymerase include promoters such as T3, T7, or SP6. Thus, an isolated nucleic acid molecule can be used in a variety of nucleic acid based assays including assays that use an RNA polymerase to produce multiple RNA transcripts such as, for example, transcription-mediated amplification (TMA) assay as described in *Nature* 350:91-92 (1991); and U.S. Pat. No. 5,399,491, both incorporated herein by reference.

Optionally, the isolated nucleic acid molecules of the present invention can be coupled to a label that can be detected. The label can be joined directly or indirectly to the isolated nucleic acid molecule. The labeling of a nucleic acid can be performed by covalently attaching a detectable group (label) to either an internal or terminal position, for example. One skilled in the art knows that there are a variety of ways for derivatizing oligonucleotides with reactive functionalities that permit the addition of a label. A number of approaches are available for directly attaching labels to nucleic acid molecules and for biotinylating probes so that radioactive, fluorescent, chemiluminescent, enzymatic, or electron dense labels can be attached via avidin. Non-limiting examples of references describing labels and methods for labeling nucleic acids include U.S. Pat. No. 4,605,735; U.S. Pat. No. 4,757,141; U.S. Pat. No. 6,965,020; *Nucl. Acids Res.* 5:363 (1978); *Nucl. Acids Res.* 13:1529 (1985); *Nucl. Acids Res.* 15:3131 (1987); *Nucl. Acids Res.* 15:6455 (1987); *Nucl. Acids Res.* 13:4485 (1985); *Nucl. Acids Res.* 15:4837 (1987); and *Anal. Biochem.* 169:1-25 (1988), which are incorporated herein by reference for their disclosure relating to labeling of nucleic acids.

The isolated nucleic acid molecules of the present invention may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

Further, a viral protein encoded by an isolated nucleic acid molecule comprising an open reading frame or a complement thereof, wherein the open reading frame is comprised in SEQ ID NO: 1, SEQ ID NO 128, or SEQ ID NO: 129 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the protein-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, α factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179), or the signal described in WO/90/13646. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells is those that enable the identification of cells competent to take up the viral protein-encoding nucleic acid, such as DHFR or thymidine kinase. An appropriate host cell when wild-type DHFR is employed is the CHO cell line deficient in DHFR activity, prepared and propagated as described by *Proc. Natl. Acad. Sci. USA* 77:4216 (1980). A suitable selection gene for use in yeast is the trp1 gene present in the yeast plasmid YRp7 as described by *Nature* 282:39 (1979); *Gene* 7:141 (1979); and *Gene* 10:157 (1980). The trp1 gene provides a selection marker for a mutant strain of yeast lacking the ability to grow in tryptophan, for example, ATCC No. 44076 or PEP4-1 as described by *Genetics* 85:12 (1977).

Expression and cloning vectors usually contain a promoter operably linked to the viral-protein-encoding nucleic acid sequence to direct mRNA synthesis. Promoters recognized by a variety of potential host cells are well known. Promoters suitable for use with prokaryotic hosts include the β-lactamase and lactose promoter systems as described by *Nature* 275:615 (1978) and *Nature* 281:544 (1979), alkaline phosphatase, a tryptophan (trp) promoter system as described by *Nucl. Acids Res.* 8:4057 (1980) and EP 36,776, and hybrid promoters such as the tac promoter as described in *Proc. Natl. Acad. Sci. USA* 80:21 25 (1983). Promoters for use in bacterial systems also will contain a Shine-Dalgarno (S.D.) sequence operably linked to the DNA encoding the viral protein.

Examples of suitable promoting sequences for use with yeast hosts include the promoters for 3-phosphoglycerate kinase described in *J. Biol. Chem.* 255:2073 (1980) or other glycolytic enzymes described in *J. Adv. Enzyme Reg.* 7:149 (1968) and *Biochemistry* 17:4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Viral protein transcription from vectors in mammalian host cells is controlled, for example, by promoters obtained from the genomes of viruses such as polyoma virus, fowlpox virus (GB 2,211,504), adenovirus (such as Adenovirus 2), bovine papilloma virus, avian sarcoma virus, cytomegalovirus (CMV), a retrovirus, hepatitis-B virus, and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the viral protein by higher eukaryotes may be increased by inserting an enhancer sequence into the vector. Enhancers are cis-acting elements of DNA, usually about 10 to about 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the CMV early promoter enhancer, the polyoma enhancer on the late side of the replication origin, and adenovirus enhancers. The enhancer may be spliced into the vector at a position 5 or 3' to the viral protein coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly upstream of the polyadenylation site in untranslated regions of eukaryotic or viral DNAs or cDNAs. These regions contain nucleotide segments transcribed as polyadenylated fragments in the untranslated portion of the mRNA encoding the viral protein.

Other methods, vectors, and host cells suitable for adaptation to the synthesis of viral proteins in recombinant vertebrate cell culture are described in *Nature* 293:620 625 (1981); *Nature* 281:4046 (1979); EP 117,060; and EP 117,058.

A host cell can be transfected or transformed with the isolated nucleic acid molecules of the present invention (or with expression or cloning vectors comprising them) and cultured in conventional nutrient media modified as appropriate for inducing viral production, inducing promoters, selecting transformants, or amplifying the genes encoding the desired sequences. In one embodiment, the host cell is an erythroid cell. In another embodiment, the erythroid cell is a human erythroid cell.

The culture conditions, such as media, temperature, pH, and the like, can be selected by the skilled artisan without undue experimentation. In general, principles, protocols, and practical techniques for maximizing the productivity of cell cultures can be found in M. Butler, Mammalian Cell Biotechnology: a Practical Approach, IRL Press (1991) and Sambrook et al., supra.

Methods of eukaryotic cell transfection and prokaryotic cell transformation are known to the ordinarily skilled artisan, for example, $CaCl_2$, $CaPO_4$, liposome-mediated, and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by *Gene* 23:315 (1983) and WO 89/05859. For mammalian cells without such cell walls, the calcium phosphate precipitation method described in *Virology* 52:456 457 (1978) can be employed. General aspects of mammalian cell host system transfections are described in U.S. Pat. No. 4,399,216. Transformations into yeast are typically carried out according to the method as described in *J. Bact.* 130:946 (1977) and *Proc. Natl. Acad. Sci. (USA)* 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see, for example, *Methods in Enzymology* 185:527 (1990) and *Nature* 336:348 (1988).

In various other aspects, the present invention provides an isolated nucleic acid molecule comprising an open reading frame or its complement thereof, wherein the open reading frame is comprised in SEQ ID NO: 1. In one embodiment, the open reading frame is comprised in SEQ ID NO: 128. In another embodiment, the open reading frame is comprised in SEQ ID NO: 129.

In some aspects, the present invention provides an isolated human erythrovirus having a genome comprising a nucleotide sequence as set forth in SEQ ID NO: 1. In one embodiment, the nucleotide sequence is as set forth in SEQ ID NO:128 or SEQ ID NO:129.

In other aspects, the present invention provides a kit. The kit can be developed using the nucleic acid sequences disclosed herein. These sequences can be used as primers in nucleic acid amplification reactions, and/or as probes in a nucleic acid hybridization method. The kits are useful for determining the presence of a parvovirus nucleic acid sequence in a sample. Components in the kit can either be obtained commercially or made according to well known methods in the art. In addition, the components of the kit can be in solution or lyophilized as appropriate. In one embodiment, the components are in the same compartment, and in another embodiment, the components are in separate compartments. In the preferred embodiment, the kit further comprises instructions for use.

The following examples are provided for illustration only.

EXAMPLES

Example 1

Detection of Parvovirus B19 D11 Variant by PCR

The D11 variant is detected from a biological source such as, for example, plasma, blood, bone marrow, or tissue sample for organ screening.

Approximately 1 ml of plasma or other biological source sample is added to approximately 200 μl of a buffered solution containing reagents designed to facilitate the precipitation of parvovirus B19 virions. To facilitate capsid disruption and pelleting, the buffered solution contains a chaotropic agent (e.g., guanidine isothiocyanate) and/or a detergent (e.g., sodium dodecyl sulfate (SDS)). Samples are mixed thoroughly by vortexing or inversion, and centrifuged. The supernatant is discarded and approximately 600 μl of a buffered solution containing a chaotropic agent such as, for example, guanidine thiocyanate is added to the pellet to completely disrupt the viral capsids. The parvovirus B19 DNA is then precipitated using, for example, approximately 700 μl isopropanol. Samples are thoroughly mixed by vortexing or inversion, and centrifuged using conditions that allow for the majority of the DNA to be recovered. Optionally, the pellet is washed, for example with approximately 1 ml 70% ethanol. After centrifugation, the parvovirus B19 variant DNA is recovered following resuspension of the pellet in a buffered solution to a volume (e.g., 200 μl) that allows for subsequent DNA amplification.

The D11 variant nucleic acid is amplified via PCR using techniques well-known in the art. For example, about 35 to 45 μl of a working master mix comprising of i) a buffer solution, ii) D 11 variant-specific oligonucleotides of which one is biotinylated on its 5' end, iii) dideoxy-trinucleotides, and iv) DNA polymerase is added into a PCR tube or plate for amplification. Five to 15 μl of the resuspended sample is added to the PCR tube or plate containing the working master mix. Using a standard PCR thermocycler, such as the BioRad iCycler (Bio-Rad Laboratories), the samples and all relevant controls are subjected to PCR amplification. The PCR amplification condition comprises, for example, i) a step of denaturation (e.g. 94° C. for 60 seconds), ii) about forty cycles comprising thermal denaturation (e.g. 94° C. for 15 seconds) and polymerase extension (e.g. 65° C. for 30 seconds), and iii) a final step of polymerase extension (e.g. 60° C. for 7 minutes).

Following amplification, the resulting amplicons are detected using a variety of methods well known in the art. For example, the amplicons are detected by first denaturing the resulting amplified product and annealing the denatured nucleic acid sequences with complementary RNA probes to form RNA:DNA complexes. RNA probes are designed from the parvovirus B19 variant sequence. The complexes will be captured on streptavidin-coated plates and detected and/or quantified using, for example, antibodies directed to the complexes in an ELISA format.

There are a variety ELISA formats known in the art. For example, fifty μl of a sample diluent (e.g. Multiprep Specimen Diluent (MP DIL) (Roche Molecular Systems, Branchburg, N.J.)) is placed into a 96 well plate and 25 μl of a denaturation reagent (1.25 N NaOH) is added. Five to 10 μl of the amplified material is then added to each well containing the sample diluent and denaturation solution. After all the samples are transferred, the ELISA plates are covered and the samples mixed by placing the plates on a rotary shaker for about 30 to 60 seconds. The plates are incubated at room temperature for 10 to 20 minutes before adding about 25 μl of the RNA probe (500 pmole/L in neutralization buffer) to each well. After all the samples are transferred, the plates are covered and the samples mixed by placing the plates on a rotary shaker for about 30 to 60 seconds followed by incubation at 65° C. for 25 to 35 minutes.

After incubation, the contents of each well is transferred into another 96 well plate previously coated with streptavidin. After all the samples are transferred, the plate(s) are covered and the samples are mixed by placing the plates on a rotary shaker for 25 to 35 minutes. This latter step allows for the RNA:DNA complexes comprising the incorporated biotin label to bind to the streptavidin-coated plate. After the incubation and removal of the contents of the well, 100 μl of an appropriately diluted antibody coupled to alkaline phosphatase that is targeted to recognize the RNA:DNA complexes is added to each well and incubated at room temperature for about 25 to 35 minutes on a rotary shaker.

Following incubation, each well is washed about 4-5 times with a buffered wash solution (e.g. 80 mM Tris pH 7.5, 150 mM NaCl, 0.05% Tween 20) to remove non-binding reagents. The RNA:DNA:antibody complexes that are bound to the plate are detected using an alkaline phosphatase substrate such as, for example, p-nitrophenyl phosphate (pNPP). The rate of reaction or intensity of the signal is measured at 405 nanometers using a standard ELISA plate reader. The amount of color corresponds to the relative amount of the RNA:DNA:antibody complex present in the well. The quantity of the D11 variant is interpolated from a standard curve comprised of various concentrations of the D11 variant or suitable control standard (e.g. calibrated plasmids, amplicons, etc.) that are treated in the same manner as the samples to be determined.

Example 2

Detection of Parvovirus B19 D11 Variant by Real-Time PCR

The D11 variant is also detected and/or quantified using real-time PCR, which is well known in the art.

Samples comprising viral nucleic acids are prepared as described above. Amplification is carried out in a PCR tube or plate using an appropriate volume of PCR working master mix. The working master mix comprises a buffer solution comprising i) D11 variant specific oligonucleotides of which one contains a fluorescent dye on its 5' end and a quencher near or at its 3'end, ii) deoxyribonucleotides, and iii) a thermophilic DNA polymerase with 5' to 3' exonuclease activity. Five to 15 μL of the resuspended samples are added to the PCR tube or plate containing the working master mix for amplification. Using real-time PCR such as, for example, the AB7300 Real-Time PCR System (Applied Biosystems), the samples and all relevant controls are amplified.

Real-time PCR amplification conditions comprise, for example, i) a step of denaturation (e.g. 94° C. for 60 seconds), ii) about forty cycles comprising thermal denaturation (e.g. 94° C. for 15 seconds) and polymerase extension (e.g. 65° C. for 30 seconds), and iii) a final step of polymerase extension (e.g. 60° C. for 7 minutes).

During amplification, the resulting amplicons are detected using an appropriate energy source to excite the fluorescent dye cleaved from the oligonucleotide and filters to capture the fluorescence emitted. This detection is performed during each amplification cycle by measuring the relative fluorescence of the target and comparing it to the background fluorescence of the sample and instrument. This relative fluorescence is plotted against a standard curve derived using known amounts of a characterized molecular standard and a quantity is assigned to the sample based on the known quantity of the controls used to generate the standard curve.

Example 3

Parvovirus B19 D11 Variant Infectivity Assay

To determine infectivity of the D11 variant, primer(s) and a probe are used to amplify and detect an amplicon from the D11 variant mRNA. The amplicon serves as an indicator of viral replication as described in *Virology* 301:374-380 (2002).

Cultured cells susceptible to parvovirus B19 infection or replication are either infected with D11 variant or transfected with the viral DNA. Following viral gene expression, the cells are lysed by a suitable buffer such as, for example, the guanidine-based buffer described above. Nucleic acid is recovered from the lysate by alcohol-based precipitation or by binding to a matrix in a column (e.g., Promega SV Total RNA Isolation System) or particle format such as magnetic beads (e.g., Ambion's MagMAX Viral RNA Isolation Kits). The recovered nucleic acid are washed to remove cellular debris and resuspended in a suitable solution, such as water or TE buffer. A fraction of the recovered nucleic acid is treated with DNase to degrade DNA. Accordingly, two types of samples are prepared, one with total infected cell nucleic acid and one enriched for infected cell RNA.

Oligonucleotide primer or primers and an intervening probe comprising DNA sequences unique to the D11 variant described herein are used to amplify and detect D11 variant RNA in the samples. The viral RNA is reverse transcribed into cDNA using standard techniques well known in the art. For example, specific primers or random oligomers are used to prime the reverse transcription step using a reagent such as, for example, SuperScript III Reverse Transcriptase (Invitrogen).

Following reverse transcription of viral RNA into cDNA, the D11 variant nucleic acid is amplified using standard amplification technologies such as, for example, PCR, Transcription Mediated Amplification (TMA), or Ligase Chain Reaction. The amplified parvovirus B19 variant product is detected following hybridization to a labeled complementary oligonucleotide probe comprising a label such as, for example, a radioactive, a fluorescent, or a biotin label. The label, and hence the variant, is detected, for example, by direct detection of the label, by release of fluorescence during amplification in a TaqMan reaction, or through an indirect detection such as binding of an enzyme to the biotin or binding of a labeled antibody to the probe. Alternatively, one can target regions that result in spliced mRNAs. The shorter amplified mRNA target can be readily differentiated from native DNA template using methods that discriminate nucleic acids based on length.

Example 4

Detection of Parvovirus B19 D11 Variant without Prior Amplification

The D11 variant is detected and/or quantified using non-amplification techniques well known in the art. These methods allow detection of very low abundance nucleic acid sequences due to detection of single molecules with a high signal-to-noise ratio.

For example, the polymerase extension reaction, as described in *Anal. Chem.* 76:4169 (2004), is used to detect parvovirus B19 variants in samples prepared as described above. Highly fluorescent nucleic acid reporter molecules are made based on a unique sequence of the parvovirus B19 variant target nucleic acid as template. For example, the reporter molecule is made by annealing an oligonucleotide primer unique to the D11 variant to the target. The primer is then extended with a DNA polymerase and free oligonucleotides. One of these free oligonucleotides is labeled with a fluorophore. Fluorescence detection indicates the presence of the D11 variant in the sample.

D11 variant is also detected in a sample using confocal single molecule detection (SMD) of fluorescent molecular beacons (MB) as described in *Analyst* 130:483 (2005). This technique utilizes an oligonucleotide with sequences unique to the parvovirus B19 D11 variant described herein. In its native conformation, the molecular beacon forms a hairpin structure where the close proximity of the quencher and fluorophore prevents fluorescence. The hairpin structure will be released upon annealing to the target parvovirus B19 variant oligonucleotide so that the fluorophore is released from the quencher causing fluorescence. This increase in fluorescence is detected by confocal microscopy.

D11 variant is also detected in a sample using a method as described in *Analyst* 131:484 (2006). Such a technique allows for rapid and sensitive detection of parvovirus B19 variant nucleic acids using two-color quantum dots (QDs) and single-molecule coincidence detection. Quantum dots (QDs) have broad excitation spectra with a narrow emission bandwidth and possess exceptional photochemical stability with relatively high quantum yield. According to this method, two biotinylated oligonucleotide probes unique to the D11 variant are used to recognize and detect specific complementary target DNA through a sandwich hybridization reaction. The DNA hybrid is first captured on the surface of one type of QD through specific streptavidin-biotin binding. A different type of QD with a different emission spectrum binds the other end of the DNA hybrid to form a QD/DNA hybrid/QD complex. This hybrid possesses coincident spectra due to the binding of both QDs that is absent when target D11 variant DNA is not present.

Example 5

Differential Detection of Parvovirus B19 D11 Variant-Specific Sequences

The D11 variant described herein is also differentially detected from among other parvovirus B19 such as Au, A6, V9, and D91.1. Samples are prepared as described above and D11 variant nucleic acid is detected using nucleic acid oligonucleotides that specifically target variant sequence but not the other genotypes. Sequence-specific variations among parvovirus B19 genotypes is determined using various alignment algorithms and/or programs known in the art including, but not limited to FASTA, BLAST, or ENTREZ (available through the National Center for Biotechnology Information, National Library of Medicine, National Institutes of Health, Bethesda, Md.). FASTA and BLAST are available as a part of the GCG sequence analysis package (University of Wisconsin, Madison, Wis.).

The targeted nucleic acid can be genomic DNA from intact virions or viral mRNA from parvovirus replicating in cells. Viral DNA or mRNA is prepared as described above and optionally, hybrid capture methods for the selection of specific sequences might be added in tandem to facilitate the enrichment of targeted nucleic acids. Nucleic acid sequences specific to the D11 variant are used as oligonucleotide primers for specific amplification of the variant nucleic acid, as labeled oligonucleotide probes for detection (e.g. incorporation of fluorophores, dyes, or other molecules used for detection), or as selective capture and retention moieties so as to enrich for the target variant while eliminating non-specific nucleic acid sequences.

Nucleic acid amplification and detection are performed as described above. For example, the variant nucleic acids are detected as part of an amplification reaction using labeled oligonucleotide probes (e.g. TaqMan or molecular beacons). Alternatively, variant nucleic acids are differentially amplified using primers specific to the D11 variant described herein and visualized using a variety of methods including, but not limited to gel electrophoresis, micro-well plate systems for detection of amplified nucleic acids, and various fluorogenic methodologies for generating signal as described in *J. Virol Methods* 136:210 (2006) and *J. Clin. Microbiol.* 44:2212 (2006).

Example 6

Identification of Conserved Regions of the Parvovirus B19 DNA Genome

To identify novel target regions of the parvovirus B19 genome that would expand the specificity of B19 detection assays to include detection of parvovirus B19 Genotypes 1, 2, 3, and variants and subtypes within each genotype, in silico analysis was performed to determine highly conserved regions of the parvovirus B19 genome by comparing Genotype 1, 2 and 3 partial and full coding sequences including the novel D11, E3, and P1 variants of the present invention.

A total of seven searches of GenBank (release 159) were performed to identify DNA sequences of parvovirus B19 variants and Genotypes 1, 2, and 3 prototype strains present in the database. These searches were performed using the following terms: 'parvovirus B19', 'Human parvovirus B19', 'Human parvovirus A6', 'Human parvovirus V9', 'Human parvovirus D91.1', 'parvovirus B19 genotype', and 'parvovirus B19 variant'. The identified DNA sequences were imported into the local Vector NTI database and filtered to exclude sequences shorter than 100 bases or longer than 5600 bases, sequences representing human B19 receptor and immunoglobulin genes, circular vectors, parvovirus 4, and parvovirus of other species such as simian and canine. Sequences shorter than 100 bases were omitted since the flanking regions are most likely primer derived and not necessarily actual native parvovirus sequence. Sequences longer than 5600 bases were omitted because the parvovirus B19 genome is only 5600 bases and sequences longer than this includes flanking regions of vector that would alter the consensus sequence. The other omitted sequences are not representative of native parvovirus B19 sequence, and therefore should not be included in the overall consensus calculation. The remaining DNA sequences including the novel D11, E3, and P1 variants of the present invention were aligned using the AlignX program in Vector NTI, v7.1 according to the Alignment Settings in Table 1. These are the default settings in Vector NTI, v.7.1. Pairwise alignment settings dictate the alignment of two individual sequences to each other, while multiple alignment settings dictate how each of the individual pairwise alignments are aligned with all other pairwise alignments.

TABLE 1

Alignment Settings for pairwise alignment (left) and multiple alignment (right) utilized to generate a multiple sequence alignment in Vector NTI, v7.1

| Pairwise Alignment | | Multiple Alignment | |
|---|---|---|---|
| Parameter | Setting | Parameter | Setting |
| Use FAST Algorithm | N/A | Gap Opening Penalty | 15 |
| K-tuple size | N/A | Gap Extension Penalty | 6.66 |
| Number of Best Diagonals | N/A | Gap Separation Penalty Range | 8 |
| Window Size | N/A | No End Gap Separation Penalty | N/A |
| Gap Penalty | N/A | % Identity for Alignment Delay | 40 |
| Gap Opening Penalty | 15 | Residue Specific Gaps Off | N/A |
| Gap Extension Penalty | 6.66 | Hydrophilic Residue Gap Off | N/A |
| | | Transition Weighting | 0 |

Consensus sequences were calculated at 100%, 99%, 98%, 97%, and 95% by Vector NTI according to the following Alignment Display Settings: Consider only identical residues in consensus calculation, Ignore gaps in consensus calculation, and the residue fraction for consensus was set at 1.0, 0.99, 0.98, 0.97, and 0.95 respectively. The function of using a specific sequence as a consensus was left un-checked. Table 2 shows the similarity table used in the consensus calculation. Only strong similarities were considered in consensus calculation.

TABLE 2

Alignment display setup nucleotide similarity table

| Residue | Strong Similarity |
|---|---|
| A | A |
| C | C |
| G | G |
| T | T |

The consensus sequence calculated at 97% provided the highest degree of sequence homology and minimal nucleotide gaps between the filtered parvovirus sequences. This was the consensus sequence used to design oligonucleotide primer and probe sets for evaluation in real-time PCR detection of parvovirus B19.

Initial identification of primer and probe sets was performed by visual inspection of conserved regions for presence of target regions. A target region was defined as a region in which primers and detection probes could be designed. Target regions were identified that had between 100 and 200 nucleotides and have two flanking sequences (primer binding regions) of 15 to 25 continuous nucleotides with an internal continuous sequence (probe binding region) greater than 20 nucleotides. Also, the internal sequence had to be in close proximity (within 20 nucleotides) to either flanking sequence. The identified primer sequences were further evaluated for primer dimer formation, presence of secondary structure, and melting temperature. Identified detection probes were evaluated to ensure; absence of secondary structure, absence of primer/probe dimers, absence of a 5' guanine residue, and the melting temperature was 7 to 10° C. higher than the flanking primer pair.

The combination of search terms in GenBank identified 881 DNA sequences that were imported into the local Vector NTI database. The 881 imported sequences were filtered according to the criteria stated above and the remaining 565 DNA sequences were aligned using the AlignX program in Vector NTI, v7.1.

A DNA consensus sequence was generated from the alignment of 565 parvovirus B19 DNA sequences utilizing the Alignment Display Settings of Vector NTI shown in Tables 1 and 2. Different DNA consensus sequences were generated with 100%, 99%, 98%, 97%, and 95% homology by changing the 'Residue fraction for consensus' value while retaining all other settings. The 97% consensus sequence was aligned with the Au isolate of B19 (Accession number: M13178) as the reference sequence (FIG. 5) to show the locations of the conserved regions and where no nucleotides are present at the 97% level of sequence homology.

A review of the 97% DNA sequence homology consensus revealed two regions of the parvovirus B19 genome as highly conserved across all of the 565 aligned parvovirus B19 sequences. Relative to parvovirus B19 Genotype 1 prototype strain Au, these two regions encompass nucleotides 1351 to 2426 (FIG. 6) and nucleotides 3704 to 4804 (FIG. 7).

The highly conserved sequence spanning nucleotides 1351 through 2426 was analyzed further to locate any DNA regions that could be utilized as target regions. Four (4) target regions were identified and designated region 1, 2, 4 and 5 (FIG. 8 and Table 3).

TABLE 3

Target Region and oligonucleotide sequences derived from highly conserved regions of the parvovirus B19 genome.

| Target Region | Function | Name | SEQ ID NO: | Sequence (5' to 3') | Tm |
|---|---|---|---|---|---|
| 1 | Forward primer | B19_2043F | 136 | TGAAACCCCGCGCTCTA | 59.6 |
| | Reverse primer | B19_2171R | 137 | AACTAACAGTTCACGAAACTG | 56.7 |
| | Detection probe | B19_2069F_FAM | 138 | TCCCCGGGACCAGTTCAGGAGAA | 68.1 |
| 2 | Forward primer | B19_1962F | 139 | TCAGCAGCAGTGGTGGT | 59.6 |
| | Reverse primer | B19_2043R | 140 | TAGAGCGCGGGGTTTCA | 59.6 |
| | Detection probe | B19_1979F-FAM | 141 | TGAAAGCTCTGAAGAACTCAGTGAAAGCAGCTTT | 67.0 |
| | Forward primer | B19_1903F | 142 | AATGCAGATGCCCTCCAC | 59.9 |
| | Detection probe | B19_1962F-FAM | 143 | TCAGCAGCAGTGGTGGTGAAAGCTCTGAA | 68.9 |
| | Reverse primer | B19_2027R | 144 | TGTTCCAGGCGCCTG | 58.9 |
| 3 | Forward primer | B19_4700F | 145 | CACAGCTACAGATGCAAA | 55.3 |
| | Reverse primer | B19_4769R | 146 | GGTGCACACGGCTTTT | 56.7 |
| | Detection probe | B19_4733R_FAM | 147 | TGTCCACAATTCTTCAGGCTTTTCATATCC | 64.6 |
| | Detection probe | B19_4733F_FAM | 148 | TGGATATGAAAAGCCTGAAGTATTGTGGAC | 64.6 |
| | Forward primer | B19_4672F | 149 | GGTCATTTACCATATGTACT | 54.2 |
| | Detection probe | B19_4703F-FAM | 150 | AGCTACAGATGCAAANCAACACCACAGACA† | 66.7 |
| 4 | Forward primer | B19_1500F | 151 | GAAAACTTTCCATTTAATGATGT | 53.8 |
| | Reverse primer | B19_1631R | 152 | ATTTTTTGATCTACCCTGGT | 54.2 |
| | Detection probe | B19_1537F-FAM | 153 | TTGGTGGTCTGGGATGAAGG | 62.4 |
| 5 | Forward primer | B19_1411F | 154 | GTTTTATGGGCCGCCAAGTA | 60.4 |
| | Reverse primer | B19_1537R | 155 | TTCATCCCAGACCACCAAGG | 62.4 |
| | Detection probe | B19_1450F-FAM | 156 | ATGGCTATTGCTAAAACTGTTCCAGTGTA | 63.2 |
| | Detection probe | B19_1492F-FAM | 157 | TGGAATAATGAAAACTTTCCATTTAATGATGTAG | 61.0 |
| | Detection probe | B19_1448F-FAM | 158 | CAATGGCCATTGCTAAAAGTGTTCCA | 63.0 |

†N = a universal base analogue including, without limitation, 5-nitroindole, inosine, and 4-nitrobenzimidazole.

The highly conserved sequence spanning nucleotides 3704 through 4804 was also analyzed further to locate any potential target regions. One (1) target region was identified and designated as region 3 (FIG. 8 and Table 3).

Figure 9:
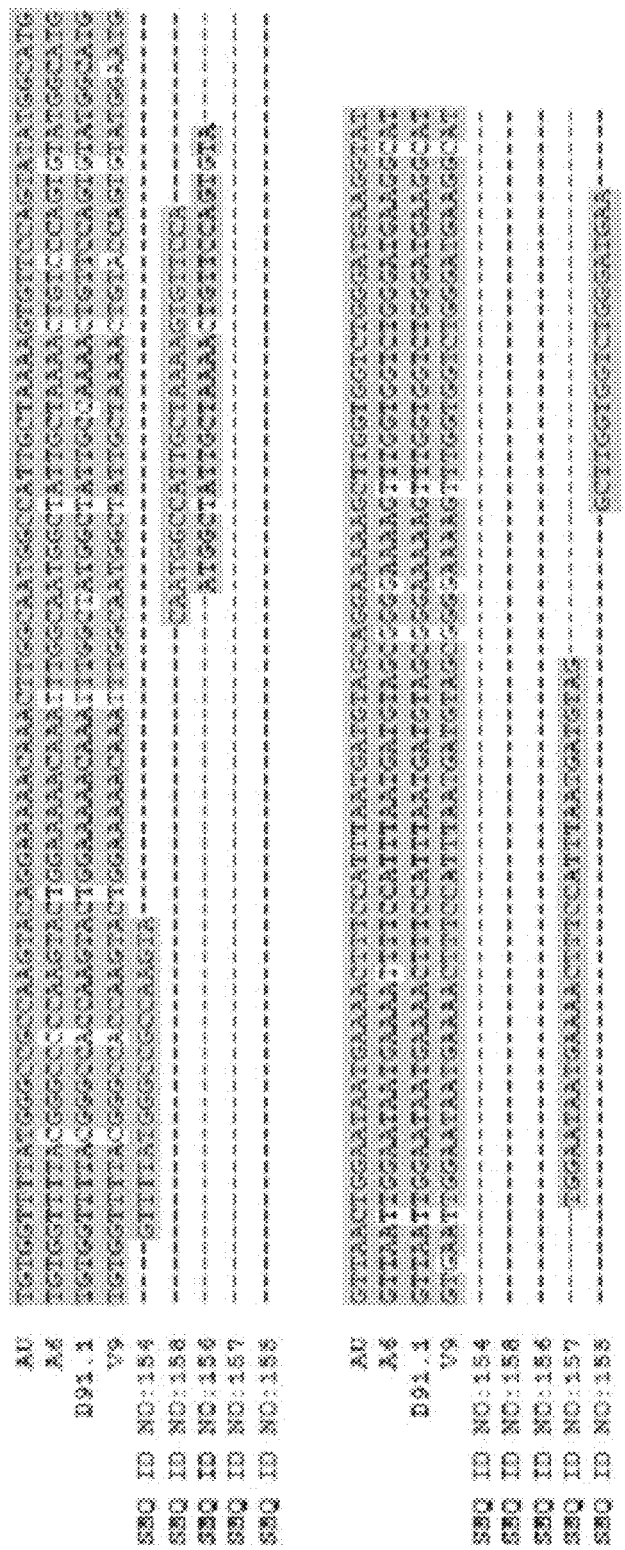
FIG. 9 shows alignment of the primers and probes of target region 5 with the parvovirus B19 genotype 1 Au isolate (i.e., nucleotides 1406 to 1485 of SEQ ID NO:130), the genotype 2 A6 isolate (i.e., nucleotides 1205 to 1284 of SEQ ID NO:131), and the genotype 3 isolates V9 (i.e., nucleotides 1298 to 1377 of SEQ ID NO:132) and D91.1 (i.e., nucleotides 1293 to 1372 of SEQ ID NO:133).

Regions 1, 2, 4 and 5 are positioned within the parvovirus B19 gene coding for non-structural protein 1 (NS1) and region 3 is positioned within overlapping genes coding for viral protein 1 and 2 (VP1, VP2) (FIG. 8). FIG. 9 shows alignment of e.g., primer/probe sequences of target region 5 to parvovirus B19 Genotype 1 prototype strain Au (i.e., SEQ ID NO:130).

Accordingly, an alignment of 565 parvovirus B19 variant and Genotype 1, 2, and 3 DNA sequences identified five highly conserved target regions of the parvovirus B19 genome at 97% DNA sequence homology. At the 97% DNA sequence homology, 13 oligonucleotide primers in 5 different regions were designed with 100 percent homology to the consensus sequence. At the same level, 10 oligonucleotide detection probes were designed. Of these 10 probes, 6 have a 100 percent homology. At least one probe (i.e., B19_4703-FAM) has 97% homology to the 97% consensus sequence. This probe, B19_4703-FAM, has one base at nucleotide 16 from the 5' end that is blank in the consensus sequence. A universal base (5-nitroindole) was inserted in this position to facilitate hybridization of the probe to the B19 viral DNA sequence. Exemplary universal base analogues include, without limitation, 5-nitroindole, inosine, and 4-nitrobenzimidazole.

Example 7

Evaluating a New Targeting Strategy for Parvovirus B19 Detection

The consensus sequence resulting from alignment of full and partial genomic sequences of human parvovirus B19 Genotypes 1, 2, and 3 present in GenBank was utilized to identify highly conserved regions of the parvovirus B19 genome and design oligonucleotide primers and probes within each conserved region (see Table 3 and FIG. 10). To evaluate experimentally whether the conserved DNA sequence regions identified as potential target regions for parvovirus B19 actually enhance the specificity of detection of parvovirus B19 variants and genotypes, oligonucleotide probes and primers were designed for amplification and detection of the identified conserved regions. A total of 16 primer/probe combination sets were evaluated (Table 4).

TABLE 4

Primer/Probe Combinations for B19 New Targeting Strategy Evaluation.

| Region | Primer/ Probe Set | SEQ ID NO: | Oligonucleotide Name | Tm (° C.) |
|---|---|---|---|---|
| 1 | 1 | 136 | B19_2043F | 59.6 |
| | | 137 | B19_2171R | 56.7 |
| | | 138 | B19_2069F_FAM | 68.1 |
| 2 | 2a | 139 | B19_1962F | 59.6 |
| | | 140 | B19_2043R | 59.6 |
| | | 141 | B19_1979F-FAM | 67.0 |
| | 2b | 139 | B19_1962F | 59.6 |
| | | 144 | B19_2027R | 58.9 |
| | | 141 | B19_1979F-FAM | 67.0 |
| | 2c | 142 | B19_1903F | 59.9 |
| | | 144 | B19_2027R | 58.9 |
| | | 141 | B19_1979F-FAM | 67.0 |
| | 2d | 142 | B19_1903F | 59.9 |
| | | 140 | B19_2043R | 59.6 |
| | | 141 | B19_1979F-FAM | 67.0 |
| | 2e | 142 | B19_1903F | 59.9 |
| | | 140 | B19_2043R | 59.6 |
| | | 143 | B19_1962F-FAM | 68.9 |

TABLE 4-continued

Primer/Probe Combinations for B19 New Targeting Strategy Evaluation.

| Region | Primer/ Probe Set | SEQ ID NO: | Oligonucleotide Name | Tm (° C.) |
|---|---|---|---|---|
| | 2f | 142 | B19_1903F | 59.9 |
| | | 144 | B19_2027R | 58.9 |
| | | 143 | B19_1962F-FAM | 68.9 |
| | 3a | 145 | B19_4700F | 55.3 |
| | | 146 | B19_4769R | 56.7 |
| | | 148 | B19_4733F_FAM | 64.6 |
| 3 | 3b | 145 | B19_4700F | 55.3 |
| | | 146 | B19_4769R | 56.7 |
| | | 147 | B19_4733R_FAM | 64.6 |
| | 3c | 149 | B19_4672F | 54.2 |
| | | 146 | B19_4769R | 56.7 |
| | | 150 | B19_4703F-FAM | 66.7 |
| | 3d | 149 | B19_4672F | 54.2 |
| | | 146 | B19_4769R | 56.7 |
| | | 148 | B19_4733F_FAM | 64.6 |
| | 3e | 149 | B19_4672F | 54.2 |
| | | 146 | B19_4769R | 56.7 |
| | | 147 | B19_4733R_FAM | 64.6 |
| 4 | 4 | 151 | B19_1500F | 53.8 |
| | | 152 | B19_1631R | 54.2 |
| | | 153 | B19_1537F-FAM | 62.4 |
| 5 | 5a | 154 | B19_1411F | 60.4 |
| | | 155 | B19_1537R | 62.4 |
| | | 156 | B19_1450E-FAM | 63.2 |
| | 5b | 154 | B19_1411F | 60.4 |
| | | 155 | B19_1537R | 62.4 |
| | | 157 | B19_1492F-FAM | 61.0 |
| | 5c | 154 | B19_1411F | 60.4 |
| | | 155 | B19_1537R | 62.4 |
| | | 158 | B19_1448F-FAM | 63.0 |

All oligonucleotides were purchased from Integrated DNA Technologies (IDT) (Coralville, Iowa) with 100 nmole synthesis scale for primers and 250 nmole scale for probes. Each oligonucleotide was suspended in RNase-, DNase-free water. A B19 master mix was prepared with the oligonucleotide sets (Table 4). The plasma samples utilized for extraction panels are: NAT-056 (Genotype 1), E3 (i.e., SEQ ID NO: 128) (Genotype 1), P1 (i.e., SEQ ID NO: 129) (Genotype 3). Plasma containing parvovirus B19 Genotype 2 is currently not available for assessment. A full-length Genotype 2 amplicon may be obtained for future assessment. Dilution panels of P1 (i.e., SEQ ID NO: 129) and E3 (i.e., SEQ ID NO: 128) were made for initial extraction by 10 fold serial dilutions of the stock material to a $10^{-9}$ final dilution in normal human plasma. The $10^{-4}$, $10^{-7}$, and $10^{-9}$ test sample dilutions were evaluated with the primer and probe combinations in Table 4. Each extraction set included the test samples and controls listed in Table 5.

TABLE 5

Test samples and controls utilized for assessment of primers and probes

| Sample | Dilution | N Size |
|---|---|---|
| B19 Negative Control | NA | 3 |
| B19 Low Positive Control | NA | 3 |
| B19 High Positive Control | NA | 3 |
| B19 100 IU/mL | NA | 2 |
| E3 1.0 × $10^{-4}$ | 1:$10^4$ | 2 |
| E3 1.0 × $10^{-7}$ | 1:$10^7$ | 2 |
| E3 1.0 × $10^{-9}$ | 1:$10^9$ | 2 |
| P1 1.0 × $10^{-4}$ | 1:$10^4$ | 2 |
| P1 1.0 × $10^{-7}$ | 1:$10^7$ | 2 |
| P1 1.0 × $10^{-9}$ | 1:$10^9$ | 2 |

Amplification and detection were performed on the AB7300 Real Time PCR System (Applied Biosystems, Foster City, Calif.). All extracted samples were amplified in duplicate. The amplification controls included five B19 quantification standards for each oligonucleotide set. The assay controls consisted of the B19 Negative Control, B19 Low Positive Control, and B19 High Positive Control. The test master mixes used to amplify the extracted samples were made using the different primer and probe combinations listed in Table 4. Each primer and probe combination was amplified at 2 anneal/extension temperatures: 60° C. and 55° C. to accommodate lower melting temperatures (Tm) of some primers and probes (Table 4).

Results for parvovirus B19 detection for each of the primer and probe combinations at 55° C. and 60° C. for each sample concentration is shown in Table 6.

TABLE 6

Summary of parvovirus B19 amplification and detection for primer probe sets amplified at 55° C. and 60° C. anneal/extension temperatures.

| Primer/Probe Set | Sample | Temperature 55° C. | 60° C. | Comments |
|---|---|---|---|---|
| 1 | P1 | + | + | Good detection |
|   | E3 | + | + |   |
| 2a | P1 | + | + | Did not detect $10^{-9}$ test sample dilution at 55° C. All test sample dilutions were detected at 60° C. |
|   | E3 | + | + |   |
| 2b | P1 | − | − | Primer/probe failure likely due to proximity of primer to probe proximity |
|   | E3 | − | − |   |
| 2c | P1 | − | − | Reverse primer B19_2027R unable to amplify and detect target |
|   | E3 | − | − |   |
| 2d | P1 | + | + | Good detection, especially at 60° C. |
|   | E3 | + | + |   |
| 2e | P1 | + | + | Good detection at 60° C. Did not detect all $10^{-9}$ test sample dilutions |
|   | E3 | + | + |   |
| 2f | P1 | − | − | Not analyzed since reverse primer shared with Primer/probe Set 2c |
|   | E3 | − | − |   |
| 3a | P1 | + | + | At 60° C., only 104 test sample dilution amplified and detected |
|   | E3 | + | + | Good detection at 55° C. |
| 3b | P1 | + | + | Good detection |
|   | E3 | + | + |   |
| 3c | P1 | + | + | Good detection at 55° C. |
|   | E3 | + | + | At 60° C., only 104 test sample dilution amplified and detected |
| 3d | P1 | + | + | No robust amplification and detection at low test sample concentrations |
|   | E3 | + | + |   |
| 3e | P1 | + | + | No robust amplification and detection at low test sample concentrations |
|   | E3 | + | + |   |
| 4 | P1 | + | − | Poor detection at 55° C. |
|   | E3 | + | − | No detection at 60° C. |
| 5a | P1 | + | − |   |
|   | E3 | + | − |   |
| 5b | P1 | + | + | Good detection |
|   | E3 | + | + | Good detection |
| 5c | P1 | − | − |   |
|   | E3 | + | + | Good detection |

Key: (+) indicates detection and (−) indicates no detection.

Figure 11:
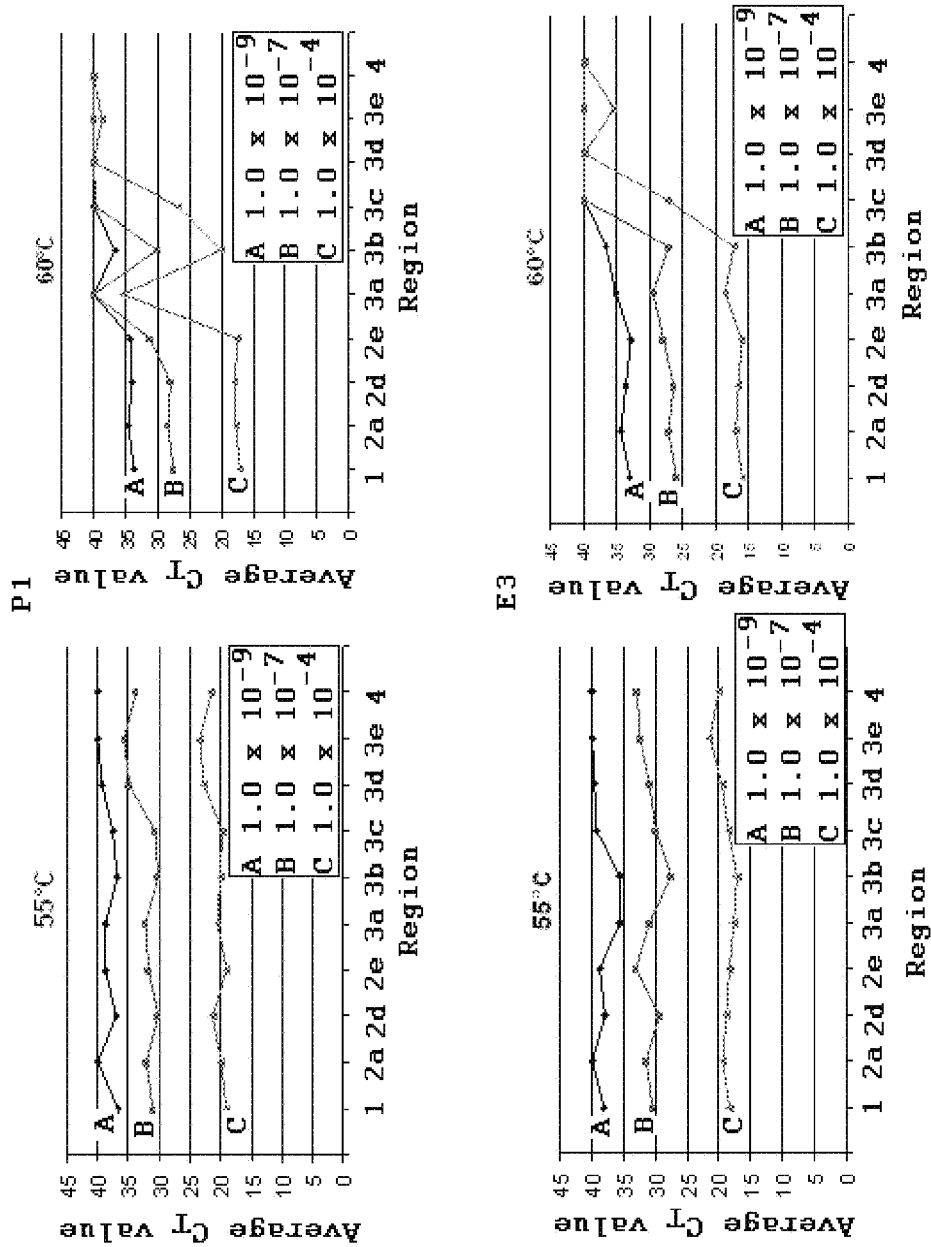
FIG. 11 shows average $C_T$ values for P1 (i.e., SEQ ID NO: 129) and E3 (i.e., SEQ ID NO: 128) across target regions 1 through 4. Test sample dilutions that showed no amplification and detection are plotted as $C_T=40$.
Figure 12:
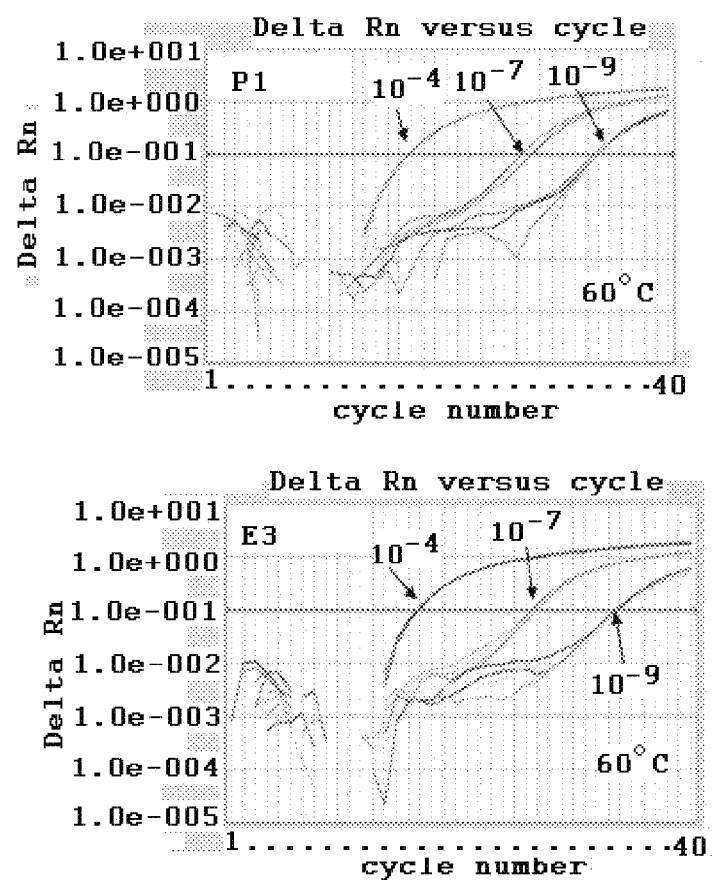
FIG. 12 shows amplification plots for Primer/probe Set 2d at 60° C.: P1 (i.e., SEQ ID NO: 129) and E3 (i.e., SEQ ID NO: 128).
Figure 13:
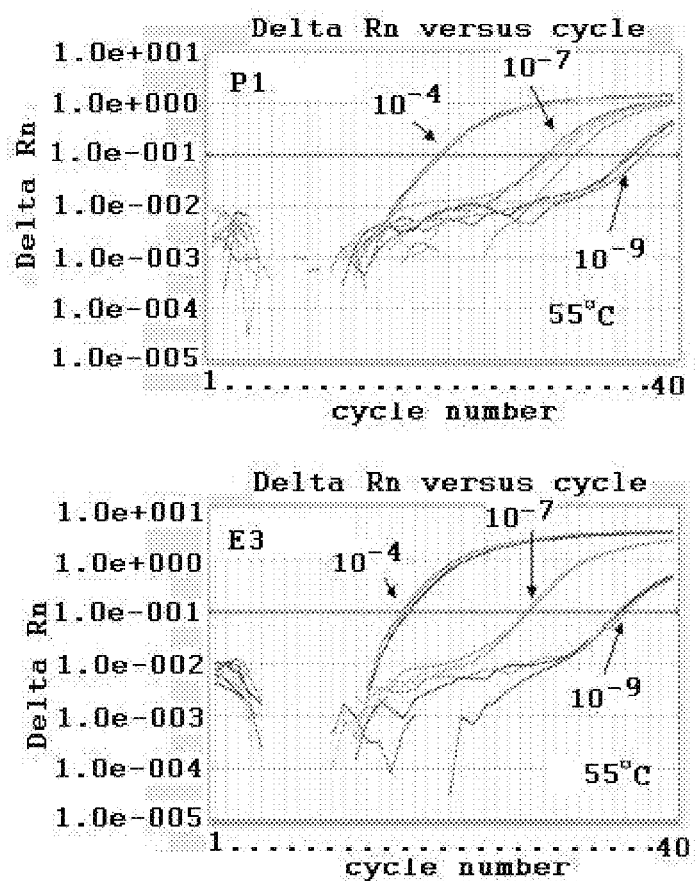
FIG. 13 shows amplification plots for Primer/probe Set 3b at 55° C.: P1 (i.e., SEQ ID NO: 129) and E3 (i.e., SEQ ID NO: 128).

Thirteen out of 16 primer/probe sets representing all 5 conserved regions showed detection of P1 (i.e., SEQ ID NO: 129) and/or E3 (i.e., SEQ ID NO: 128). Primer/probe Set 2b did not demonstrate amplification and detection. Further oligonucleotide and B19 genomic region sequence analysis proved that the probe and forward primer were positioned too close to each other (probe overlapping the 3' end of the primer) to generate amplification and detection. Primer/probe Set 2c also did not demonstrate amplification and detection, most likely due to poor design/performance of the reverse primer. Primer/probe Set 2f was not analyzed because it shared the same reverse primer with Primer/probe Set 2c. The average $C_T$ values from the amplification and detection of P1 (i.e., SEQ ID NO: 129) and E3 (i.e., SEQ ID NO: 128) at both anneal/extension temperatures for 10 of the 12 primer/probe sets are shown in FIG. 11. Examples of amplification plots are shown for Primer/probe Sets 2d and 3b in FIGS. 12 and 13.

All 5 target regions that were identified as conserved regions of the parvovirus B19 genome showed detection of both P1 and E3 variants, confirming that these target regions were conserved at least for parvovirus B19 genotypes 1 and 3. Primer/probe sets designed to detect the 5 target regions provided good robust amplification and detection.

What is claimed is:

1. A method for determining the presence of parvovirus B19 in a sample, the method comprising:
    (a) performing an amplification step in which any parvovirus B19 nucleic acid present in the sample is amplified with at least one pair of primers comprising a first primer and a second primer, wherein the first primer comprises the nucleotide sequence as set forth in (SEQ ID NO:159); and
    (b) performing a detection step which determines the presence or absence of an amplicon generated in step (a), comprising contacting the product of step (a) with a polynucleotide probe comprising the nucleotide sequence as set forth in (SEQ ID NO:160) or (SEQ ID NO:161), wherein positive detection of the amplicon indicates presence of a parvovirus B19 genotype 2 or 3 in the sample.

2. The method of claim 1, wherein the second primer comprises the sequence as set forth in (SEQ ID NO:162).

3. The method of claim 1, wherein the polynucleotide probe comprises a quencher molecule coupled to a pyrimidine ring of a thymine base.

4. The method of claim 3, wherein the thymidine base is in nucleotide position 10 of (SEQ ID NO:160).

5. The method of claim 3, wherein the quencher is a Black Hole Quencher®.

6. The method of claim 5, wherein the Black Hole Quencher® is BHQ1.

7. The method of claim 1, wherein the polynucleotide probe comprises a quencher molecule incorporated into the backbone of the probe.

8. The method of claim 7, wherein the quencher replaces the nucleotide at position 10 of (SEQ ID NO:160).

9. A method for determining the presence of parvovirus B19 in a sample, the method comprising:
   (a) performing an amplification step in which parvovirus B19 nucleic acid which may be present in the sample is amplified with at least one pair of primers comprising a first primer and a second primer, wherein the first primer comprises the nucleotide sequence as set forth in (SEQ ID NO:159) and the second primer comprises the nucleotide sequence as set forth in (SEQ ID NO:162); and
   (b) performing a detection step which determines the presence or absence of an amplicon generated in step (a), comprising contacting the product of step (a) with a polynucleotide probe, wherein positive detection of the amplicon indicates presence of a parvovirus B19 genotype 2 or 3 in the sample.

10. The method of claim 9, wherein the polynucleotide probe comprises the nucleotide sequence as set forth in (SEQ ID NO:160) or (SEQ ID NO:161).

11. The method of claim 9, wherein the polynucleotide probe comprises a quencher molecule coupled to a pyrimidine ring of a thymine base.

12. The method of claim 11, wherein the thymidine base is in nucleotide position 10 of (SEQ ID NO:160).

13. The method of claim 11, wherein the quencher is a Black Hole Quencher®.

14. The method of claim 13, wherein the Black Hole Quencher® is BHQ1.

15. The method of claim 9, wherein the polynucleotide probe comprises a quencher molecule incorporated into the backbone of the probe.

16. The method of claim 15, wherein the quencher replaces the nucleotide at position 10 of (SEQ ID NO:160).

\* \* \* \* \*